US012369965B2

(12) United States Patent
Kannan et al.

(10) Patent No.: US 12,369,965 B2
(45) Date of Patent: Jul. 29, 2025

(54) SYSTEMS AND METHODS FOR TREATMENT OF OBSTRUCTIVE SLEEP APNEA

(71) Applicant: CRYOSA, INC., Arden Hills, MN (US)

(72) Inventors: Srinivas Kannan, Arden Hills, MN (US); Orhan Soykan, Arden Hills, MN (US); Mark Christopherson, Arden Hills, MN (US); Donald A. Gonzales, Arden Hills, MN (US); Stefan Skorich, Arden Hills, MN (US); Guy Vanney, Arden Hills, MN (US); Douglas Krone, Arden Hills, MN (US); Matthew Anthony Bachmeier, Arden Hills, MN (US)

(73) Assignee: CRYOSA, INC., Arden Hills, MN (US)

( * ) Notice: Subject to any disclaimer, the term of this patent is extended or adjusted under 35 U.S.C. 154(b) by 0 days.

(21) Appl. No.: 18/645,088

(22) Filed: Apr. 24, 2024

(65) Prior Publication Data

US 2024/0341830 A1    Oct. 17, 2024

Related U.S. Application Data

(63) Continuation of application No. PCT/US2022/082620, filed on Dec. 30, 2022.
(Continued)

(51) Int. Cl.
*A61B 18/02* (2006.01)
*A61F 5/56* (2006.01)
*A61B 18/00* (2006.01)

(52) U.S. Cl.
CPC .......... *A61B 18/0218* (2013.01); *A61F 5/566* (2013.01); *A61B 2018/00321* (2013.01);
(Continued)

(58) Field of Classification Search
CPC ...... A61B 18/0218; A61B 2018/00321; A61B 2018/00327; A61B 2018/00714; A61B 2018/0212; A61B 2018/0262
See application file for complete search history.

(56) References Cited

U.S. PATENT DOCUMENTS 3,712,306 A    1/1973   Bryne
5,245,023 A    9/1993   Peoples et al.
(Continued)

FOREIGN PATENT DOCUMENTS

AU    2011279923 B2    2/2016
AU    2018226785 A1    10/2019
(Continued)

OTHER PUBLICATIONS

Avram, M.M. et al., "Cryolipolysis for Subcutaneous Fat Layer Reduction." Lasers in Surgery and Medicine, 41: 703-708 (2009).
(Continued)

*Primary Examiner* — Daniel W Fowler
(74) *Attorney, Agent, or Firm* — Perkins Coie LLP

(57) ABSTRACT

Methods, devices, and systems employ cryolysis of oropharyngeal adipose tissues to selectively remove fat cells from the tissues causing obstructive sleep apnea. In various embodiments, a chilled liquid—e.g., a liquid or air—is applied to the target tissue at a temperature and for a duration sufficient to cause cryolysis.

13 Claims, 70 Drawing Sheets

Related U.S. Application Data

(60) Provisional application No. 63/295,416, filed on Dec. 30, 2021.

(52) U.S. Cl.
CPC ........... *A61B 2018/00327* (2013.01); *A61B 2018/00714* (2013.01); *A61B 2018/0212* (2013.01); *A61B 2018/0262* (2013.01)

(56) References Cited

U.S. PATENT DOCUMENTS

| | | |
|---|---|---|
| 5,250,430 A | 10/1993 | Peoples et al. |
| 5,534,432 A | 7/1996 | Peoples et al. |
| 5,663,063 A | 9/1997 | Peoples et al. |
| 5,743,904 A * | 4/1998 | Edwards ............ A61N 1/06 606/32 |
| 5,800,379 A | 9/1998 | Edwards et al. |
| 6,017,337 A | 1/2000 | Pira |
| 6,032,675 A | 3/2000 | Rubinsky |
| 6,041,787 A | 3/2000 | Rubinsky |
| 6,045,549 A | 4/2000 | Smethers et al. |
| 6,126,657 A | 10/2000 | Edward et al. |
| 6,245,537 B1 | 6/2001 | Williams et al. |
| 6,316,262 B1 | 11/2001 | Huisman et al. |
| 6,378,525 B1 | 4/2002 | Beyar et al. |
| 6,408,851 B1 | 6/2002 | Karell |
| 6,514,515 B1 | 2/2003 | Williams et al. |
| 6,548,569 B1 | 4/2003 | Williams et al. |
| 6,555,123 B2 | 4/2003 | Williams et al. |
| 6,585,994 B2 | 7/2003 | Williams et al. |
| 6,592,892 B1 | 7/2003 | Williams et al. |
| 6,593,116 B1 | 7/2003 | Huisman et al. |
| 6,610,764 B1 | 8/2003 | Martin et al. |
| 6,623,749 B2 | 9/2003 | Williams et al. |
| 6,689,589 B2 | 2/2004 | Huisman et al. |
| 6,746,447 B2 | 6/2004 | Davison et al. |
| 6,746,685 B2 | 6/2004 | Williams et al. |
| 6,770,071 B2 | 8/2004 | Woloszko et al. |
| 6,828,357 B1 | 12/2004 | Martin et al. |
| 6,838,493 B2 | 1/2005 | Williams et al. |
| 6,867,247 B2 | 3/2005 | Williams et al. |
| 6,867,248 B1 | 3/2005 | Martin et al. |
| 6,878,758 B2 | 4/2005 | Martin et al. |
| D568,258 S | 5/2008 | Adam |
| 7,367,341 B2 | 5/2008 | Anderson et al. |
| 7,458,932 B2 | 12/2008 | Sun |
| 7,507,235 B2 | 3/2009 | Keogh et al. |
| 7,575,870 B1 | 8/2009 | Lalvani et al. |
| 7,713,266 B2 | 5/2010 | Elkins et al. |
| 7,842,029 B2 | 11/2010 | Anderson et al. |
| 7,850,683 B2 | 12/2010 | Elkins et al. |
| 7,854,754 B2 | 12/2010 | Ting et al. |
| 7,862,558 B2 | 1/2011 | Elkins et al. |
| 7,998,137 B2 | 8/2011 | Elkins et al. |
| 8,192,474 B2 | 6/2012 | Levinson et al. |
| 8,275,442 B2 | 9/2012 | Allison |
| 8,285,390 B2 | 10/2012 | Levinson et al. |
| 8,287,579 B2 | 10/2012 | Nimitz |
| 8,298,216 B2 | 10/2012 | Burger et al. |
| 8,337,539 B2 | 12/2012 | Ting et al. |
| 8,409,185 B2 | 4/2013 | Burger et al. |
| 8,523,927 B2 | 9/2013 | Levinson et al. |
| 8,603,073 B2 | 12/2013 | Allison |
| 8,676,338 B2 | 3/2014 | Levinson et al. |
| 8,702,774 B2 | 4/2014 | Baker et al. |
| 8,715,275 B2 | 5/2014 | Burger et al. |
| 8,768,468 B2 | 7/2014 | Garcia et al. |
| 8,834,547 B2 | 9/2014 | Anderson et al. |
| 8,840,608 B2 | 9/2014 | Anderson et al. |
| 9,033,966 B2 | 5/2015 | McKay |
| 9,039,688 B2 | 5/2015 | Palmer et al. |
| 9,072,498 B2 | 7/2015 | Elkins et al. |
| 9,078,634 B2 | 7/2015 | Gonzales et al. |
| 9,101,346 B2 | 8/2015 | Burger et al. |
| 9,113,855 B2 | 8/2015 | Burger et al. |
| 9,254,162 B2 | 2/2016 | Burger et al. |
| 9,295,512 B2 | 3/2016 | Allison et al. |
| 9,308,120 B2 | 4/2016 | Anderson et al. |
| 9,314,290 B2 | 4/2016 | Fourkas et al. |
| 9,345,526 B2 | 5/2016 | Elkins et al. |
| 9,402,676 B2 | 8/2016 | Babkin et al. |
| 9,408,745 B2 | 8/2016 | Levinson et al. |
| 9,439,805 B2 | 9/2016 | Gonzales et al. |
| 9,545,523 B2 | 1/2017 | Nanda |
| 9,610,112 B2 | 4/2017 | Karnik et al. |
| 9,844,461 B2 | 12/2017 | Levinson et al. |
| 9,861,421 B2 | 1/2018 | O'Neil et al. |
| 9,907,693 B2 | 3/2018 | Burger et al. |
| 9,980,765 B2 | 5/2018 | Avram et al. |
| 10,085,881 B2 | 10/2018 | Karnik et al. |
| 10,092,346 B2 | 10/2018 | Levinson et al. |
| 10,111,774 B2 | 10/2018 | Gonzales et al. |
| 10,201,380 B2 | 2/2019 | DeBenedictis et al. |
| 10,213,244 B2 | 2/2019 | Fourkas et al. |
| 10,363,080 B2 | 7/2019 | Elkins et al. |
| 10,441,459 B2 | 10/2019 | Aronhalt et al. |
| 10,470,813 B2 | 11/2019 | Allison et al. |
| 10,568,759 B2 | 2/2020 | Yee et al. |
| 10,575,890 B2 | 3/2020 | DeBenedictis et al. |
| 10,582,960 B2 | 3/2020 | Avram et al. |
| 10,596,030 B2 | 3/2020 | Karnik et al. |
| 10,646,666 B2 | 5/2020 | Cohn et al. |
| 10,675,178 B2 | 6/2020 | Levinson et al. |
| 10,806,500 B2 | 10/2020 | DeBenedictis et al. |
| 10,864,112 B2 | 12/2020 | Burger et al. |
| 10,869,779 B2 | 12/2020 | Burger et al. |
| 10,888,366 B2 | 1/2021 | Allison et al. |
| 10,912,599 B2 | 2/2021 | O'Neil et al. |
| 10,939,947 B2 | 3/2021 | Burger et al. |
| 11,076,879 B2 | 8/2021 | Yee et al. |
| 11,116,566 B2 | 9/2021 | Dinger et al. |
| 11,154,418 B2 | 10/2021 | Frangineas |
| 11,253,393 B2 | 2/2022 | Karnik et al. |
| 11,272,972 B2 | 3/2022 | Allison et al. |
| 11,284,934 B2 | 3/2022 | Lazarus et al. |
| 11,324,673 B2 | 5/2022 | Velis et al. |
| 11,419,757 B2 | 8/2022 | Gonzales et al. |
| 11,437,150 B2 | 9/2022 | Rondoni et al. |
| 11,439,532 B2 | 9/2022 | Vellis |
| 11,446,175 B2 | 9/2022 | Jimenez Lozano et al. |
| 11,446,178 B2 | 9/2022 | Velis |
| D967,164 S | 10/2022 | Mairs et al. |
| 11,457,971 B2 | 10/2022 | Wolf et al. |
| 11,478,643 B2 | 10/2022 | Verzal et al. |
| 11,504,322 B2 | 11/2022 | Garibyan et al. |
| 11,510,722 B2 | 11/2022 | Wolf et al. |
| 11,511,117 B2 | 11/2022 | Ni et al. |
| D971,935 S | 12/2022 | Mairs et al. |
| D971,936 S | 12/2022 | Mairs et al. |
| D971,937 S | 12/2022 | Mairs et al. |
| D971,950 S | 12/2022 | Mairs et al. |
| 11,517,365 B1 | 12/2022 | Mazor et al. |
| 11,534,335 B2 | 12/2022 | Gonzales et al. |
| 11,583,438 B1 | 2/2023 | Levinson et al. |
| 2002/0026226 A1 | 2/2002 | Ein |
| 2002/0062831 A1 | 5/2002 | Beyar et al. |
| 2002/0164729 A1 | 11/2002 | Skraly et al. |
| 2003/0060685 A1 | 3/2003 | Houser |
| 2003/0069572 A1 | 4/2003 | Wellman |
| 2003/0220374 A1 | 11/2003 | Needleman |
| 2003/0220674 A1 | 11/2003 | Anderson et al. |
| 2004/0234576 A1 | 11/2004 | Martin et al. |
| 2004/0249416 A1 | 12/2004 | Yun et al. |
| 2005/0043682 A1* | 2/2005 | Kucklick ............ A61M 3/0279 604/167.03 |
| 2005/0133026 A1 | 6/2005 | Seleznev et al. |
| 2006/0235264 A1 | 10/2006 | Vassallo |
| 2007/0010861 A1 | 1/2007 | Anderson et al. |
| 2007/0129714 A1 | 6/2007 | Elkins et al. |
| 2007/0144539 A1 | 6/2007 | van der Burg et al. |
| 2007/0154538 A1 | 7/2007 | Neuberger et al. |
| 2007/0163603 A1 | 7/2007 | Sikora |
| 2007/0198071 A1 | 8/2007 | Ting et al. |

(56) References Cited

U.S. PATENT DOCUMENTS

| | | |
|---|---|---|
| 2007/0255362 A1 | 11/2007 | Levinson et al. |
| 2007/0270925 A1 | 11/2007 | Levinson et al. |
| 2008/0023012 A1 | 1/2008 | Dineen et al. |
| 2008/0058584 A1 | 3/2008 | Hirotsuka et al. |
| 2008/0066769 A1 | 3/2008 | Dineen et al. |
| 2008/0066864 A1 | 3/2008 | Ballantine et al. |
| 2008/0077201 A1 | 3/2008 | Levinson et al. |
| 2008/0077202 A1 | 3/2008 | Levinson et al. |
| 2008/0077211 A1 | 3/2008 | Levinson et al. |
| 2008/0083461 A1 | 4/2008 | Viken |
| 2008/0132891 A1* | 6/2008 | Nobis .................... A61B 17/29 606/45 |
| 2008/0183164 A1 | 7/2008 | Elkins et al. |
| 2008/0188947 A1 | 8/2008 | Sanders |
| 2008/0200910 A1 | 8/2008 | Burger et al. |
| 2008/0287839 A1 | 11/2008 | Rosen et al. |
| 2009/0014012 A1 | 1/2009 | Sanders |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0107001 A1 | 4/2009 | McCarty |
| 2009/0118722 A1 | 5/2009 | Ebbers et al. |
| 2009/0120446 A1 | 5/2009 | Vaska et al. |
| 2009/0123886 A1 | 5/2009 | Vaska et al. |
| 2009/0149929 A1 | 6/2009 | Levinson et al. |
| 2009/0192504 A1 | 7/2009 | Askew |
| 2009/0287060 A1 | 11/2009 | Pell et al. |
| 2009/0287210 A1* | 11/2009 | Kauphusman ....... A61B 5/6852 606/1 |
| 2010/0057065 A1 | 3/2010 | Krimsky |
| 2010/0081971 A1 | 4/2010 | Allison |
| 2010/0100089 A1 | 4/2010 | Niethammer |
| 2010/0152824 A1 | 6/2010 | Allison |
| 2010/0280582 A1 | 11/2010 | Baker |
| 2011/0066216 A1 | 3/2011 | Ting et al. |
| 2011/0155143 A1 | 6/2011 | Shantha |
| 2011/0166598 A1 | 7/2011 | Gonzales et al. |
| 2011/0224761 A1 | 9/2011 | Manstein |
| 2011/0238050 A1 | 9/2011 | Allison et al. |
| 2011/0238051 A1 | 9/2011 | Levinson et al. |
| 2011/0300079 A1 | 12/2011 | Martin et al. |
| 2012/0022518 A1 | 1/2012 | Levinson et al. |
| 2012/0239123 A1 | 9/2012 | Weber et al. |
| 2012/0265186 A1* | 10/2012 | Burger ............... A61M 25/0138 606/41 |
| 2013/0066309 A1 | 3/2013 | Levinson et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0158440 A1 | 6/2013 | Allison |
| 2013/0158636 A1 | 6/2013 | Ting et al. |
| 2013/0245731 A1 | 9/2013 | Allison |
| 2013/0253384 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2014/0005760 A1 | 1/2014 | Levinson et al. |
| 2014/0067025 A1 | 3/2014 | Levinson et al. |
| 2014/0257443 A1 | 9/2014 | Baker et al. |
| 2014/0277219 A1 | 9/2014 | Nanda |
| 2014/0277302 A1 | 9/2014 | Weber et al. |
| 2014/0316393 A1 | 10/2014 | Levinson et al. |
| 2015/0047301 A1 | 2/2015 | Messersi |
| 2015/0148791 A1 | 5/2015 | Birdsall et al. |
| 2015/0216719 A1 | 8/2015 | DeBenedictis et al. |
| 2015/0216720 A1 | 8/2015 | DeBenedictis et al. |
| 2015/0216816 A1 | 8/2015 | O'Neil et al. |
| 2015/0251120 A1 | 9/2015 | Jakop |
| 2016/0022345 A1 | 1/2016 | Baust et al. |
| 2016/0051401 A1 | 2/2016 | Yee et al. |
| 2016/0183997 A1 | 6/2016 | Burnett et al. |
| 2016/0324576 A1* | 11/2016 | Ebbutt ............... A61B 18/1815 |
| 2016/0338752 A1* | 11/2016 | Sperling ................ A61B 90/04 |
| 2016/0354234 A1 | 12/2016 | Dabrowiak |
| 2017/0079833 A1 | 3/2017 | Frangineas et al. |
| 2017/0105869 A1 | 4/2017 | Frangineas et al. |
| 2017/0196731 A1 | 7/2017 | DeBenedictis et al. |
| 2017/0239079 A1 | 8/2017 | Root et al. |
| 2017/0246032 A1* | 8/2017 | Gonzales .................. A61F 7/12 |
| 2017/0325992 A1 | 11/2017 | DeBenedictis et al. |
| 2017/0325993 A1 | 11/2017 | Lozano et al. |
| 2017/0326042 A1 | 11/2017 | Zeng et al. |
| 2017/0326346 A1 | 11/2017 | Lozano et al. |
| 2018/0185081 A1 | 7/2018 | O'Neil et al. |
| 2018/0206900 A1* | 7/2018 | Sperling ............ A61B 18/1492 |
| 2018/0235805 A1 | 8/2018 | Burger et al. |
| 2019/0069949 A1 | 3/2019 | Vrba et al. |
| 2019/0151006 A1 | 5/2019 | Fourkas et al. |
| 2019/0192873 A1 | 6/2019 | Schwarz et al. |
| 2019/0197361 A1 | 6/2019 | Gonzales et al. |
| 2019/0254867 A1 | 8/2019 | Gonzales et al. |
| 2019/0290347 A1 | 9/2019 | Elkins et al. |
| 2020/0046552 A1 | 2/2020 | Velis et al. |
| 2020/0069458 A1 | 3/2020 | Pham |
| 2020/0138501 A1 | 5/2020 | DeBenedictis et al. |
| 2020/0206024 A1 | 7/2020 | Karnik et al. |
| 2020/0222103 A1* | 7/2020 | Manstein ............... A61B 18/02 |
| 2020/0268439 A1 | 8/2020 | Frazier et al. |
| 2020/0323682 A1 | 10/2020 | O'Connor et al. |
| 2020/0375647 A1 | 12/2020 | Alphandery et al. |
| 2021/0030457 A1 | 2/2021 | Avram et al. |
| 2021/0038278 A1 | 2/2021 | DeBenedictis et al. |
| 2021/0128219 A1 | 5/2021 | Allison et al. |
| 2021/0186585 A1 | 6/2021 | Burger et al. |
| 2021/0282829 A1 | 9/2021 | O'Neil et al. |
| 2021/0315626 A1 | 10/2021 | Xiao et al. |
| 2021/0322084 A1 | 10/2021 | Velis et al. |
| 2021/0353351 A1 | 11/2021 | Mazor et al. |
| 2022/0008110 A1 | 1/2022 | Velis et al. |
| 2022/0047315 A1 | 2/2022 | Baker et al. |
| 2022/0071802 A1 | 3/2022 | Christopherson et al. |
| 2022/0125630 A1 | 4/2022 | Karnik et al. |
| 2022/0133531 A1 | 5/2022 | Salma et al. |
| 2022/0226206 A1 | 7/2022 | Velis |
| 2022/0233863 A1 | 7/2022 | Rondoni et al. |
| 2022/0257272 A1 | 8/2022 | Wolf et al. |
| 2022/0265344 A1 | 8/2022 | Wolf et al. |
| 2022/0280788 A1 | 9/2022 | Verzal et al. |
| 2022/0288388 A1 | 9/2022 | Rondoni et al. |
| 2022/0296887 A1 | 9/2022 | Johnson et al. |
| 2022/0338892 A1 | 10/2022 | Iyer et al. |
| 2022/0346852 A1 | 11/2022 | Anderson et al. |
| 2022/0387091 A1 | 12/2022 | DeBenedictis et al. |
| 2022/0401725 A1 | 12/2022 | Dieken et al. |
| 2022/0401727 A1 | 12/2022 | Rondoni et al. |
| 2023/0000669 A1 | 1/2023 | Babkin et al. |
| 2023/0028322 A1 | 1/2023 | Velis et al. |
| 2023/0031549 A1 | 2/2023 | Velis et al. |
| 2023/0046154 A1 | 2/2023 | Mazor et al. |
| 2023/0046673 A1 | 2/2023 | Velis et al. |
| 2023/0054472 A1 | 2/2023 | Hill et al. |
| 2023/0069123 A1 | 3/2023 | Soykan et al. |
| 2023/0218433 A1 | 7/2023 | Gonzales et al. |
| 2023/0240887 A1 | 8/2023 | Gonzales et al. |
| 2024/0341831 A1 | 10/2024 | Kannan et al. |

FOREIGN PATENT DOCUMENTS

| | | |
|---|---|---|
| AU | 2020272238 A1 | 10/2021 |
| AU | 2020412601 A1 | 7/2022 |
| AU | 2021324991 A1 | 3/2023 |
| CA | 3023821 | 11/2017 |
| CA | 3044020 A1 | 7/2018 |
| CA | 3065606 A1 | 9/2018 |
| CA | 3115260 A1 | 4/2020 |
| CA | 3135707 A1 | 10/2020 |
| CA | 3162660 A1 | 7/2021 |
| CN | 108836619 A | 11/2018 |
| EP | 1890627 B1 | 6/2012 |
| EP | 2111172 B1 | 10/2013 |
| EP | 2094328 B1 | 8/2014 |
| EP | 2676623 B1 | 9/2015 |

(56) References Cited

FOREIGN PATENT DOCUMENTS

| | | |
|---|---|---|
| EP | 2162083 B1 | 12/2015 |
| EP | 2499984 B1 | 1/2016 |
| EP | 2967706 A1 | 1/2016 |
| EP | 2687174 B1 | 10/2016 |
| EP | 3099258 A1 | 12/2016 |
| EP | 3099260 A2 | 12/2016 |
| EP | 3182918 A1 | 6/2017 |
| EP | 2802279 B1 | 8/2017 |
| EP | 3104796 B | 4/2019 |
| EP | 3488833 A1 | 5/2019 |
| EP | 3541345 A1 | 9/2019 |
| EP | 3342379 B1 | 10/2019 |
| EP | 3506846 A4 | 1/2021 |
| EP | 3099262 B1 | 2/2022 |
| EP | 4081746 A1 | 11/2022 |
| GB | 2423023 B | 10/2009 |
| HK | 40011648 A | 7/2020 |
| IL | 266662 A | 6/2019 |
| IL | 269038 A | 10/2019 |
| JP | H01223961 A | 9/1989 |
| JP | 2022126649 A | 8/2022 |
| MX | 2019010396 A | 7/2020 |
| SG | 11201908076 TA | 9/2019 |
| SG | 11202103368 XA | 4/2021 |
| SG | 11202103636 TA | 5/2021 |
| WO | 9744092 A1 | 11/1997 |
| WO | 9903411 A1 | 1/1999 |
| WO | 2003078596 A2 | 9/2003 |
| WO | 2007101039 A1 | 9/2007 |
| WO | 2007127924 A2 | 11/2007 |
| WO | 2007133839 A1 | 11/2007 |
| WO | 2008016730 A2 | 2/2008 |
| WO | 2008039556 A1 | 4/2008 |
| WO | 2008039557 A1 | 4/2008 |
| WO | 2008055243 A2 | 5/2008 |
| WO | 2008060423 A2 | 5/2008 |
| WO | 2008143678 A1 | 11/2008 |
| WO | 2009011708 A1 | 1/2009 |
| WO | 2009026471 A1 | 2/2009 |
| WO | 2010036732 A1 | 4/2010 |
| WO | 2010127315 A2 | 11/2010 |
| WO | 2011091293 A1 | 7/2011 |
| WO | 2011091431 A1 | 7/2011 |
| WO | 2012012296 A1 | 1/2012 |
| WO | 2012103242 A1 | 8/2012 |
| WO | 2012103315 A2 | 8/2012 |
| WO | 2014151850 A2 | 9/2014 |
| WO | 2014151872 A2 | 9/2014 |
| WO | 2016033384 A1 | 3/2016 |
| WO | 2017223417 A1 | 12/2017 |
| WO | 2018044825 A1 | 3/2018 |
| WO | 2019046236 A2 | 3/2019 |
| WO | 2020142519 A1 | 7/2020 |
| WO | 2022169699 A1 | 8/2022 |
| WO | 2022229277 A1 | 11/2022 |
| WO | 2023278891 A1 | 1/2023 |
| WO | 2023064528 A1 | 4/2023 |

OTHER PUBLICATIONS

Coleman, S.R. et al., "Clinical Efficacy of Noninvasive Cryolipolysis and Its Effects on Peripheral Nerves." Aesth. Plast. Surg., 33: 482-488 (2009).
Day et al., "Popsicle Panniculitis." Pediatric Emergency Care; 8(2); 91-93, Apr. 1992.
Epstein et al.; Popsicle Panniculitis; NEJM; 282(17); 966-9867; Apr. 23, 1070.
Extended European Search Report mailed Apr. 9, 2018 in European Patent Application No. 15846755.5, 9 pages.
Extended European Search Report mailed Aug. 19, 2022 in European Patent Application No. 19907538.3, 8 pages.
Extended European Search Report mailed Dec. 15, 2023 in European Patent Application No. 21756850.0, 8 pages.
Gage et al., "Critical temperature for skin necrosis in experimental cryosurgery." Cryobiology; 19(3); 273-282, Jun. 1982.
International Search Report mailed Dec. 28, 2015 in International Patent Application No. PCT/US15/51903, 10 pages.
International Search Report mailed Jun. 29, 2021 in International Patent Application No. PCT/US21/18926, 12 pages.
International Search Report mailed Jun. 6, 2023 in International Patent Application No. PCT/US22/82620, 11 pages.
International Search Report mailed May 1, 2020 in International Patent Application No. PCT/US19/69113, 11 pages.
International Search Report mailed May 16, 2012 in International Patent Application No. PCT/US12/22697.
Kim et al., "Tongue fat and its relationship to obstructive sleep apnea." Sleep 37(10); 1638-1648, Oct. 2014.
MedicalXpress: "Study shows that tongue seize and fat may predict sleep apnea risk in obese adults." 3 pages. Retrieved from the internet on Nov. 27, 2018 at <https://medicalxpress.com/news/2014-09-tongue-size-fat-apnea-obese.html>.
Nelson A.A. et al., "Cryolipolysis for Reduction of Excess Adipose Tissue." Semin. Cutan. Med. Surg., 28: 244-249 (2009).
Office Action mailed Jul. 18, 2017 in Canadian Patent Application No. 2,825,624, 3 pages.
Office Action mailed Jul. 18, 2018 in Canadian Patent Application No. 2,825,624, 4 pages.
Office Action mailed Jul. 25, 2023 in Japanese Patent Application No. 2021-538451, 7 pages, English Translation.
Office Action mailed Apr. 16, 2024 in Japanese Patent Application No. 2021-538451, 4 pages, English Translation.
Office Action mailed Oct. 27, 2021 in Canadian Patent Application No. 2,962,920, 5 pages.
Office Action mailed Sep. 13, 2023 in Canadian Patent Application No. 3,168,812, 4 pages.
Office Action mailed Sep. 22, 2023 in Canadian Patent Application No. 3,125,291, 5 pages.
Rajkumar et al., "Popsicle Panniculitis of the Cheeks." Clinical Pediatrics; 15(7); 619-621; Jul. 1976.
Zelickson, B. et al., "Cryolipolysis for Noninvasive Fat Cell Destruction: Initial Results from a Pig Model." Dermatol. Surg., 35: 1462-1470 (2009).
Chakrabarti, P. et al., "FoxO1 controls insulin-dependent adipose triglyceride lipase (ATGL) expression and lipolysis in adipocytes," Journal of biological chemistry, 2009, vol. 284, No. 20, pp. 13296-13300.
Decision of Dismissal of Amendment mailed Nov. 12, 2024 in Japanese Patent Application No. 2021-538451, 4 pages, with English Translation.
Examination Report mailed Aug. 15, 2024 in Canadian Patent Application No. 3,125,291, 5 pages.
Examination Report mailed Aug. 15, 2024 in Canadian Patent Application No. 3,168,812, 4 pages.
Examination Report mailed Jul. 10, 2024 in European Patent Application No. 19907538.3, 4 pages.
Examination Report mailed Sep. 16, 2024 in Australian Patent Application No. 2019419502, 4 pages.
Ichioka, M. et al., "Increased expression of macrophage-inducible C-type lectin in adipose tissue of obese mice and humans," Diabetes, 2011, vol. 60, pp. 819-826.
International Search Report and Written Opinion mailed Jan. 31, 2025 in International Patent Application No. PCT/US24/51836, 10 pages.
Keuper, M. et al., "An inflammatory micro-environment promotes human adipocyte apoptosis," Molecular and cellular endocrinology, 2011, vol. 339, pp. 105-113.
Tanaka, M. et al., "Macrophage-inducible C-type lectin underlies obesity-induced adipose tissue fibrosis," Nature communications, 2014, vol. 5, article:4982, pp. 1-13.

\* cited by examiner

| | Mandibular arch dimension | Females, n=101 Mean (SD) | CV | Males, n=113 Mean (SD) | CV | T value |
|---|---|---|---|---|---|---|
| a | Inter-canine distance | 25.20 (1.69) | 6.71 | 25.43 (1.51) | 5.93 | 0.93 |
| b | Inter-first molar distance | 42.91 (2.45) | 5.70 | 45.07 (2.28) | 5.06 | 5.91* |
| c | Inter-second molar distance | 50.22 (2.71) | 5.40 | 55.34 (2.97) | 5.37 | 7.07* |
| d | Anterior arch length | 4.70 (1.27) | 26.94 | 5.46 (0.74) | 13.57 | 4.74* |
| e | Molar arch length | 24.78 (2.12) | 8.55 | 25.06 (1.93) | 7.70 | 0.90 |
| f | Total arch length | 38.36 (2.73) | 7.12 | 38.37 (2.22) | 5.79 | 0.02 |

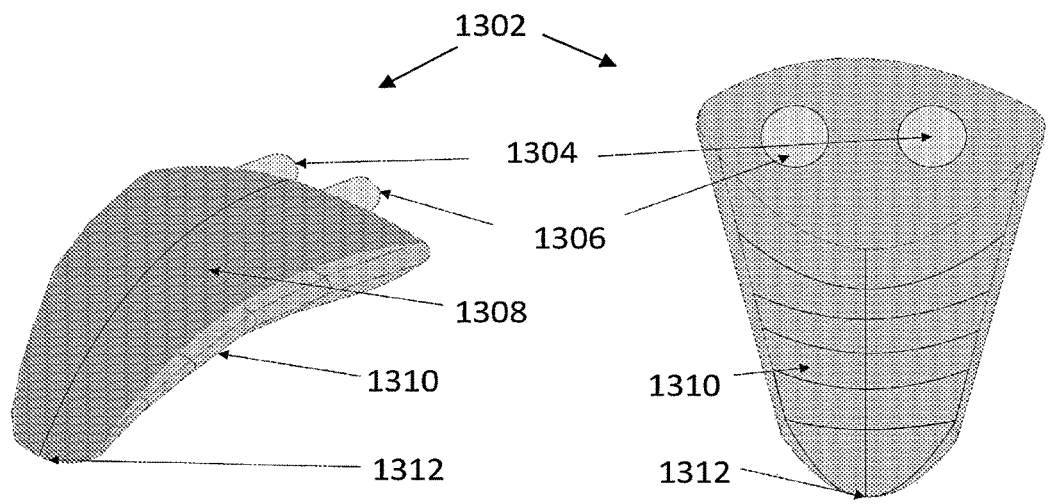
FIG. 13A  FIG. 13B
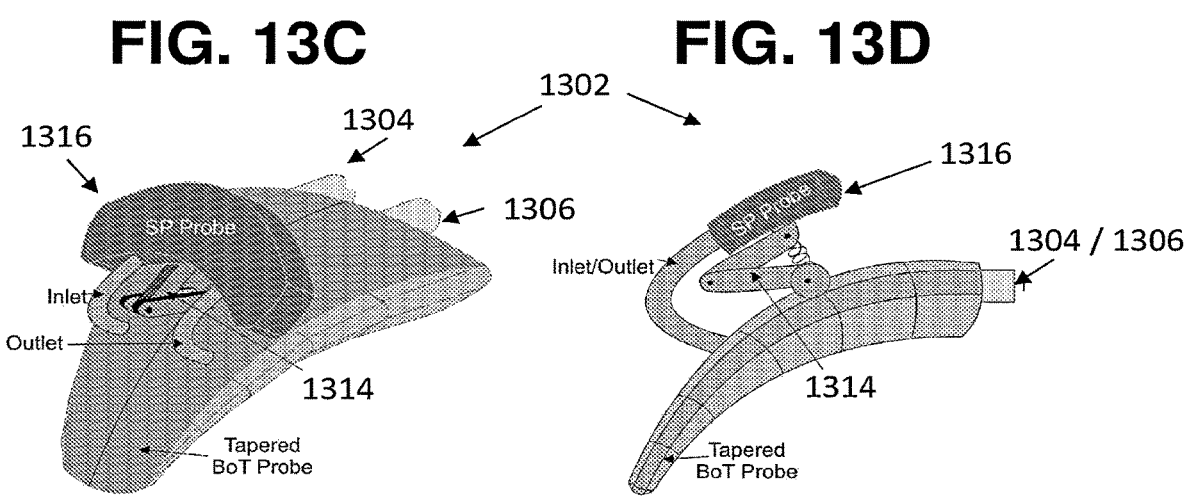
FIG. 13C  FIG. 13D

SYSTEMS AND METHODS FOR TREATMENT OF OBSTRUCTIVE SLEEP APNEA

PRIORITY CLAIM

This patent application is a bypass continuation of International Patent Application No. PCT/US22/82620, filed on Dec. 30, 2022, which claims priority to U.S. provisional patent application No. 63/295,416, titled "SYSTEMS AND METHODS FOR TREATMENT OF OBSTRUCTIVE SLEEP APNEA" and filed on Dec. 30, 2021, which are herein incorporated by reference in their entireties.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD

The present disclosure relates generally to minimally invasive treatment of obstructive sleep apnea.

BACKGROUND

Obstructive sleep apnea (OSA) is a sleep disorder that affects up to 20% of the adult population. OSA generally occurs during sleep when soft tissue enlarges and obstructs the pharyngeal airway, creating cessation of, or impeding, breathing due to the decrease in size of the upper airway, resulting in the breathing of the patient to repeatedly stop and restart. Obstruction can occur at one or more levels including the retropalatal and retrolingual areas, and if untreated could leave to the development of serious complications, including atrial fibrillation and heart failure.

This enlargement of the tongue generally occurs due to excess body weight, causing adipose tissue to accumulate within the tongue. With the accumulation of adipose tissue, organs in the oral cavity, including the tongue, become enlarged and lose their firmness and grow in volume. Due to their inability to maintain their tone and their increase in size, they move into the airway and restrict airflow. One condition that is particularly concerning occurs when there is excess fat near the base of the tongue, which is adjacent the airway.

Surgical correction (such as glossectomy) of such obstructions remains a challenge, specifically for the retrolingual area. Removal or ablation of tongue tissue has been utilized with poor results due to complications, such as severe bleeding, abscess formation, and/or the inability to move the tongue anterior enough to relieve the obstruction. Medical devices such as tongue trainers also result in limited mobility or inconvenience to the patient.

Continuous positive airway pressure (CPAP) is a more noninvasive technique in relieving OSA than surgical operation, but is a remedy and not a permanent solution. Applying a stream of compressed air through the pharyngeal airway to overcome the collapsing soft tissue results in the patient being uncomfortable and fully dependent on the machine and its limitations, such as a stuffy nose, claustrophobia, skin irritation, pressure sores, and dry mouth. Additionally, the mechanics of the machine result in the CPAP mask possibly falling off during sleep, bothersome noises, and a leaky mask, all while being costly and electrically dependent. These factors lead to the patient having trouble falling asleep, demonstrating a faulty solution to curing OSA, since the patient will never be cured of their disease and will still have complications during sleep.

Adipose cryolysis is the use of cold to selectively target the submucosal adipose tissue, leading to a reduction in tissue volume via the removal of effected fat cells. However, it is known that the effect of cold on cells depend on various factors, including the cell type, duration that the cells are exposed to cold, rate of cooling and warming, as well as the number of cooling and warming cycles. When the adipocytes are exposed to temperatures below $-15°$ C., necrosis occurs. At temperatures around $-10°$ C., adipocytes are forced into a pathway that is reminiscent of apoptosis. When the temperatures are in the range of $-5°$ C. to $+10°$ C., cells may move into a hyper-metabolic state, resulting in thermogenesis, which may also reduce the lipid volumes, or result in adipocyte cell death.

Above observations may indicate that the exposure to temperatures in the range of $+5°$ C. to $-15°$ C. for 1-100 minutes may cause maximum damage to the adipose tissue while minimizing the damage to muscle. Furthermore, even when the 70-80% of the skeletal muscle is damaged, muscle does recover within few days, thanks to its regenerative capacity. These facts can be used during the design of the devices that can be used for the selective elimination of the adipose tissue while preserving the other types of tissues such as the skeletal muscle, blood vessels and the nerves.

The removal of adipocyte tissue (fat) from the tongue is expected to reduce the volume of tissue in the oropharynx, and the reduction of this tissue is known to cure or reduce the severity of obstructive sleep apnea, as demonstrated by the clinical outcomes of other procedures, such as the glossectomy of the tongue and the mandibular advancement. Furthermore, the removal of the fat from within key tongue muscles, such as the genioglossus muscle, will improve the ability of these muscle groups to function, which in turn may result in the reduction of obstructive sleep apnea. These muscles do keep the tongue from falling back into the airway, in both their activated and passive states. Adipose tissue that is interspersed within the muscle act as a restriction to the muscle due to the mass and inability of the adipose tissue to move in the same manner as the adjacent muscle fibers.

To date, however, cryolitic treatment of OSA has involved procedures analogous to ablation, merely substituting cryolitic cold for electrolytic heat and non-selectively destroying all tissues in a similar manner—and with the same complications as the non-cryolitic therapies.

It is known that patients with OSA have a higher percentage of adipose deposits in the areas of obstruction, specifically, the soft palate and uvula, base of tongue and lateral pharyngeal walls. The adipose tissue may be up to or greater than 40% of the total volume of tissues in these areas. Removal of the fat deposits in these areas would permit relief from OSA symptoms while preserving surrounding tissue. To date, however, cryolitic treatment of OSA has involved procedures analogous to ablation, merely substituting cryolitic cold for electrolytic heat and nonselectively destroying tissue in a similar manner—and with the same complications.

Technologies that are used for the treatment of obstructive sleep apnea range from non-invasive ones such as continuous positive air pressure (CPAP), to surgical modifications such as glossectomy where the part of the tongue is removed, to medical devices such as tongue trainers. Unfortunately, many of these technologies either provide limited results or create much inconvenience to the patients. Hence, there is an unmet medical need to build a minimally invasive technique for the treatment of the patients with obstructive sleep apnea.

SUMMARY OF THE DISCLOSURE

The present invention employs adipose cryolysis in a tissue-selective manner by selectively removing fat cells from the tissues responsible for the OSA, such as the oropharyngeal tissues, and exploits the fact that adipocytes have a heightened to susceptibility to cooling compared to other types of cells, resulting in the slow and steady digestion of the effected tissues by the surrounding macrophages. Related systems, methods of use, and design parameters are provided herein.

In various embodiments, this disclosure exploits the particular cryolitic vulnerability of adipose tissue to provide a medical device to treat OSA without damaging and/or reducing the function of oropharyngeal tissue. Certain embodiments of the medical device may include engagement members that are formed in the shape of each specific area to be cooled, or are configured to cool multiple organs at once. Some embodiments may utilize grasping portions configured to grasp or pinch targeted anatomical structures, such as the soft palate, base of the tongue and the soft tissues of the pharynx, which are known to be associated with OSA, thereby cooling the tissue between the grasping portions and ensuring good mechanical contact during cooling. In some embodiments, the medical device may pierce the mucosa to cool the underlying tissues. The medical device may also be configured to inject a cooling agent into the underlying tissue to reduce the temperature of the deeper tissues. Additionally, the medical device may include engagement members configured to pierce the lower submaxillary triangle in order to reach more inaccessible areas of the adipose tissue on the lower tongue.

According to one embodiment, a system for treatment of obstructive sleep apnea is provided, comprising a source of cooling fluid, an applicator configured to receive the cooling fluid, the applicator being sized, shaped, and configured to contact a first side of a soft palate of a patient, an insulator sized, shaped, and configured to contact a second side of the soft palate opposite the first side, the insulator being configured to protect tissues beyond the soft palate from cryo therapy, an adjustment mechanism configured to allow translation of the applicator relative to the insulator so as to capture the soft palate between the applicator and the insulator, and wherein the applicator and source of cooling fluid are configured to cooperatively cause cooling of the soft palate when placed in contact with the soft palate, the applicator being configured to be cooled to a temperature sufficient to cause cryolysis of adipose tissue within the soft palate.

In some embodiments, the insulator is disposed on an insulator holder coupled to the adjustment mechanism.

In one example, the system includes a first shaft coupling the applicator to the adjustment mechanism and a second shaft coupling the insulator to the adjustment mechanism.

In some examples, the adjustment mechanism is further configured to allow for upwards, downwards, and axial translation of the applicator and the insulator.

In one embodiment, the applicator is coupled to the first shaft via a hinge that allows for articulation of the applicator relative to the soft palate.

A method is provided, comprising placing an insulator on a first surface of a soft palate of a subject with obstructive sleep apnea, placing a cryo applicator on a second surface of the soft palate opposite the first side to capture the soft palate between the cryo applicator and the insulator, and cooling the soft palate or the underlying tissue with the cryo applicator for a time sufficient to cause cryolysis of adipose tissue within the soft palate while preventing damage to tissues outside of the soft palate with the insulator.

In some examples, cooling the second surface reduces a volume of the adipose tissue within the soft palate.

In one embodiment, the first surface comprises a surface between the soft palate and a posterior wall of the oral cavity.

In another embodiment, placing the cryo applicator further comprises adjusting a position of the cryo applicator relative to the insulator to capture the soft palate between the cryo applicator and insulator.

In some examples, the method includes monitoring a temperature of the first surface or of the insulator, and automatically stopping cooling the second A system for treatment of obstructive sleep apnea is provided, comprising a chiller configured to chill a circulating fluid, a heater configured to heat the circulating fluid, an applicator configured to receive the circulating fluid from the chiller and heater, the applicator being sized and configured to contact an oropharyngeal tissue, at least one temperature sensor adapted to sense a temperature of the oropharyngeal tissue or the applicator, at least one pump configured to move the circulating fluid from the chiller and heater into the applicator, and a controller operatively coupled to the heater, the chiller, the at least one pump, and the at least one temperature sensor, the controller being configured to adjust an operating speed of the at least one pump based on a temperature measured by the at least one temperature sensor to adjust a heat extraction rate of the applicator.

In some examples, the at least one temperature sensor is disposed on or within the applicator.

In one embodiment, the chiller comprises a first reservoir containing a cooling agent, a second reservoir containing a cryogenic agent, a first pump fluidly coupled to the first reservoir, a second pump fluidly coupled to the second reservoir, a first heat exchanger unit, a second heat exchanger unit, wherein the first pump is configured to circulate cooling agent from the first reservoir into the first heat exchanger unit and the second heat exchanger unit while the second pump is configured to circulate cryogenic agent from the second reservoir into the first heat exchanger unit and the second heat exchanger unit to cool the cryogenic agent to a target temperature.

In some examples, the first pump circulates the cooling agent through the first heat exchanger unit and second heat exchanger unit in series, while the second pump circulates the cryogenic agent through the first heat exchanger unit and second heat exchanger unit in parallel.

In some embodiments, the cooling agent is a different fluid composition than the cryogenic agent.

In one embodiment, the first heat exchanger unit comprises a first lumen configured to receive the cooling agent and a second lumen configured to receive the cryogenic agent.

In some examples, the first heat exchanger unit comprises first and second lumens configured to receive the cooling agent and a third lumen configured to receive the cryogenic agent.

In one embodiment, the first heat exchanger further comprises a thermoelectric cooler having a hot side and a cold side, wherein the first lumen contacts the hot side and the second lumen contacts the cold side.

In some embodiments, the first heat exchanger further comprises first and second thermoelectric coolers each having a hot side and a cold side, wherein the first lumen contacts the hot side of the first thermoelectric cooler, the second lumen contacts the hot side of the second thermoelectric cooler, and the third lumen contacts the cold sides of both the first and second thermoelectric coolers.

A method is provided, comprising contacting an oropharyngeal tissue with a cryo applicator, delivering a chilled circulating fluid to the cryo applicator with a pump, measuring a temperature of the cryo applicator or the oropharyngeal tissue, and adjusting an operating speed of the pump based on the measured temperature to adjust a heat extraction rate of the applicator.

A device configured for treatment of obstructive sleep apnea is provided, comprising a source of cooling fluid, an applicator configured to receive the cooling fluid, the applicator having a pair of opposing engagement members shaped to be complementary to a pair of lateral fat pads in the oropharyngeal cavity, wherein the pair of opposing engagement members are configured to be actuated to move apart from another to contact the lateral fat pads with a desired pressure, wherein the applicator and source of cooling fluid are configured to cooperatively cause cooling of the lateral fat pads when placed in contact with the lateral fat pads, the pair of opposing engagement members being configured to be cooled to a temperature sufficient to cause cryolysis of adipose tissue within the lateral fat pads.

In some embodiments, the applicator comprises a hinge configured to facilitate movement of the pair of opposing engagement members.

In some examples, the applicator comprises a scissor-like mechanism.

A device configured for treatment of obstructive sleep apnea is provided, comprising a source of cooling fluid, an applicator configured to receive the cooling fluid, the applicator having a first portion shaped and configured to contact and conform to a tongue of a patient and a second portion shaped and configured to contact and conform to a base of the tongue and extend into a vallecula without obstructing an endotracheal tube of the patient, wherein the applicator and source of cooling fluid are configured to cooperatively cause cooling of the tongue and base of the tongue when placed in contact with the tongue and base of the tongue, the engagement member being configured to be cooled to a temperature sufficient to cause cryolysis of adipose tissue within the tongue and base of the tongue.

In some embodiments, the first portion has a concavity shaped to match a concavity of the tongue and the second portion has a concavity shaped to match a concavity of the base of the tongue.

In some embodiments, the second portion tapers to a distal tip.

In one example, the first portion is approximately orthogona to the second portion.

A device configured for treatment of obstructive sleep apnea is provided, comprising a source of cooling fluid, an applicator configured to receive the cooling fluid, the applicator being sized, shaped, and configured to contact a soft palate of a patient without contacting a uvula, endotracheal tube, and teeth of the patient, wherein the applicator and source of cooling fluid are configured to cooperatively cause cooling of the soft palate when placed in contact with the soft palate, the engagement member being configured to be cooled to a temperature sufficient to cause cryolysis of adipose tissue within the soft palate.

In some examples, the applicator comprises a curved top portion shaped and configured to match a curvature of a retropalatal region of the patient.

In one embodiment, the applicator further comprises an indent on a bottom portion configured to avoid the uvula. In another embodiment, the indent has a width ranging from 5 mm to 15 mm.

In some examples, the applicator is generally horseshoe shaped.

In one example, the device further includes an articulator coupled to the applicator and configured to allow for the applicator to articulate relative to the soft palate so as to apply an even force across the soft palate.

In one example, the articulator comprises a constant force element. In some examples, the constant force element comprises a constant force spring.

BRIEF DESCRIPTIONS OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

Figure 5A:
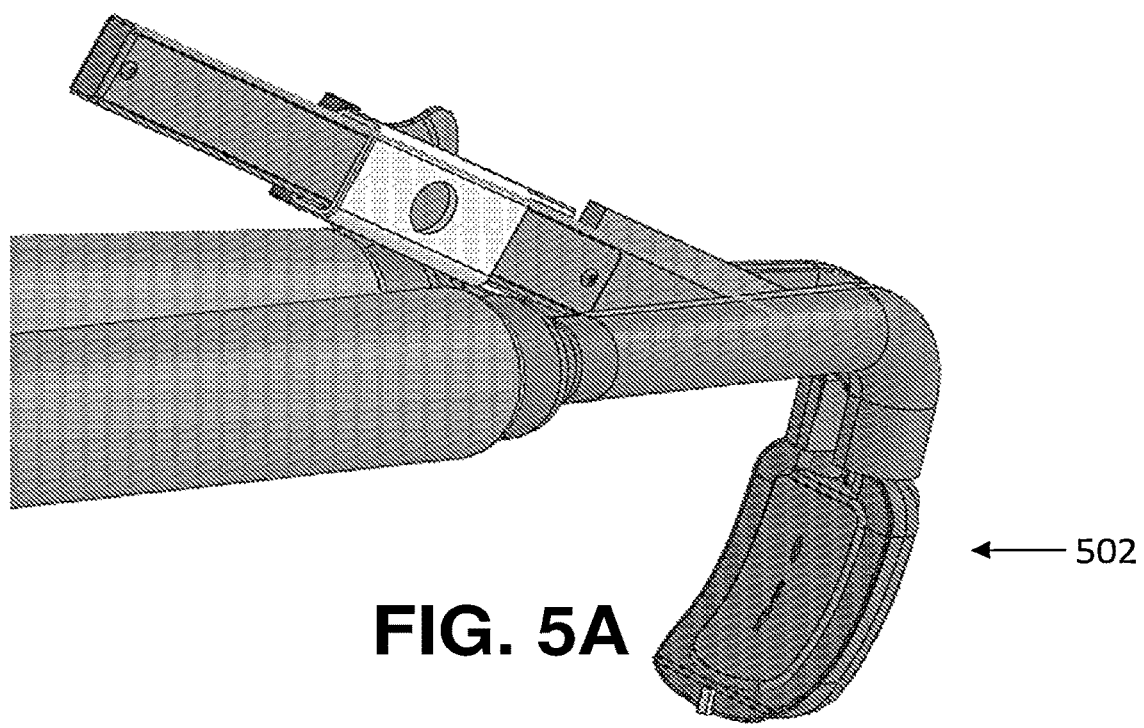
Figure 5B:
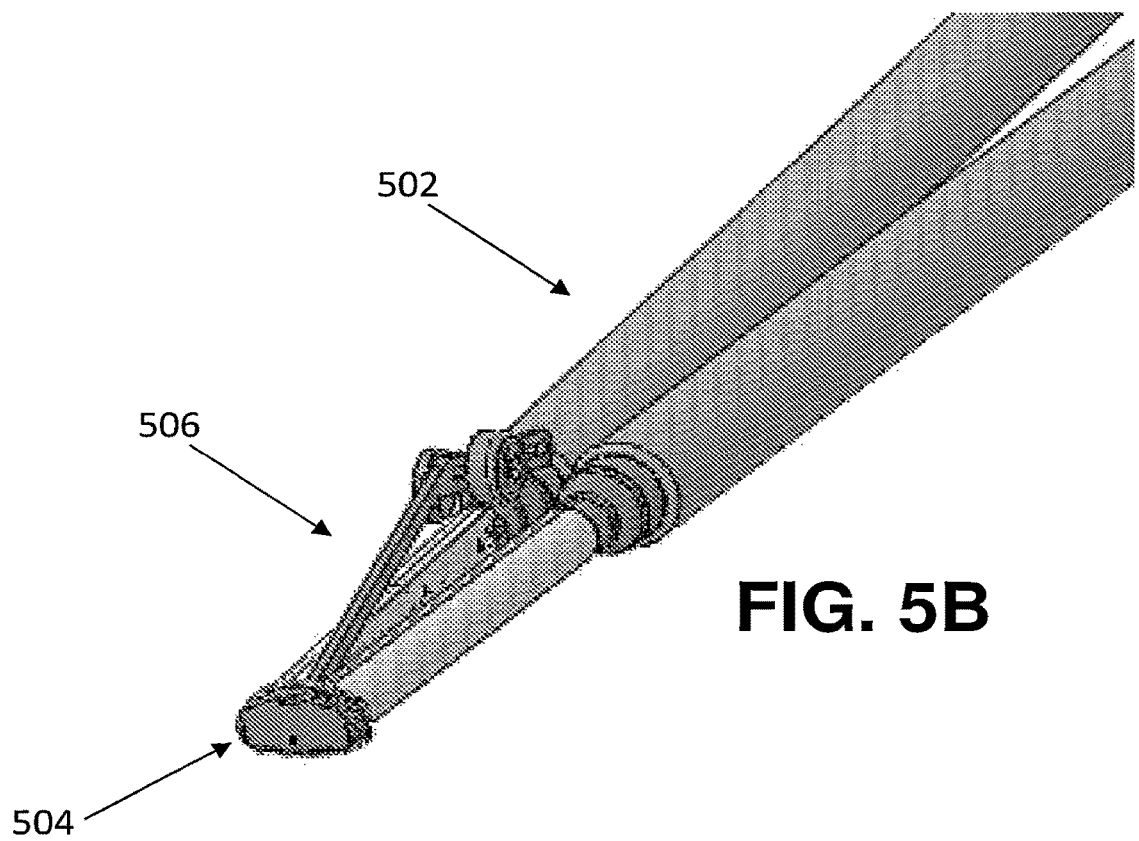
Figure 5C:
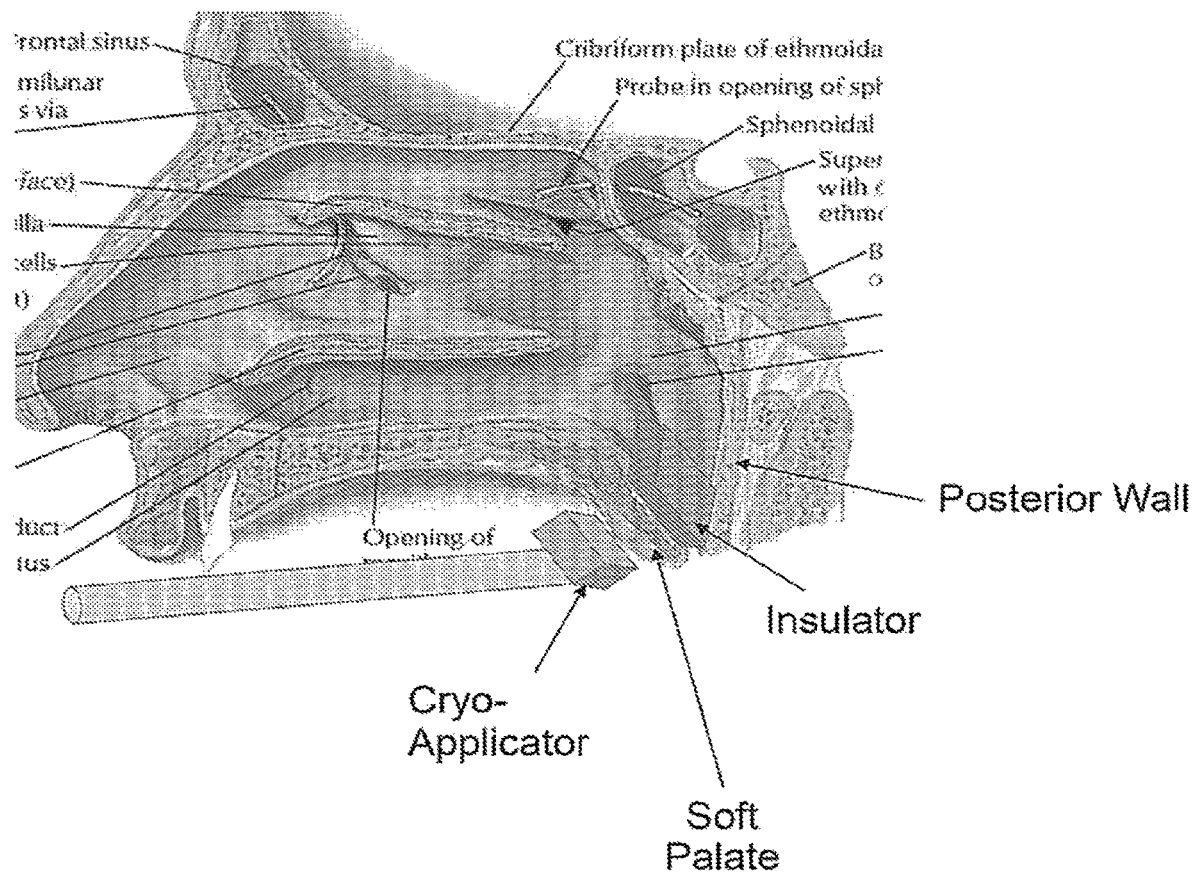
Figure 5D:
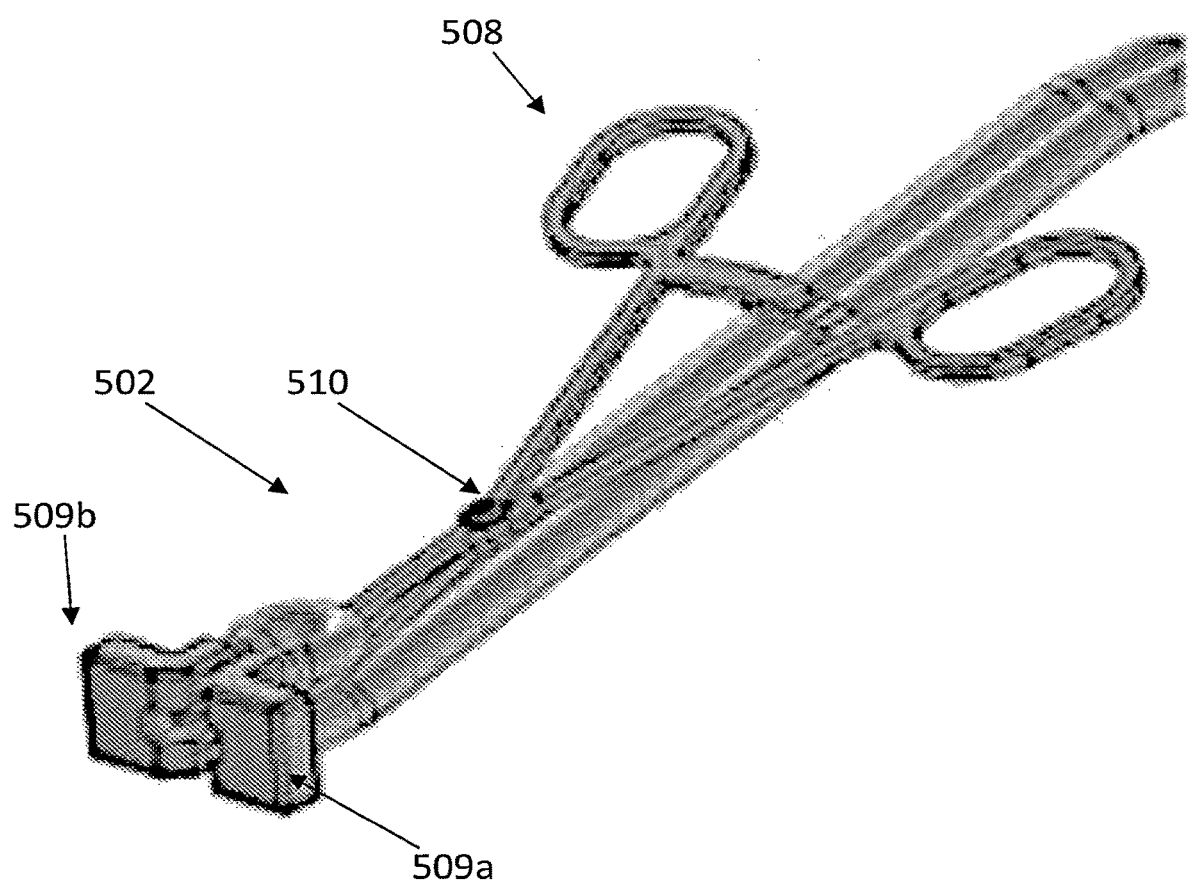

FIGS. 5A-5D illustrate various embodiments of a noninvasive Applicator that may be used to administrate coolant to different areas of the oral cavity. Specifically, FIG. 5A shows the Applicator that is designed for the treatment of the base of tongue (BoT). FIG. 5B shows the Applicator that is designed for the treatment of the soft palate. FIG. 5C shows the placement of the soft palate Applicator as well as the insulator that is designed for the thermal protection of the posterior wall. Finally, FIG. 5D shows an Applicator that is designed for the treatment of the lateral walls of the oral cavity.

Figure 6A:
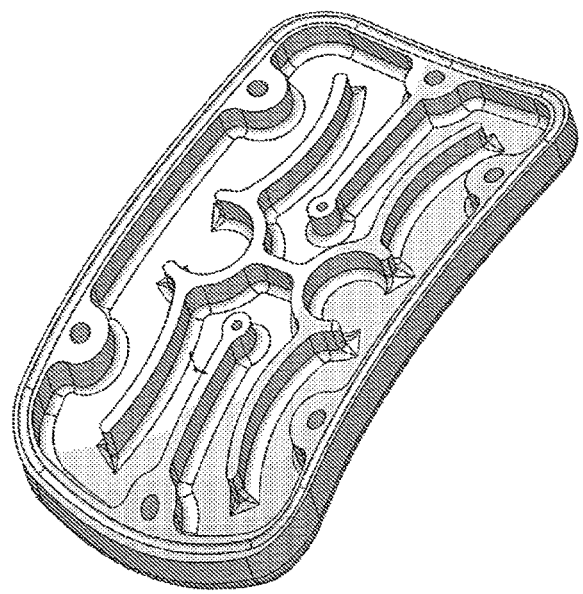
Figure 6B:
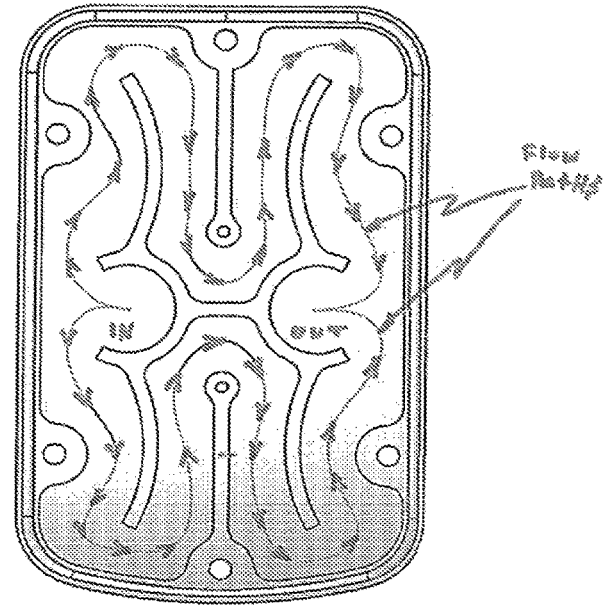

FIGS. 6A-6B illustrate one example of an Applicator with an internal flow channel.

Figure 7A:
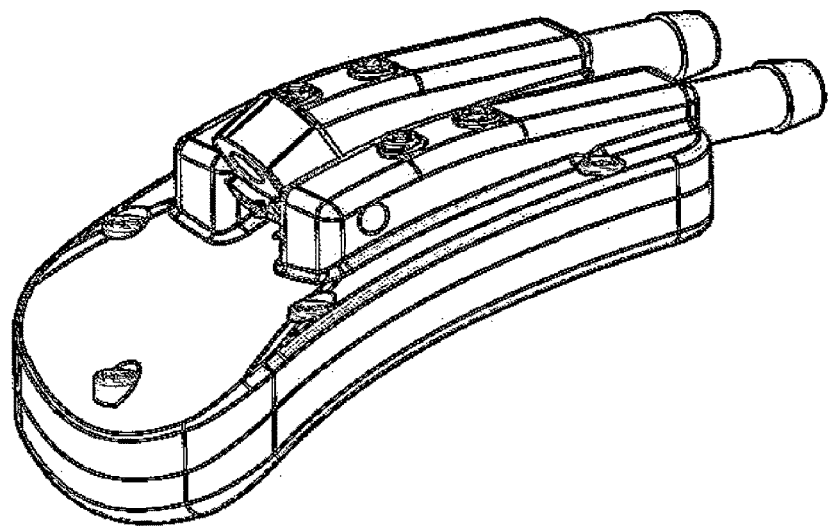
Figure 7B:
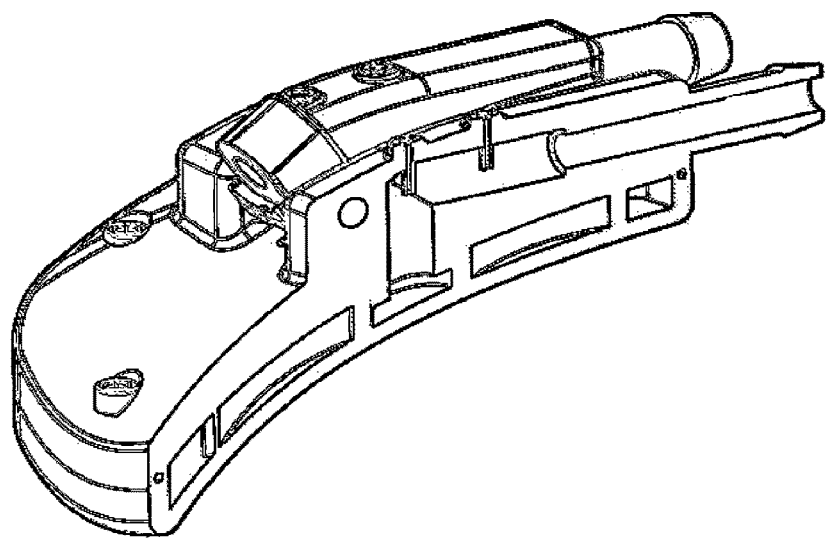

FIGS. 7A-7B illustrate an Applicator half with ports for making attachments to fluid inlet and outlet tubes.

Figure 8A:
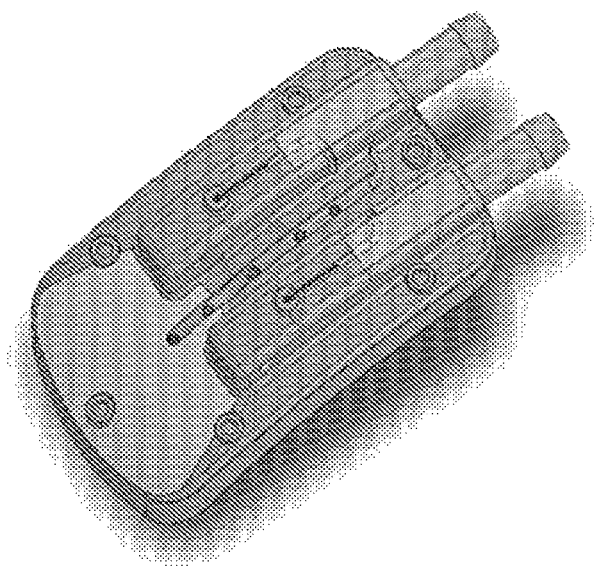
Figure 8B:
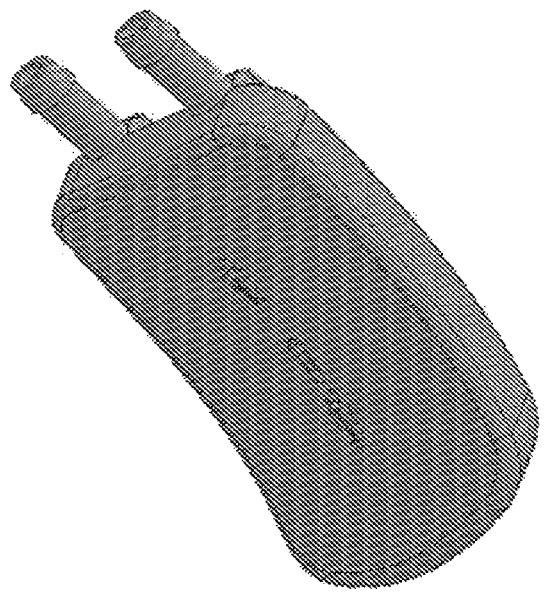

FIGS. 8A-8B illustrate an Applicator with sensors disposed on a bottom (e.g., tissue contacting) portion of the base of tongue (BoT) Applicator through multiple methods.

Figure 9:
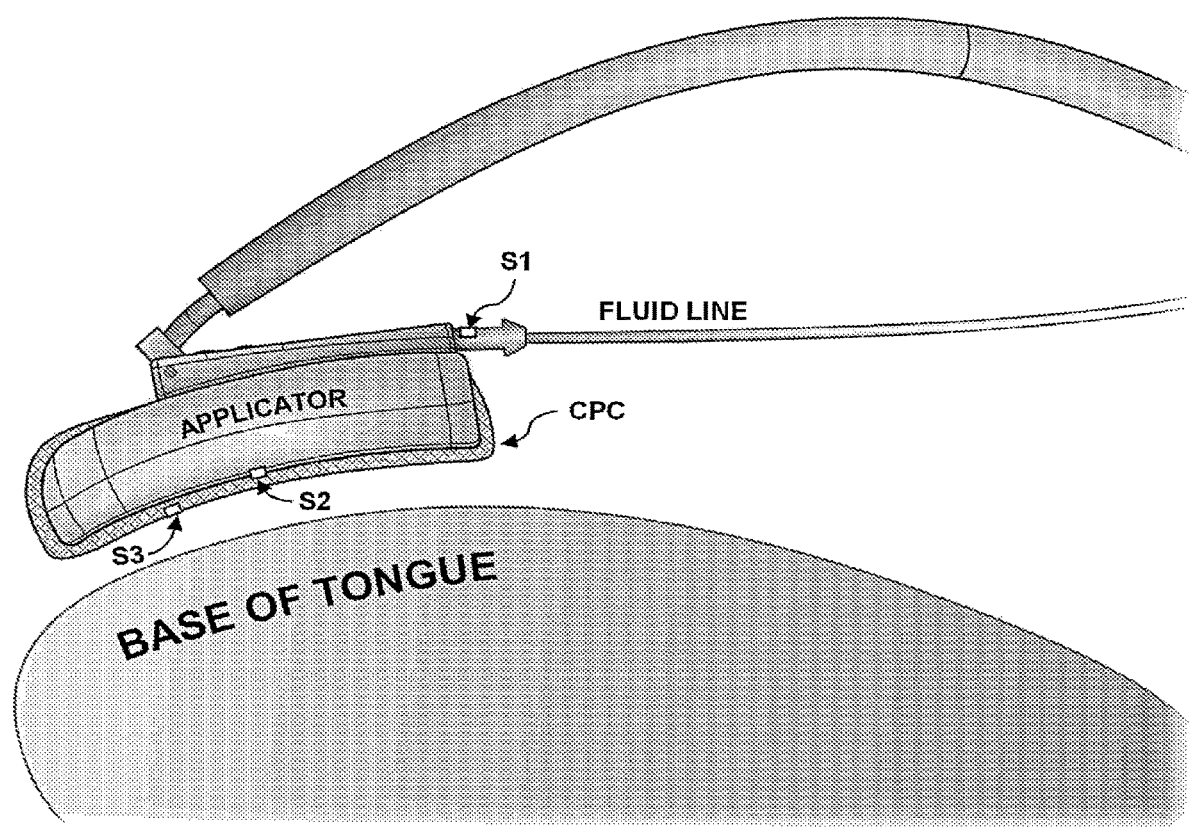

FIG. 9 shows one example of the placement of temperature sensors in and around an Applicator designed for the treatment of base of tongue.

Figure 10A:
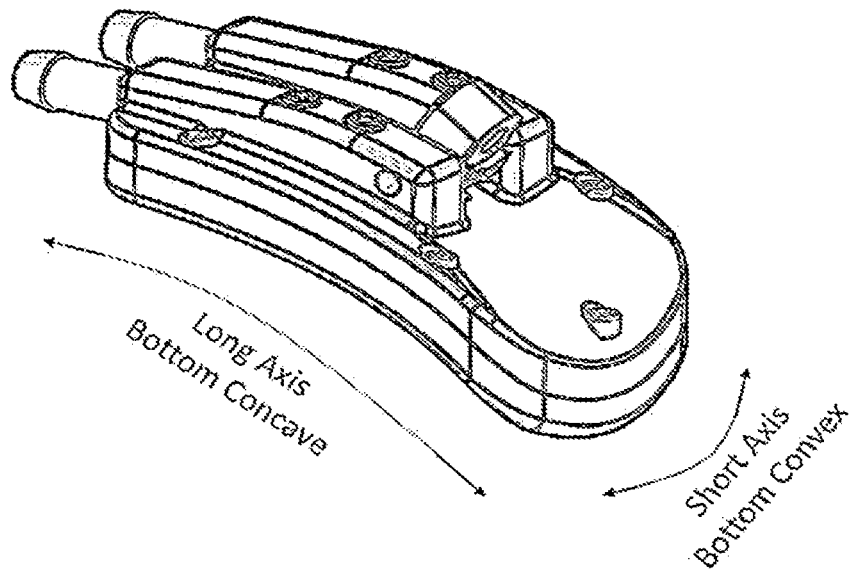
Figure 10B:
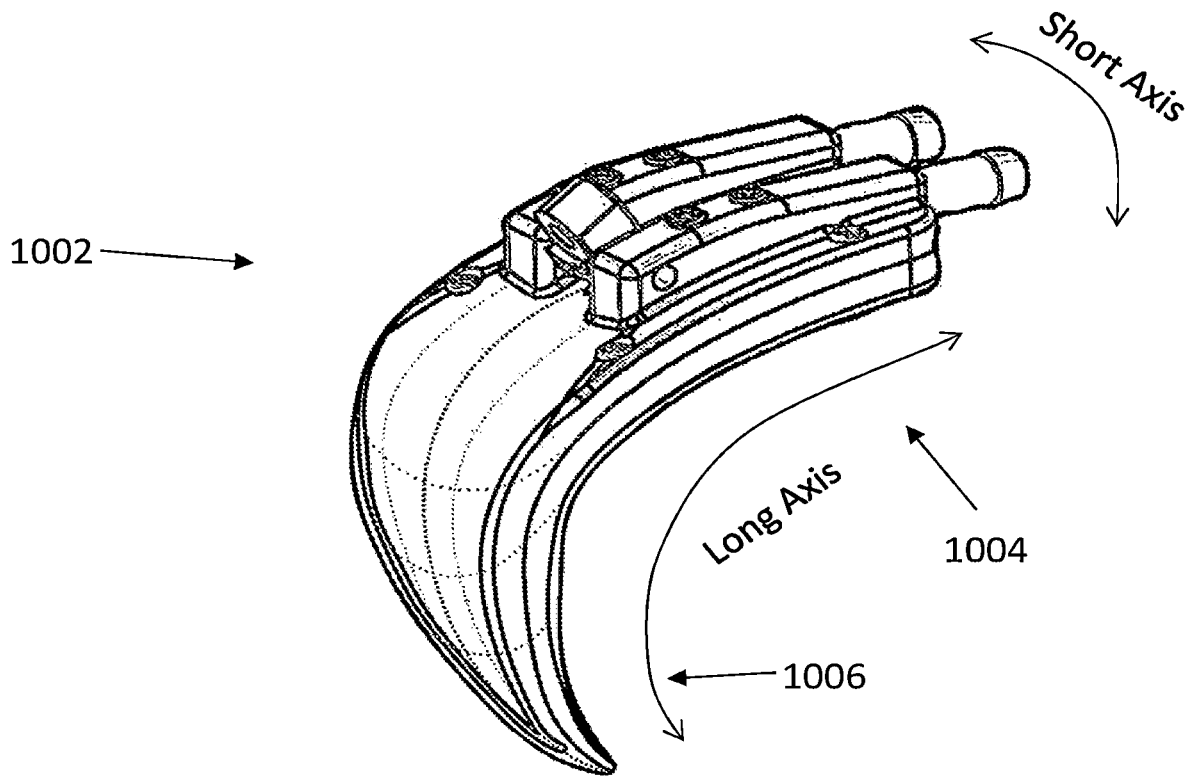

FIG. 10A-10B illustrates different embodiments of a noninvasive Applicator to treat the base of tongue (BoT).

Figure 11A:
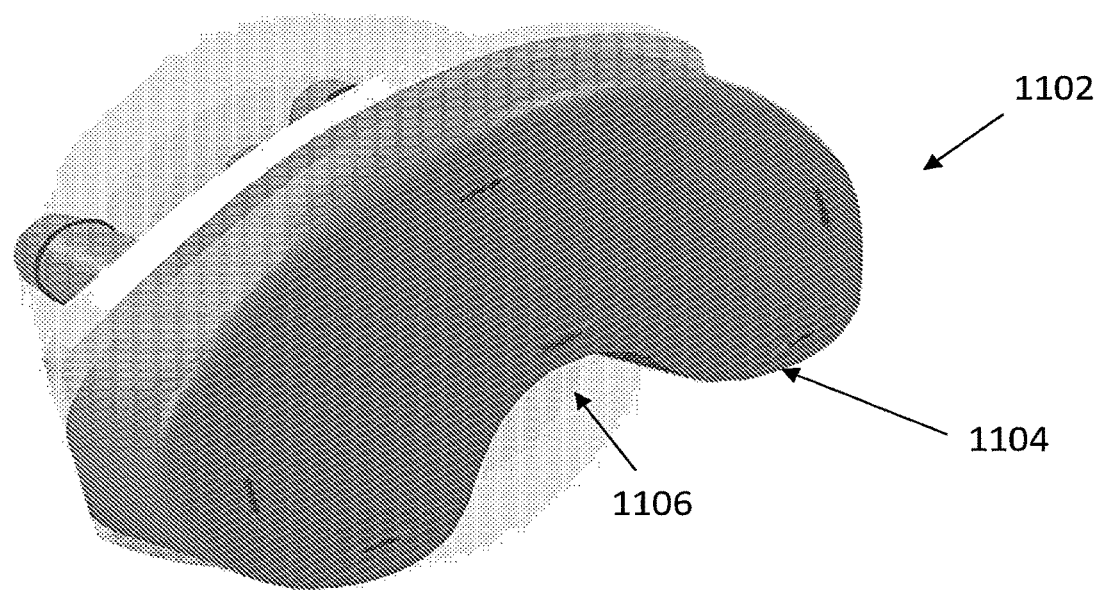
Figure 11B:
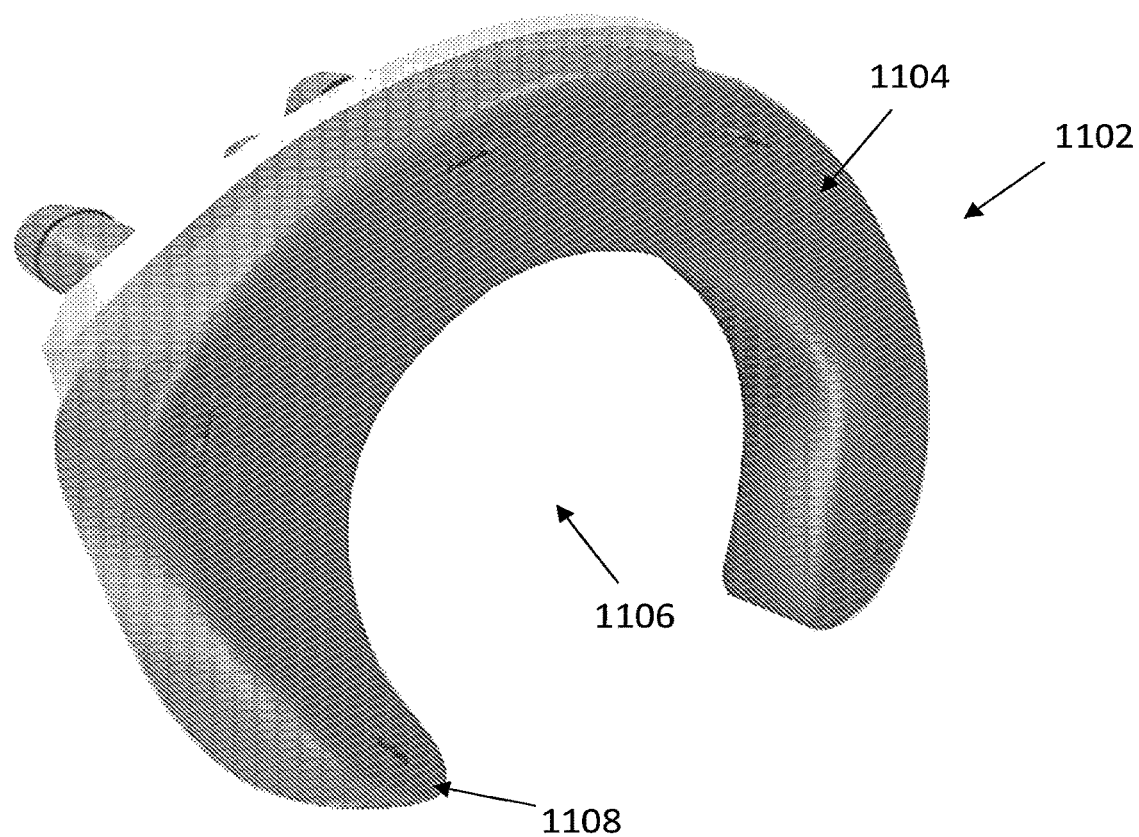
Figure 11C:
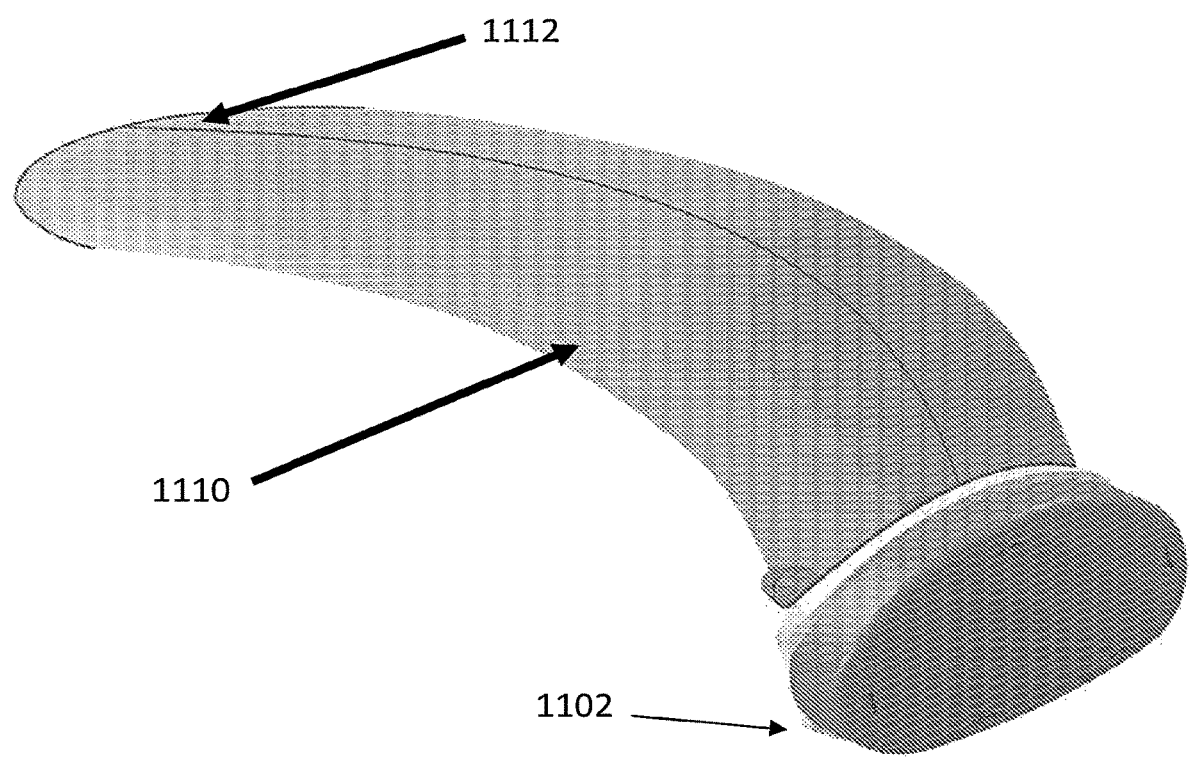

FIG. 11A-11C illustrates different embodiments of a non-invasive Applicator to treat the soft palate.

Figure 12:
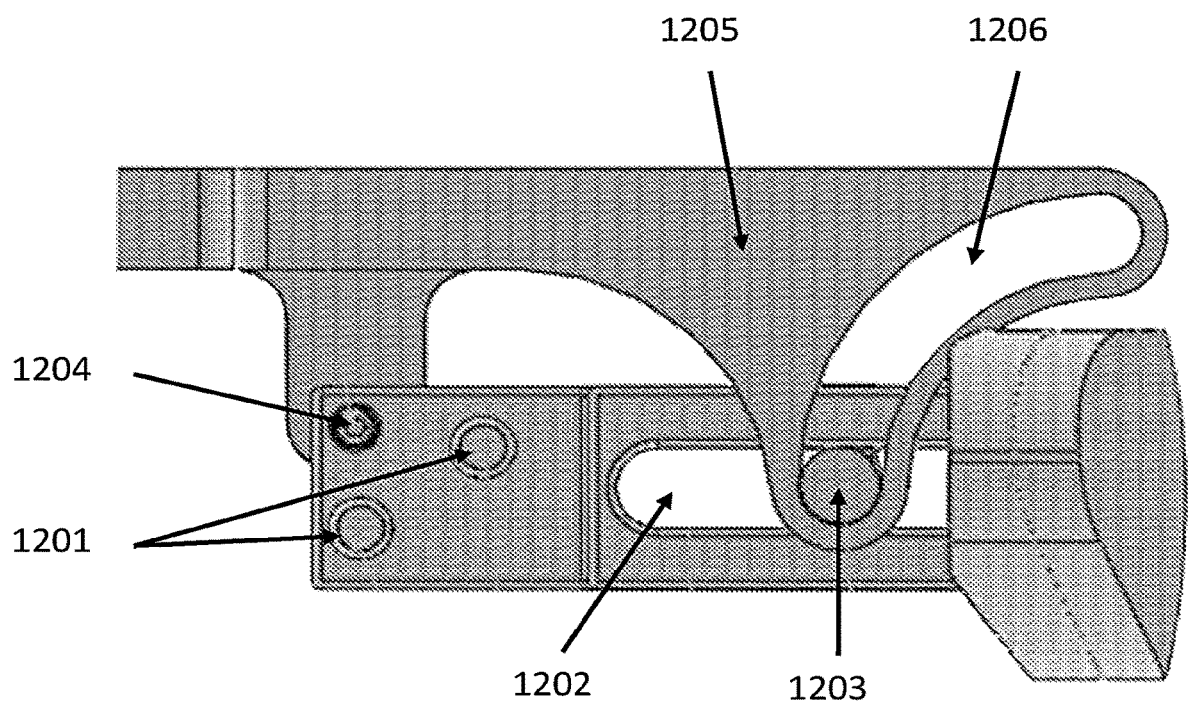

FIG. 12 illustrates multiple embodiments of a soft palate Applicator that allows articulation of the probe.

FIG. 13A-13D illustrate different embodiments of a non-invasive Applicator to treat multiple regions of the oral cavity.

Figure 14A:
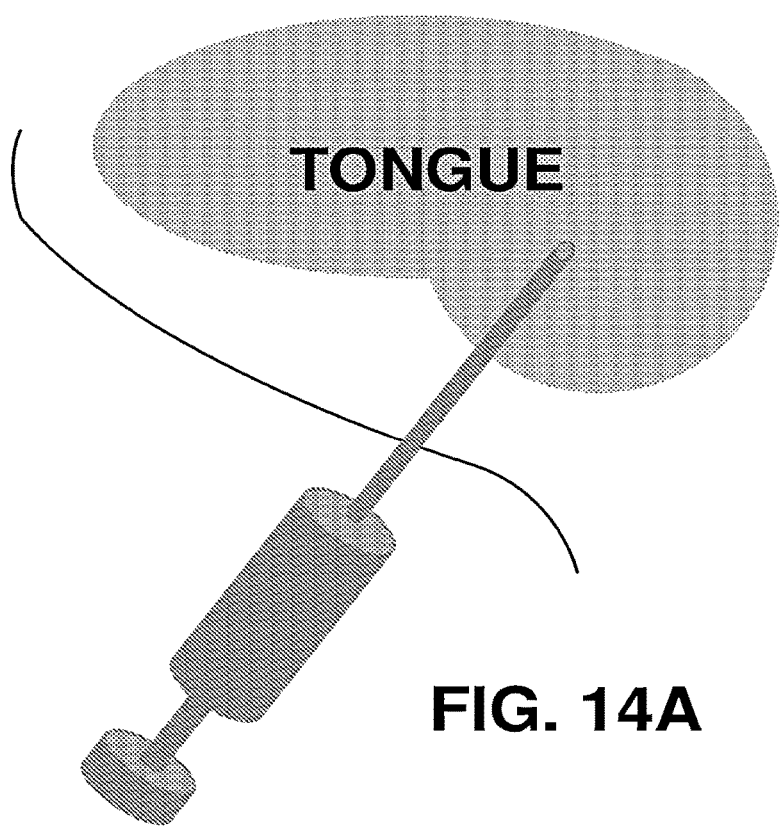
Figure 14B:
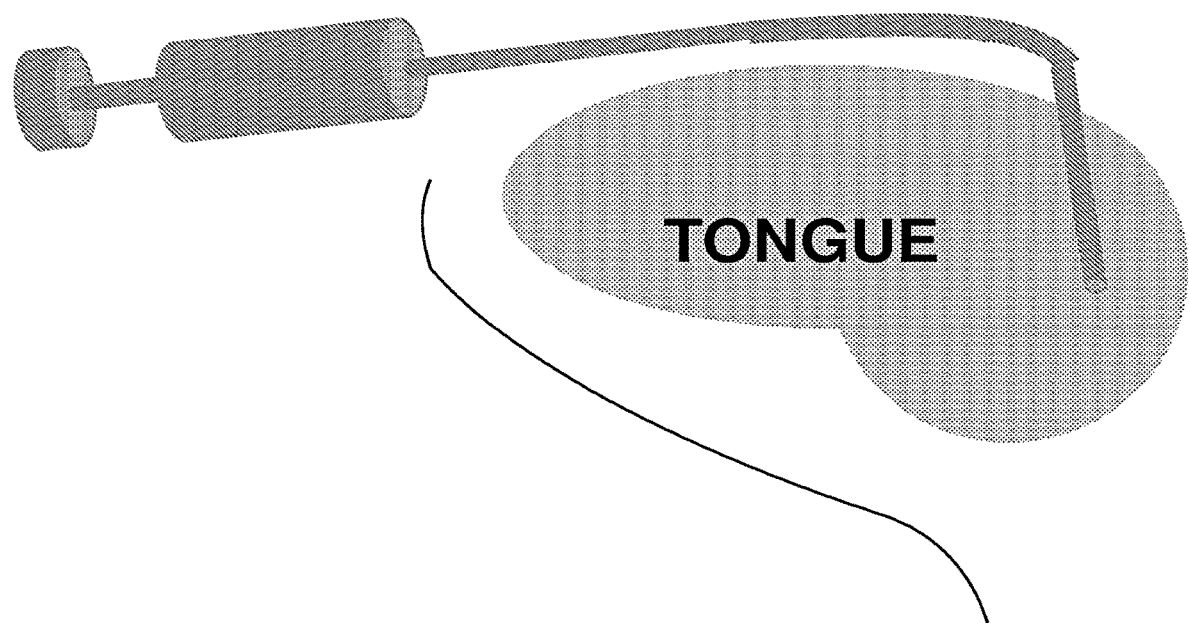

FIGS. 14A-14B illustrate various embodiments of an invasive Applicator to treat the base of tongue.

Figure 15:
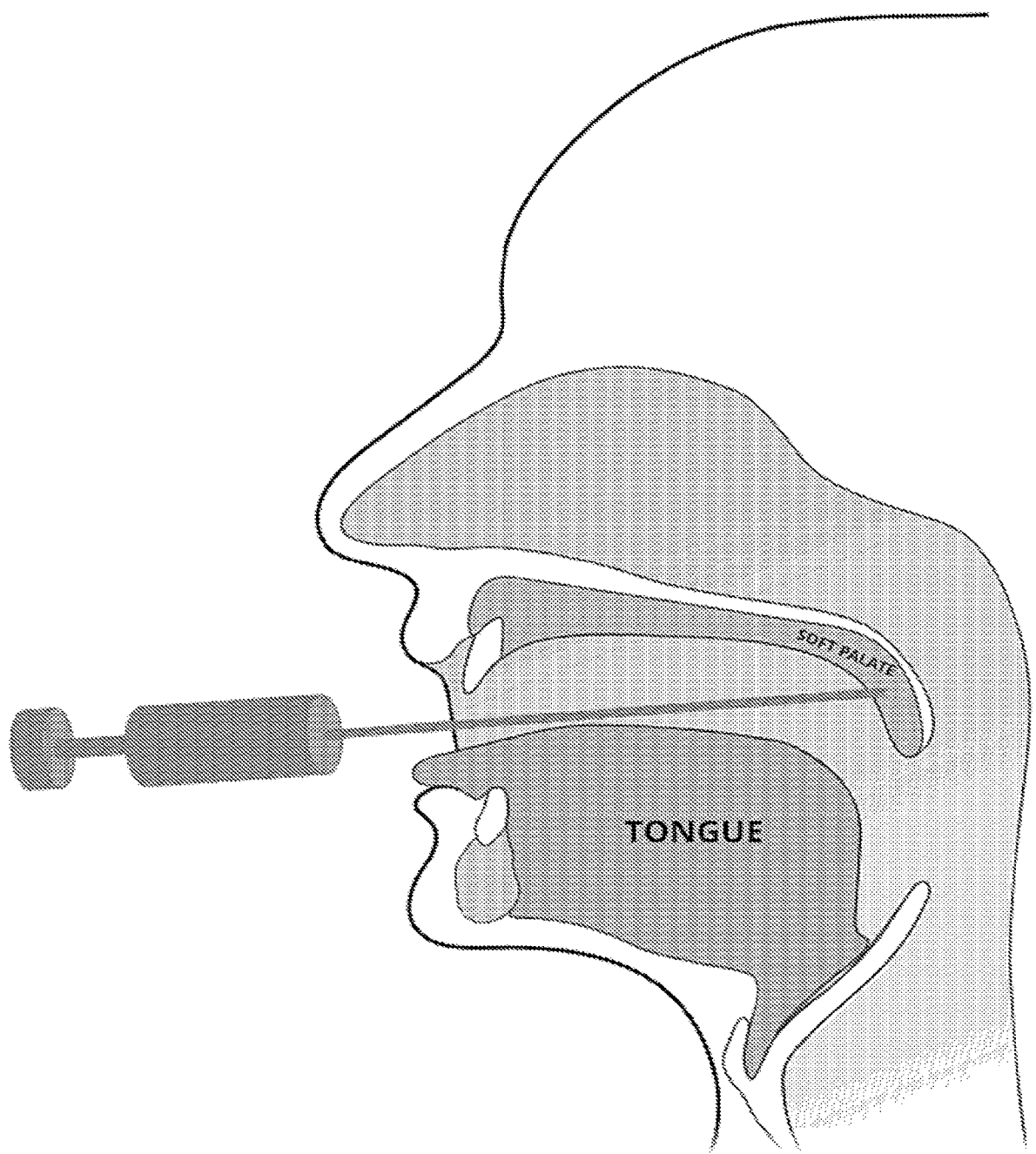

FIG. 15 illustrates one embodiment of an invasive Applicator to treat the soft palate.

Figure 16A:
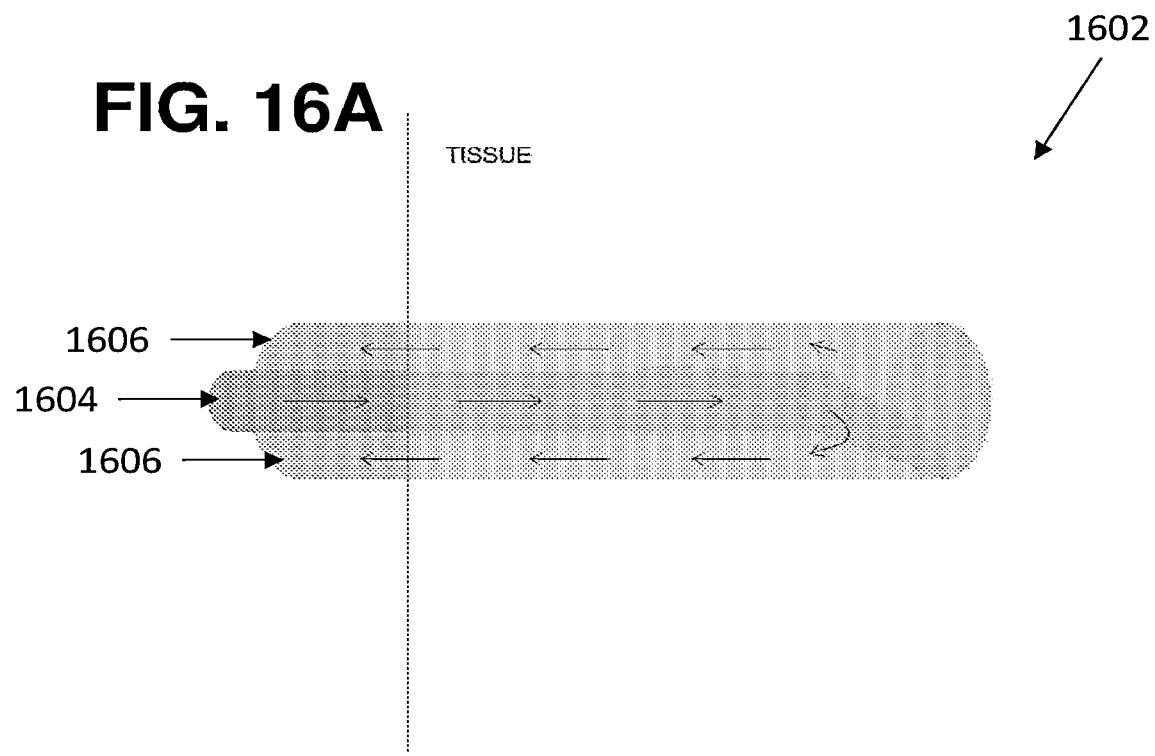
Figure 16B:
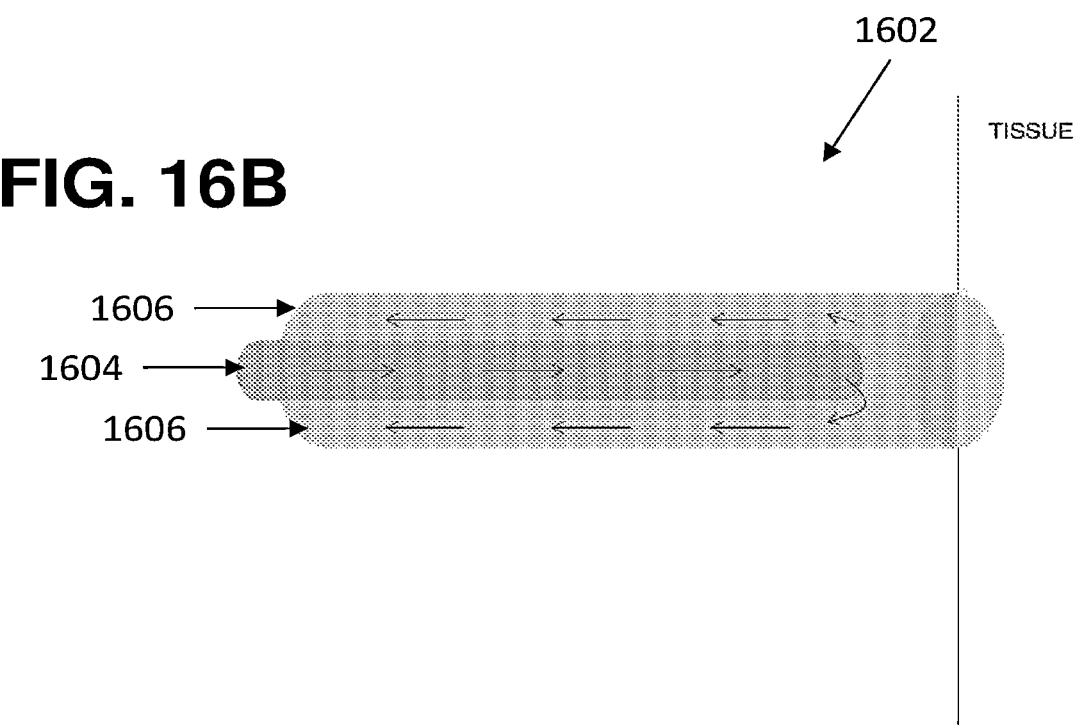

FIGS. 16A-16B illustrates different embodiments of concentric tubular probes, including penetrating and nonpenetrating probes.

Figure 17A:
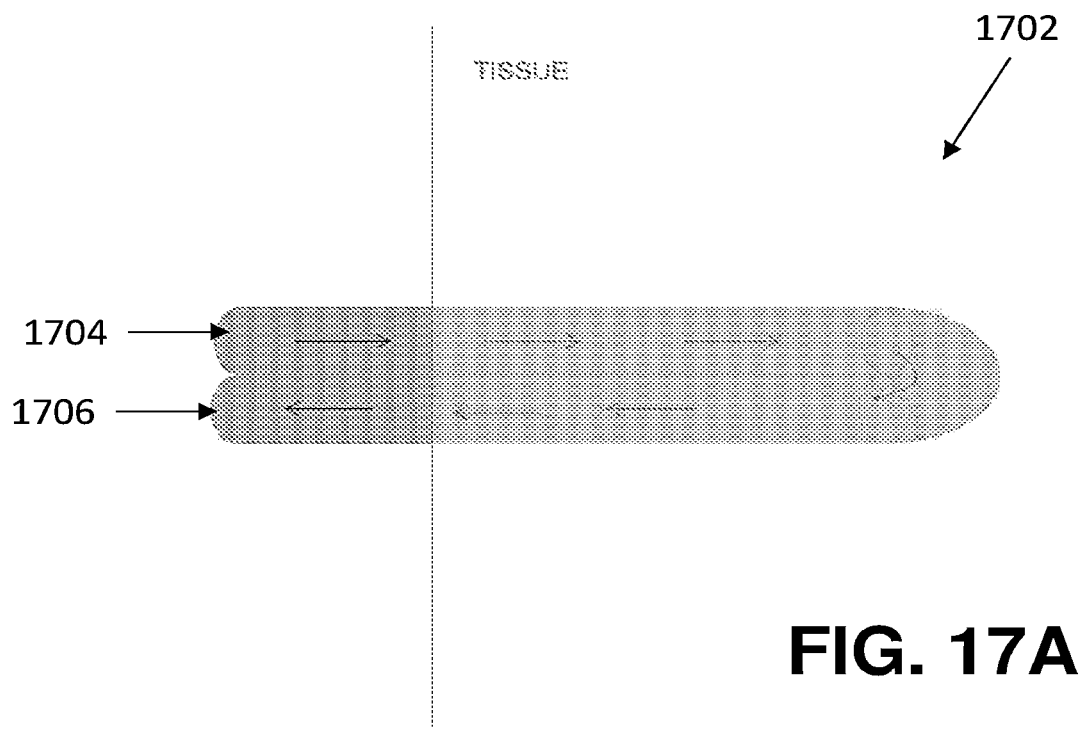
Figure 17B:
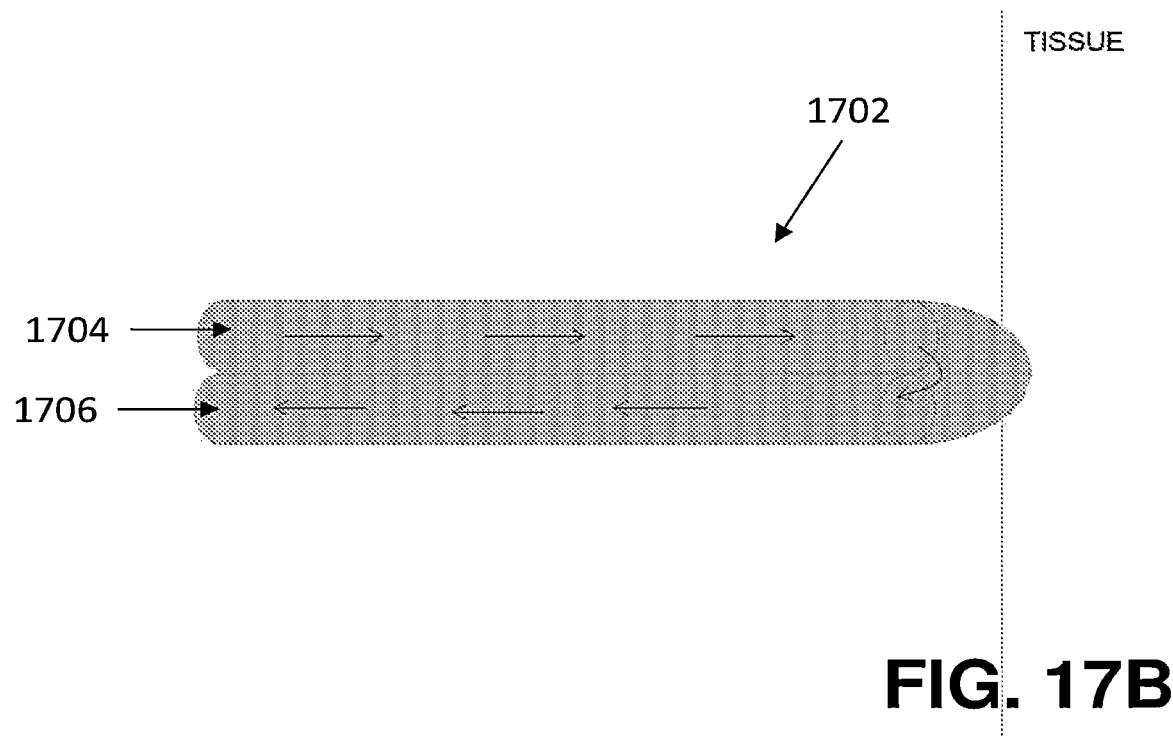

FIG. 17A-17B illustrates different embodiments of double barrel probes, including penetrating and nonpenetrating probes.

Figure 18:
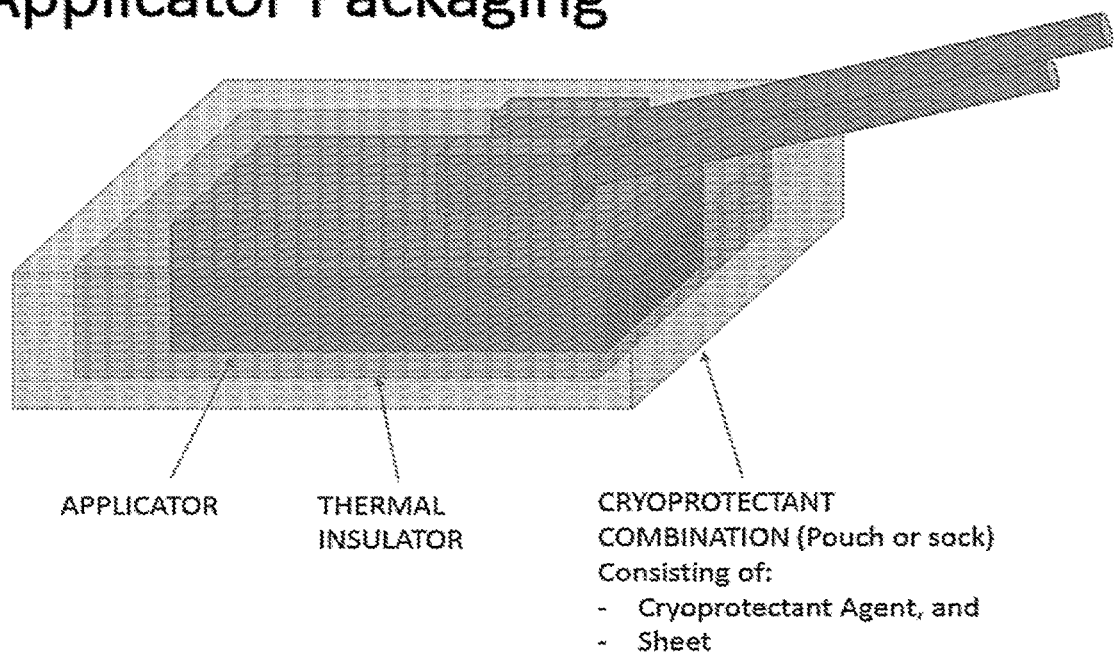

FIG. 18 is an embodiment showing one example of Applicator packaging.

Figure 19:
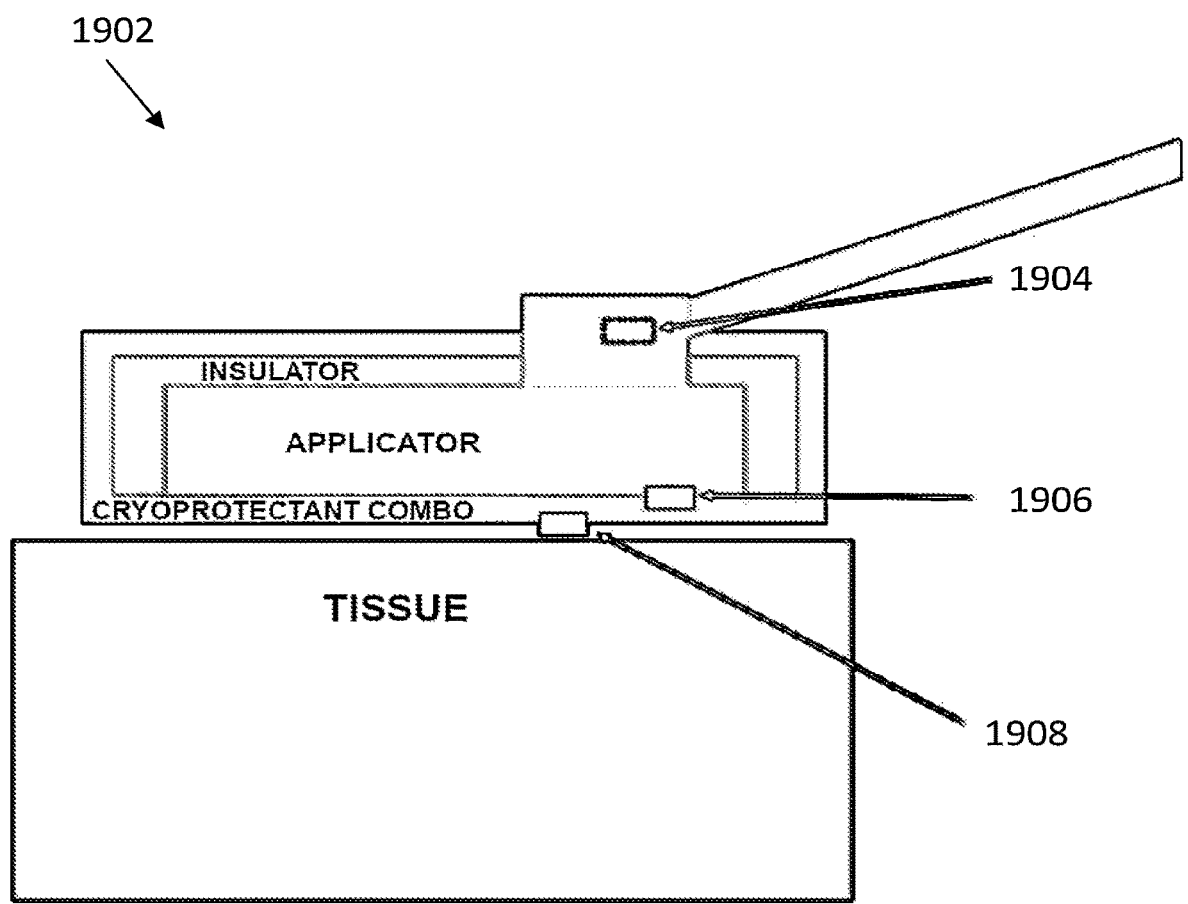

FIG. 19 is an embodiment of an Applicator with additional sensor placements.

Figure 20:
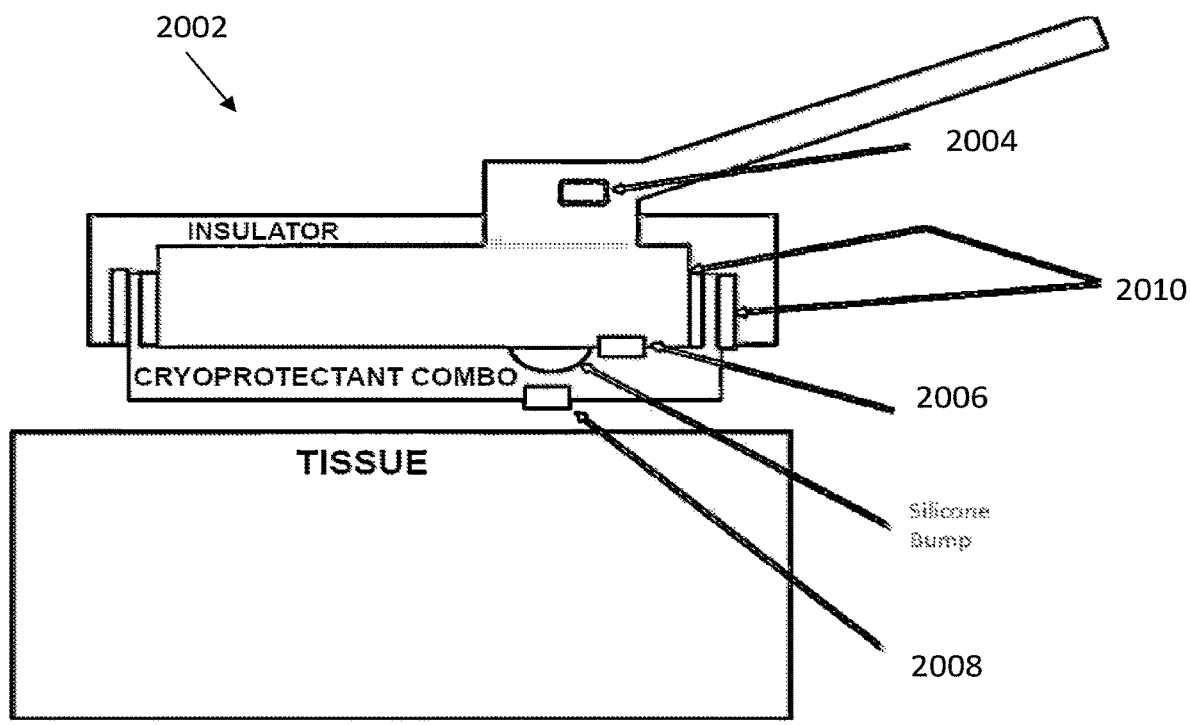

FIG. 20 illustrates an alternative embodiment of an Applicator.

Figure 21A:
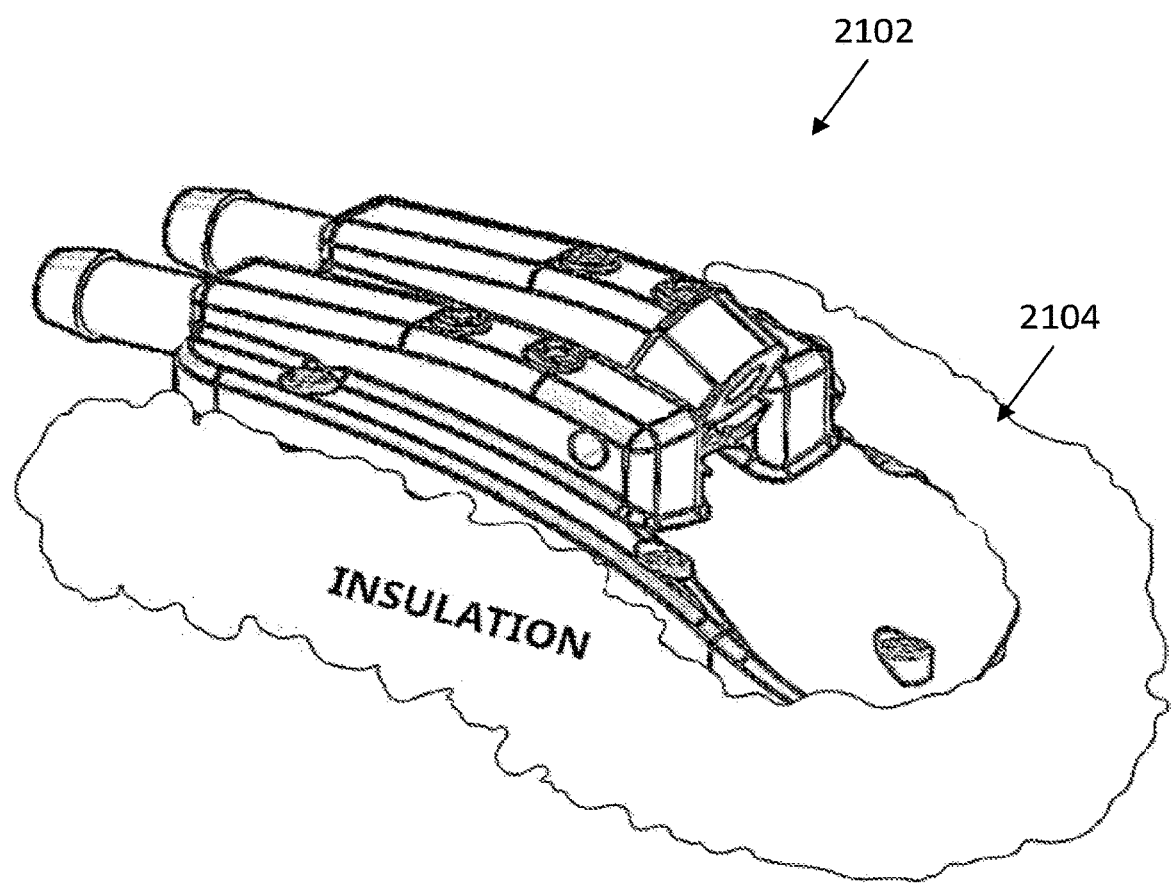
Figure 21B:
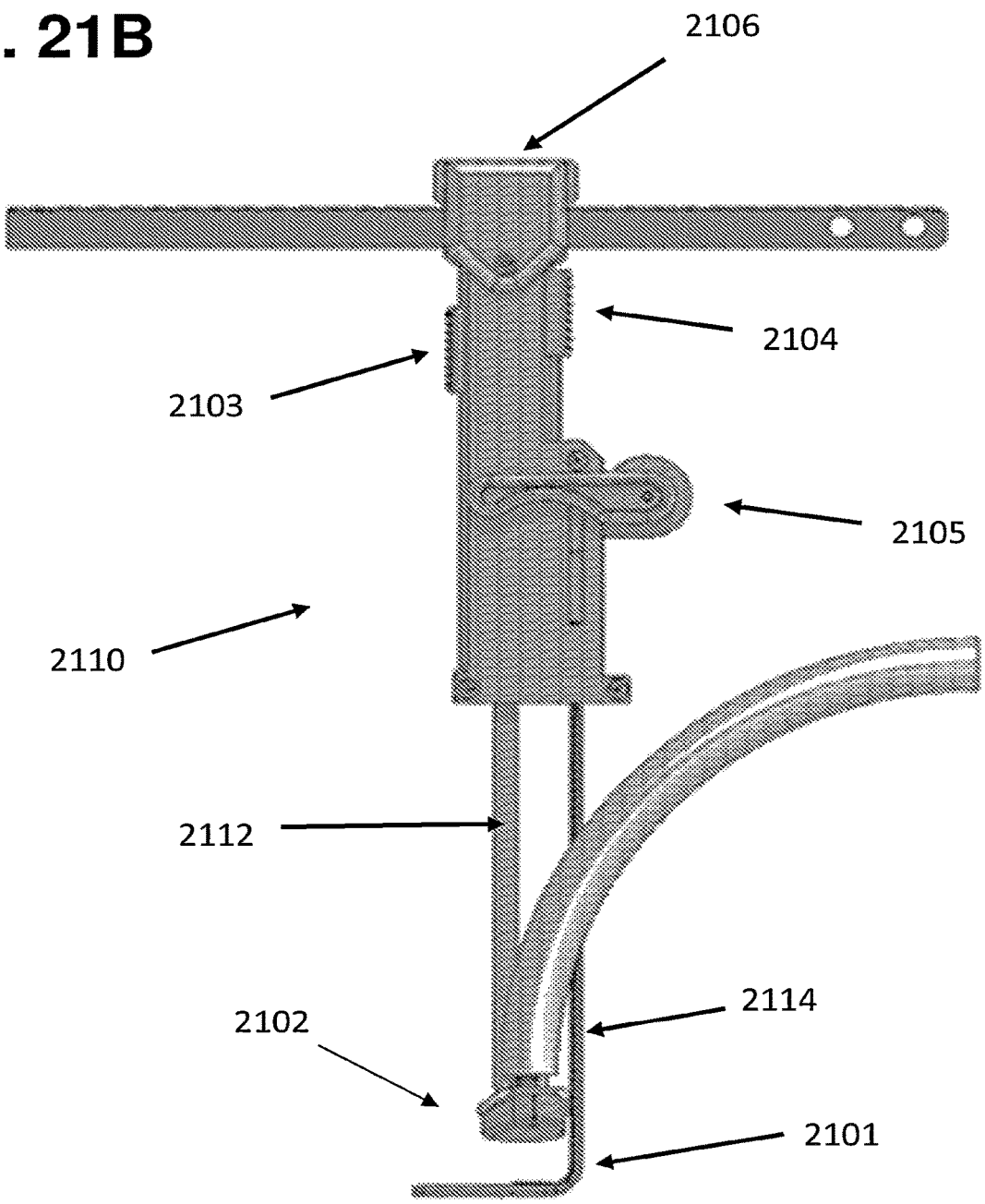

FIG. 21A-21B illustrates additional embodiments of an Applicator with insulation attached to the Applicator to protect areas of the oral cavity that are not the targets of the therapy.

Figure 22A:
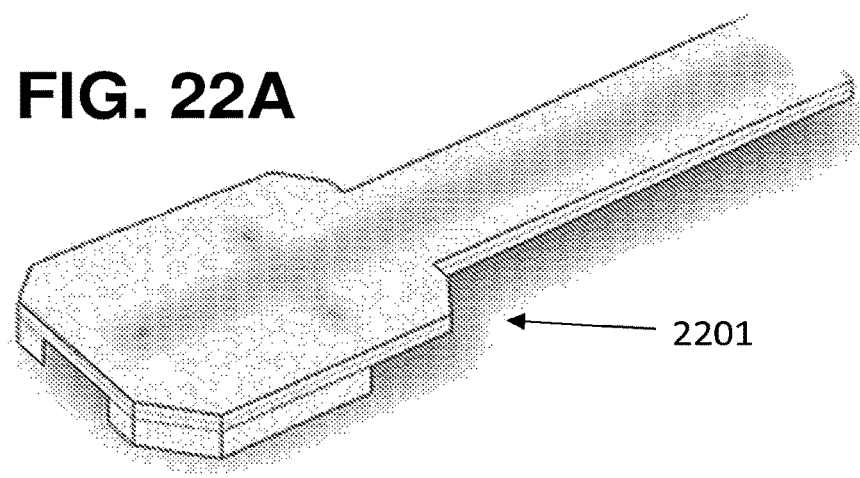
Figure 22B:
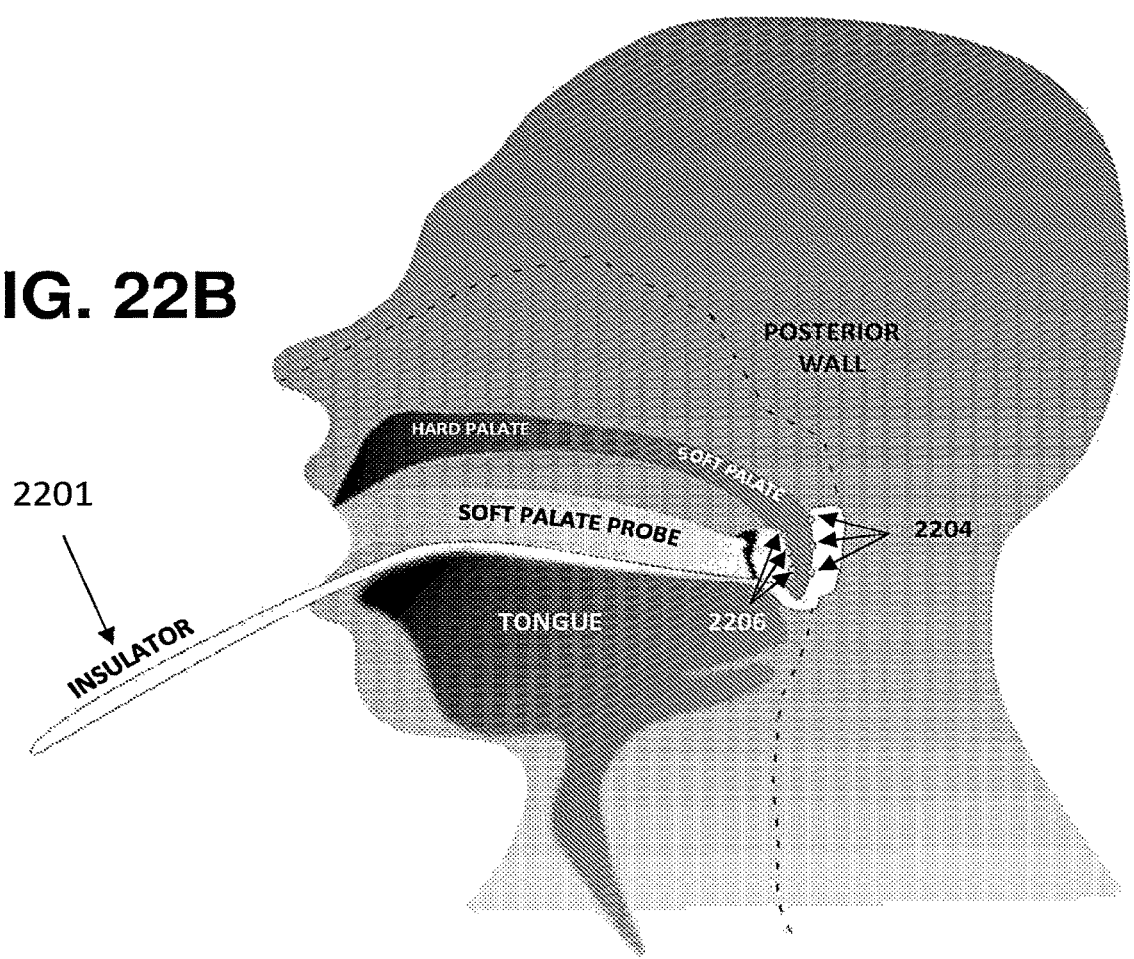

FIGS. 22A and 22B illustrate an embodiment of insulation that is disjoint from the Soft Palate Applicator to protect the posterior wall, where 22A illustrates the physical insulation and 22B illustrates its application during the clinical procedure.

Figure 23:
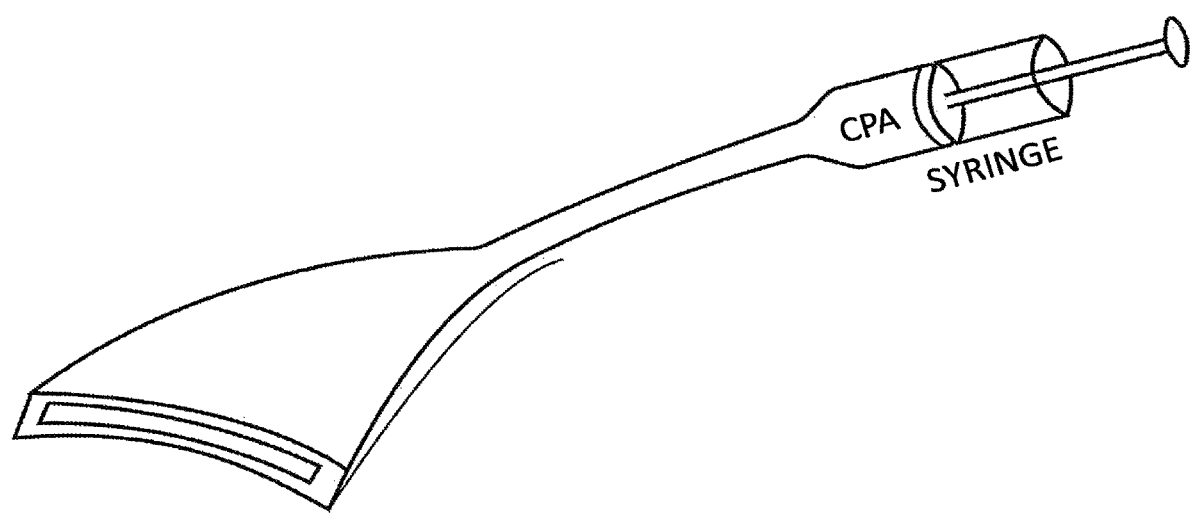

FIG. 23 illustrates another device that can be used for the preapplication of the cryoprotectant agent in the shape of an oral spatula.

Figure 24:
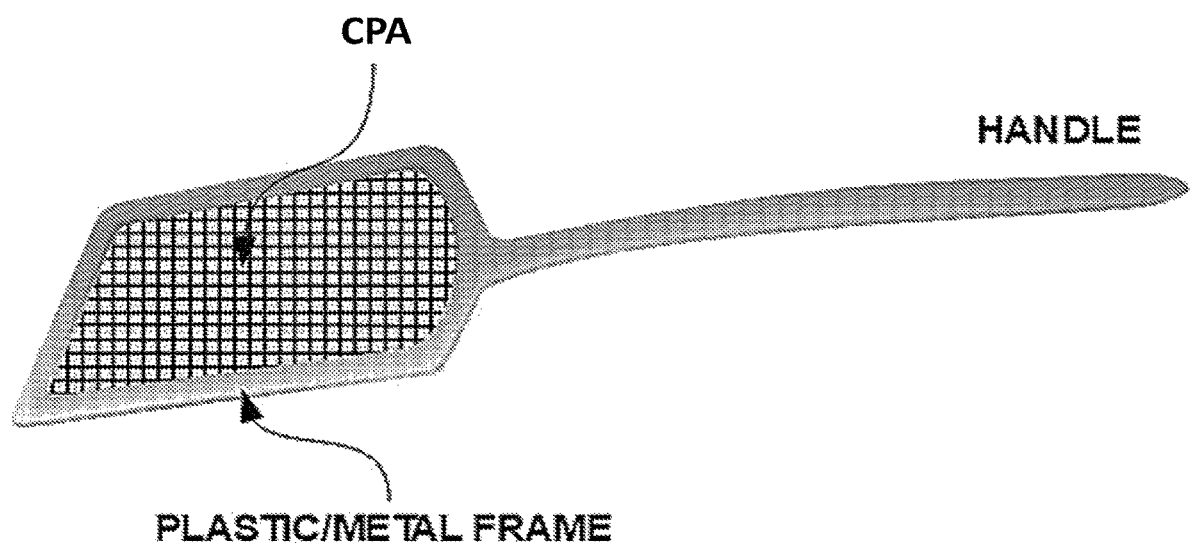

FIG. 24 illustrates another device for the preapplication of cryoprotectant.

Figure 25:
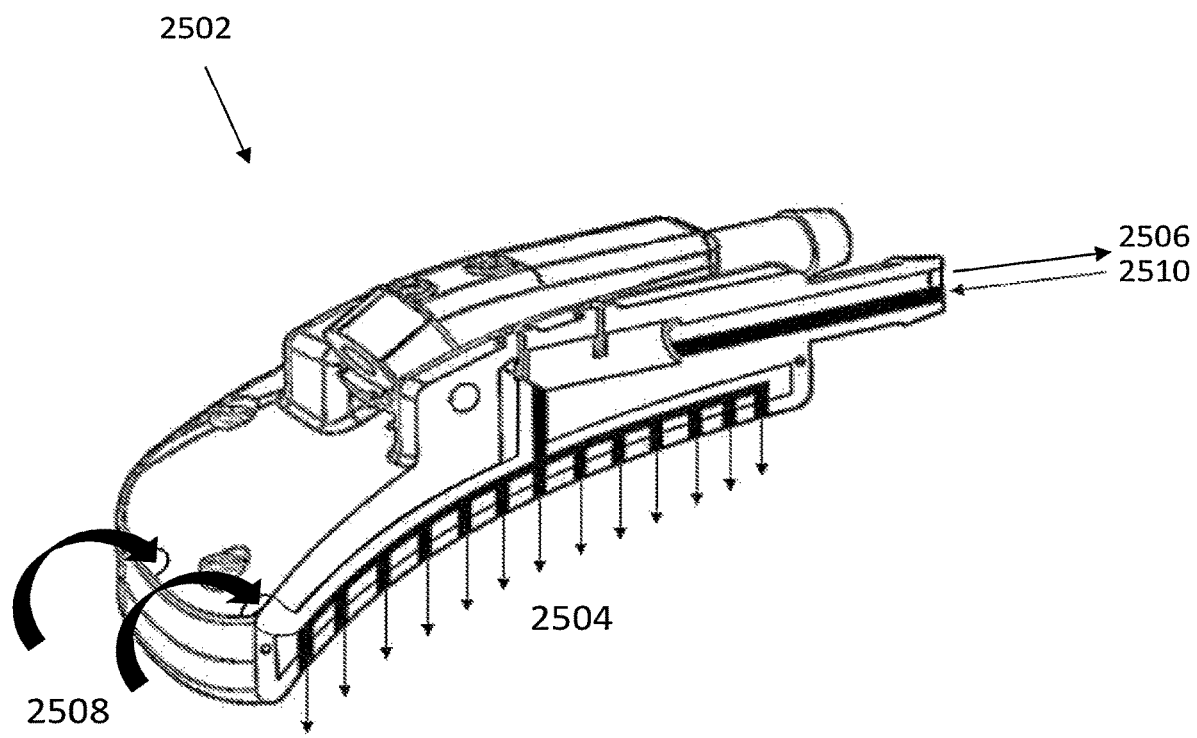

FIG. 25 illustrates an additional embodiment of an Applicator that allows cryoprotectant dispensing and suctioning.

Figure 26A:
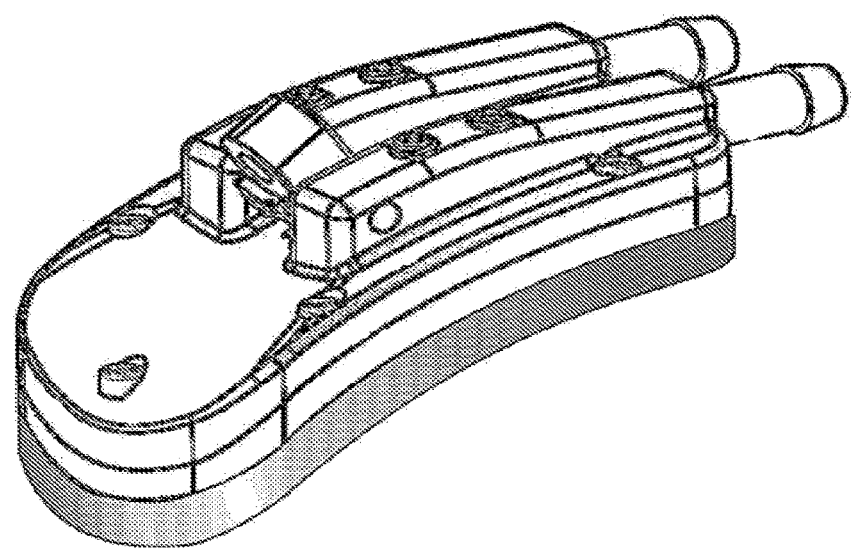
Figure 26B:
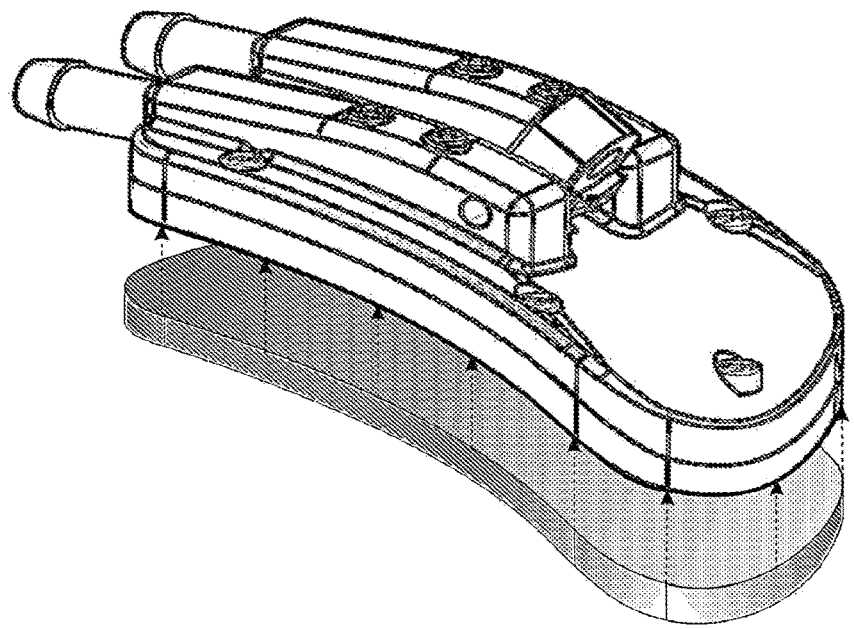

FIG. 26A-26B illustrates multiple embodiments of a cryoprotect agent that adheres to different surfaces.

Figure 27:
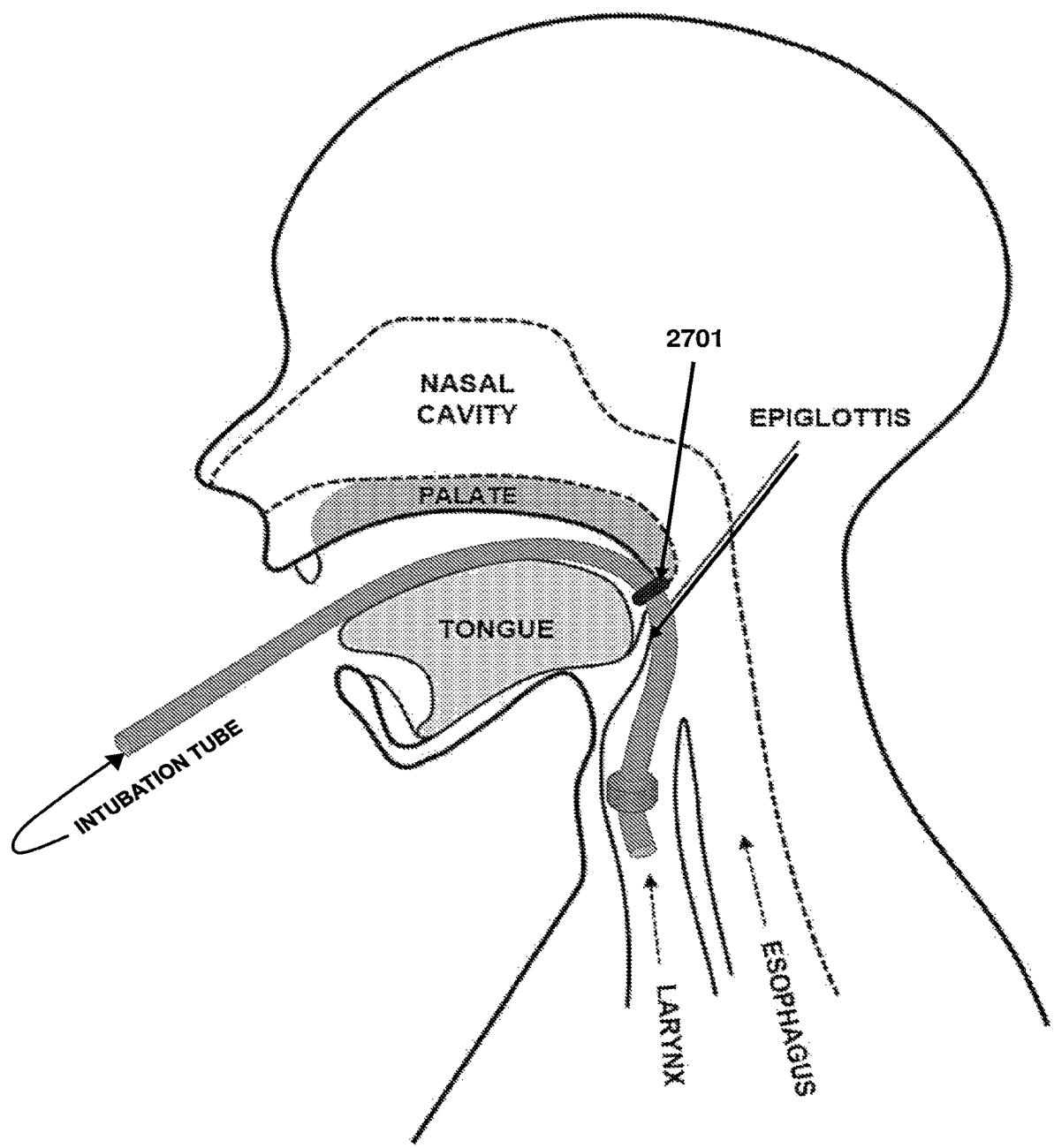

FIG. 27 illustrates a fluoroscopy-based visualization aid that can be used during the introduction of the Applicator.

Figure 28:
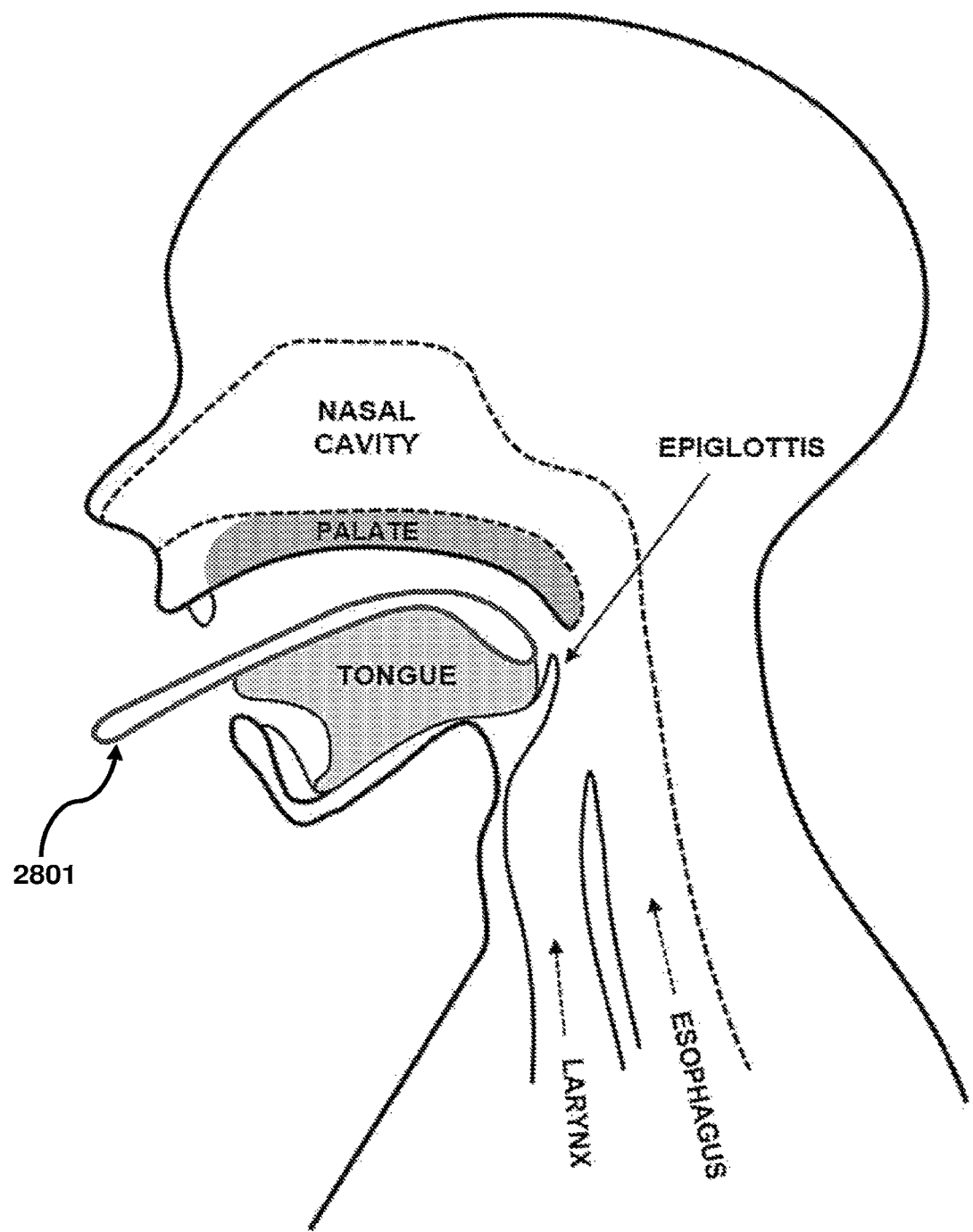

FIG. 28 illustrates another fluoroscopy-based visualization aid that can be used during the introduction of the Applicator.

Figure 29:
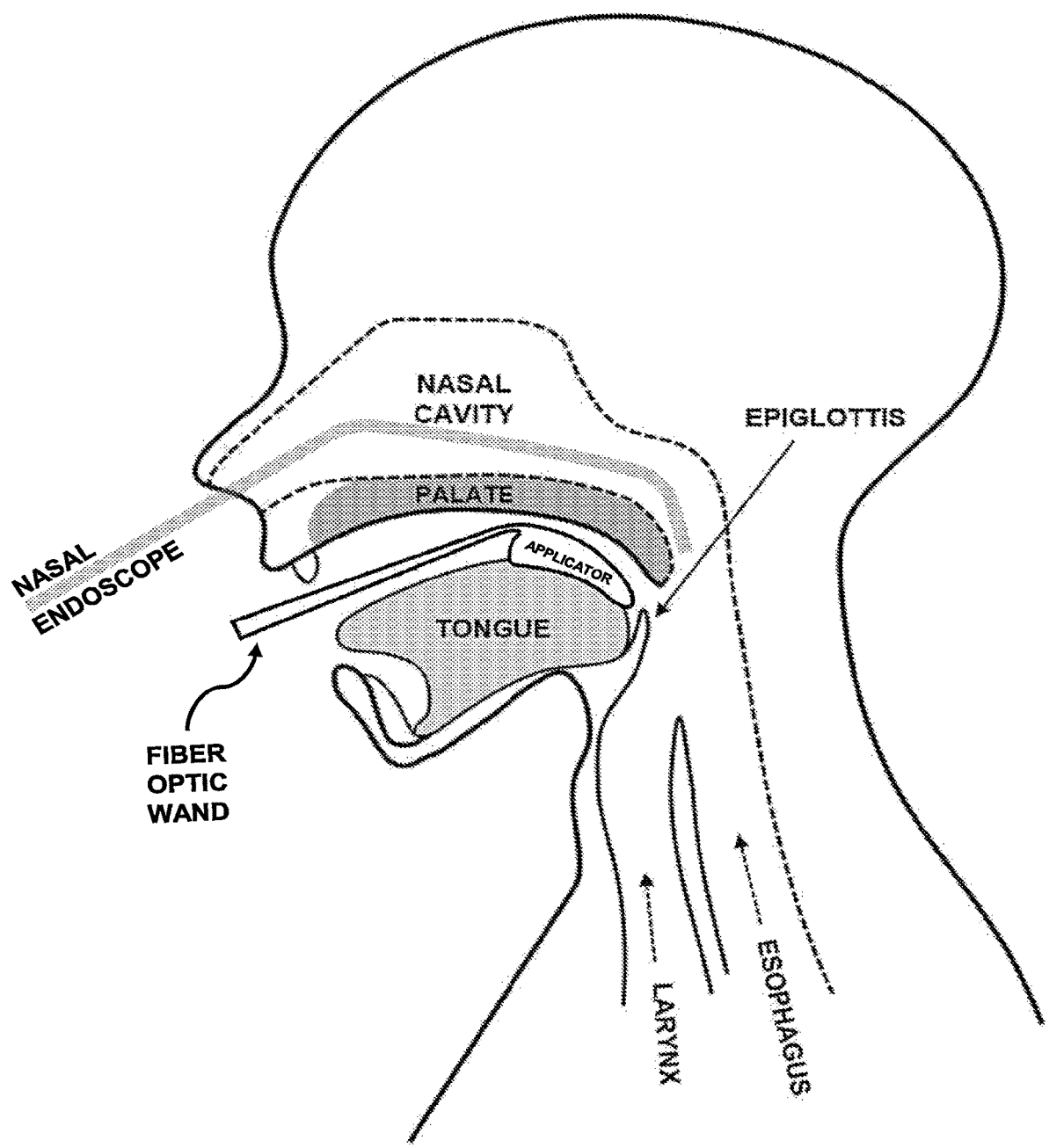

FIG. 29 illustrates optical visualization aids that can be used during the introduction of the Applicator.

Figure 30:
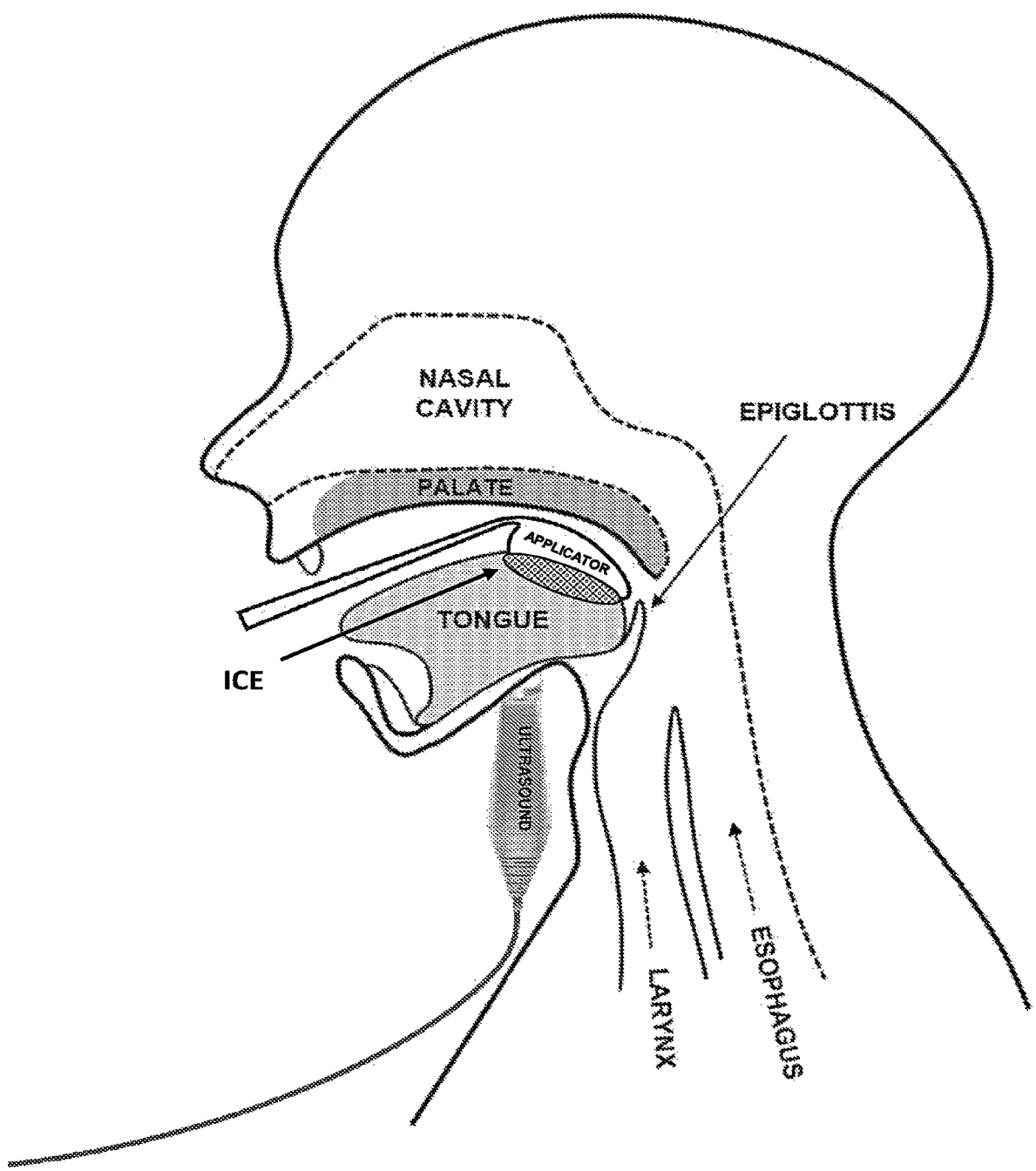

FIG. 30 illustrates an ultrasound-based visualization aid that can be used before or during the introduction of the Applicator.

Figure 31A:
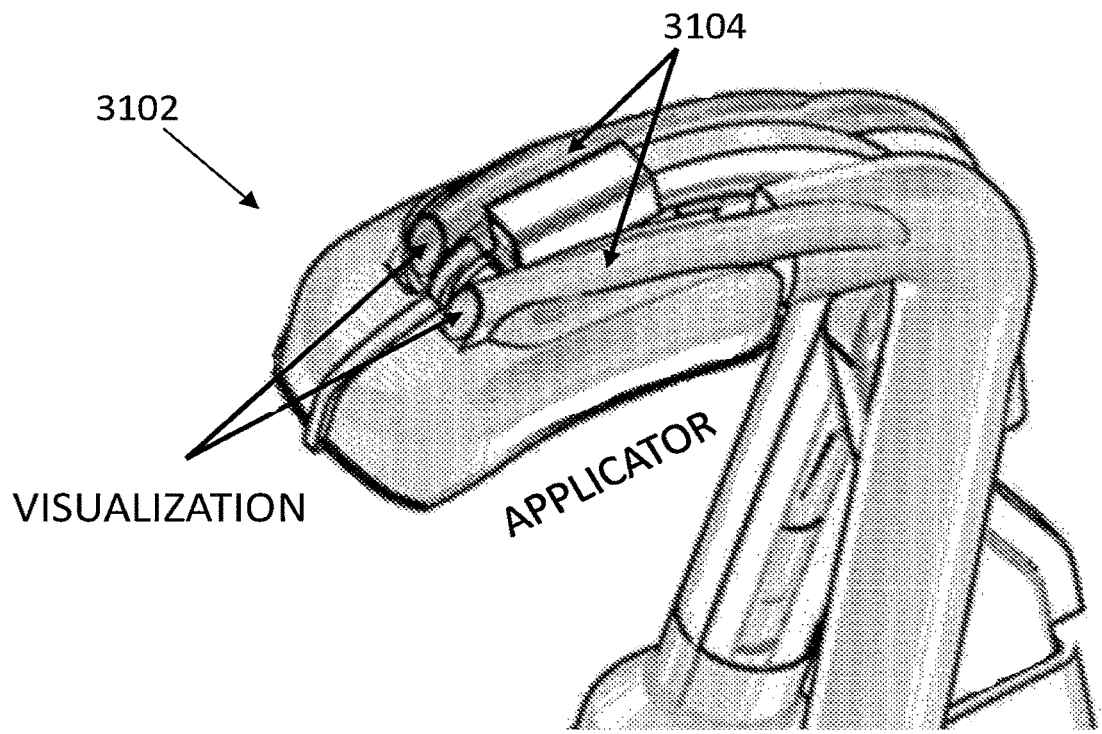
Figure 31B:
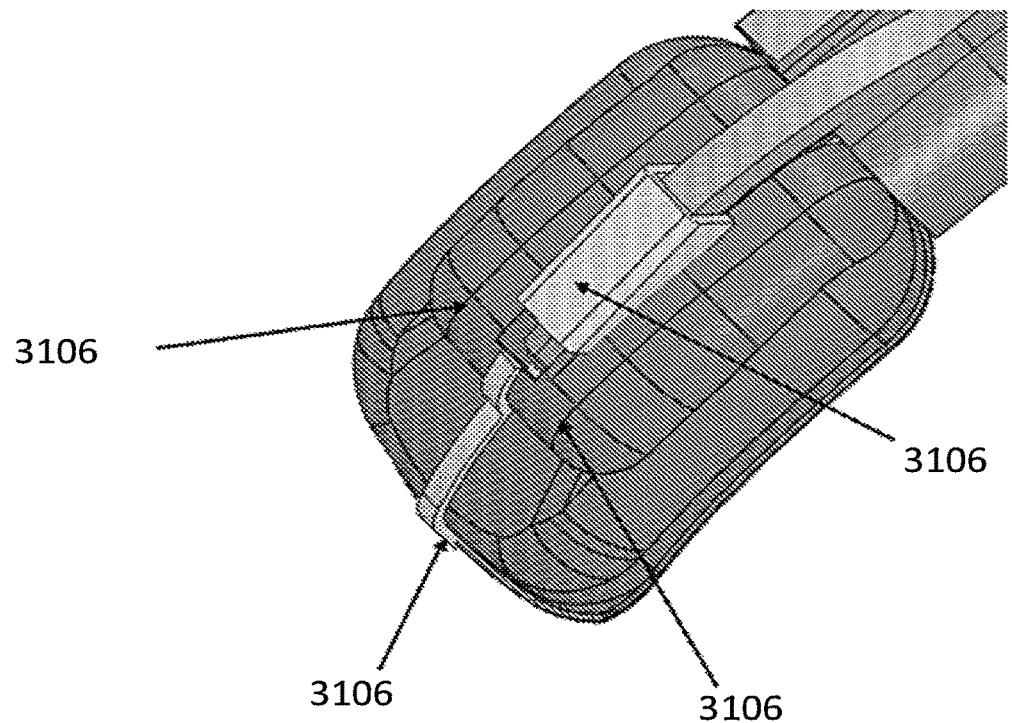

FIGS. 31A and 31B illustrate additional embodiments of an Applicator with working channels which can be used for the guided passage of suction tubes and endoscopes. FIG. 32A is an embodiment of an Applicator with two working channels, where one channel contains an optics camera in line with the Applicator to assist with visualization before, after, or during operation and the other contains a flexible suction tube for sterility. FIG. 31B illustrates potential locations for the working channel to be placed on the Applicator.

Figure 32:
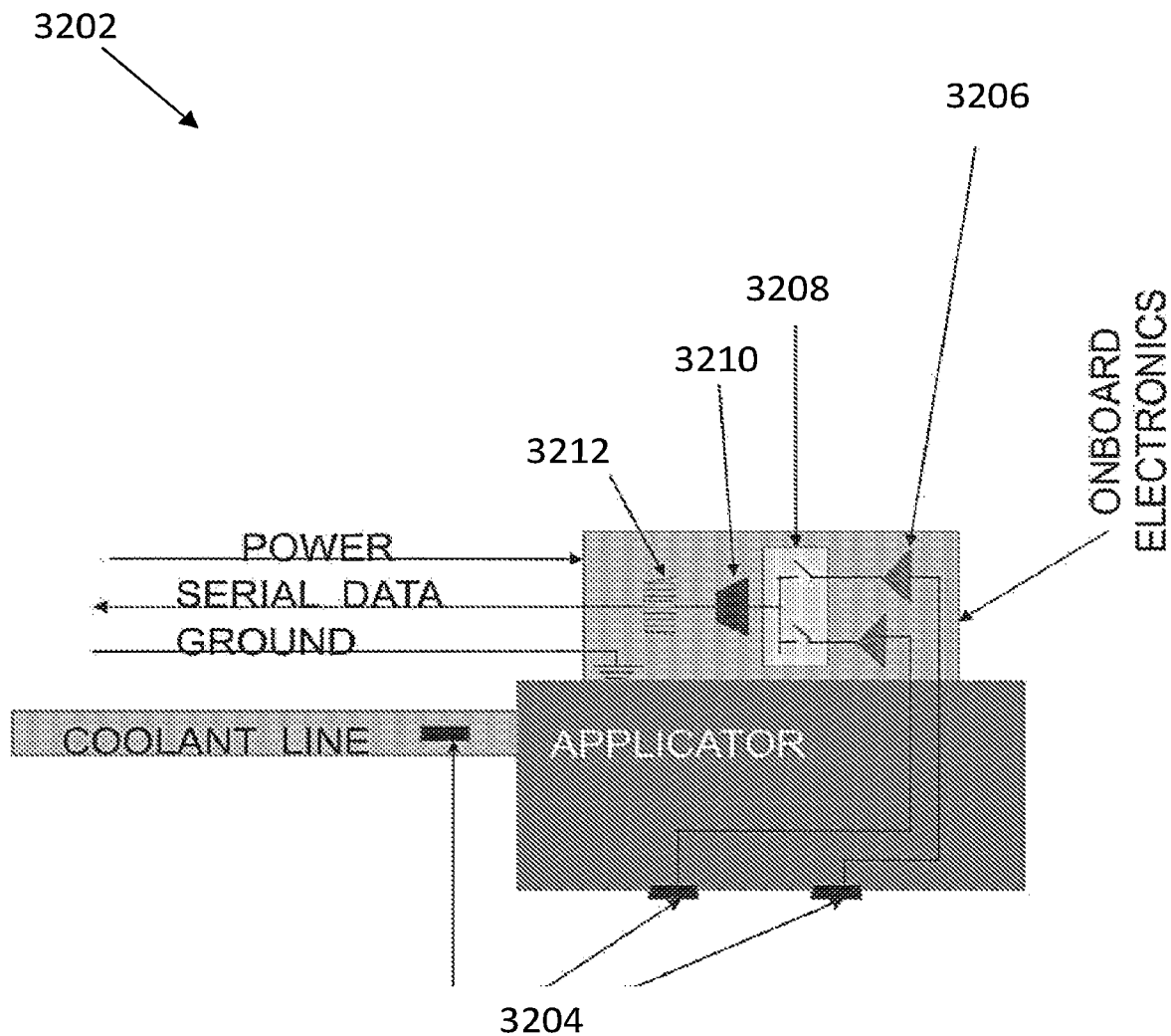

FIG. 32 shows the implementation of the incorporation of on-board electronics to the Applicator.

Figure 33A:
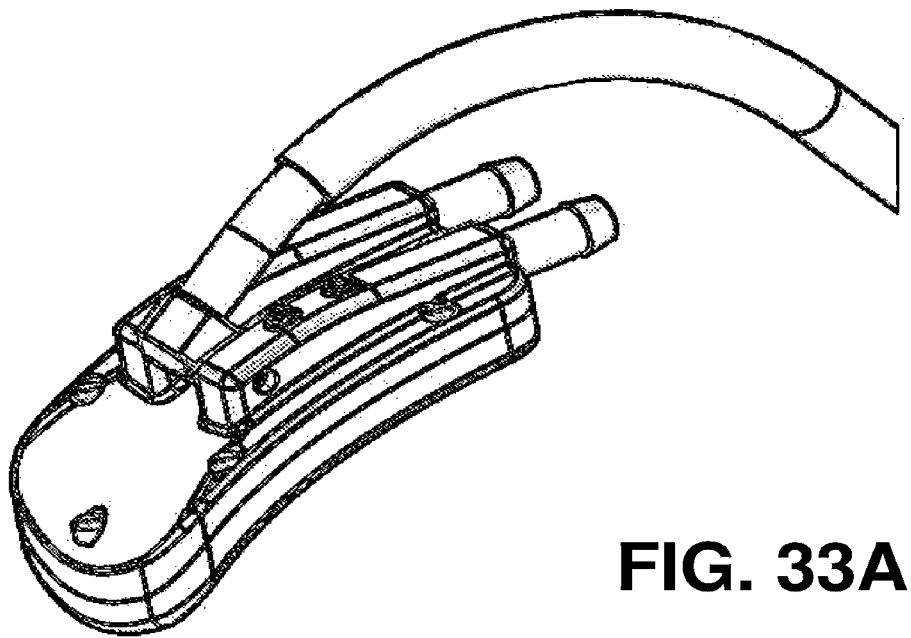
Figure 33B:
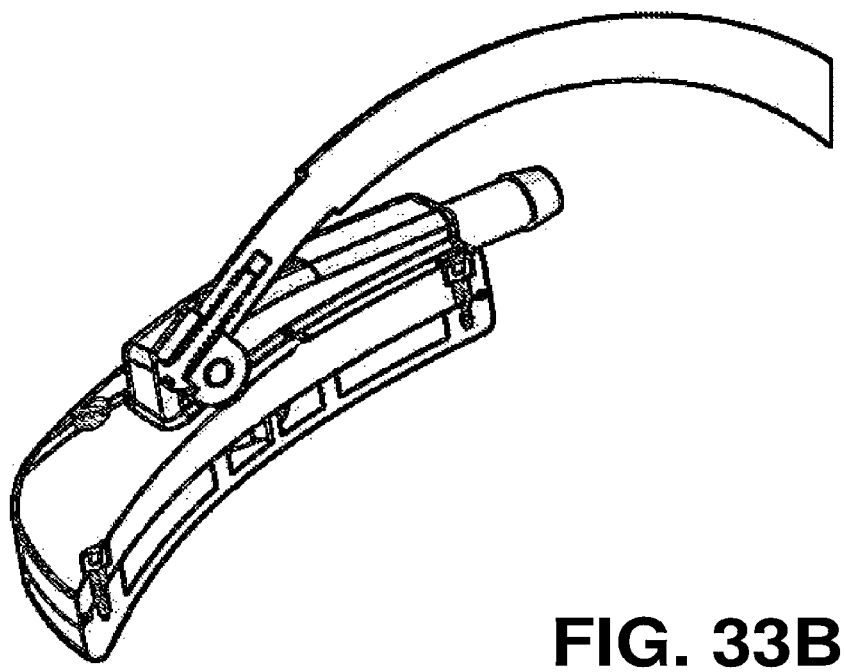

FIGS. 33A-33B illustrate an Applicator that is attached to a fixation arm with an articulated joint.

Figure 34A:
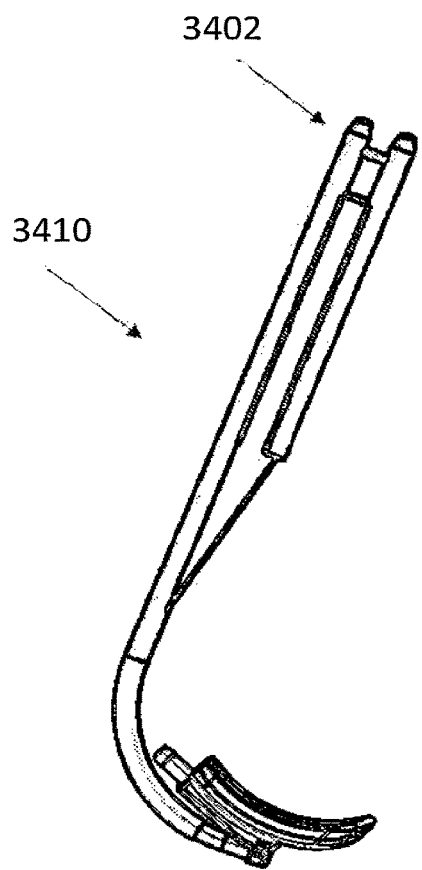
Figure 34B:
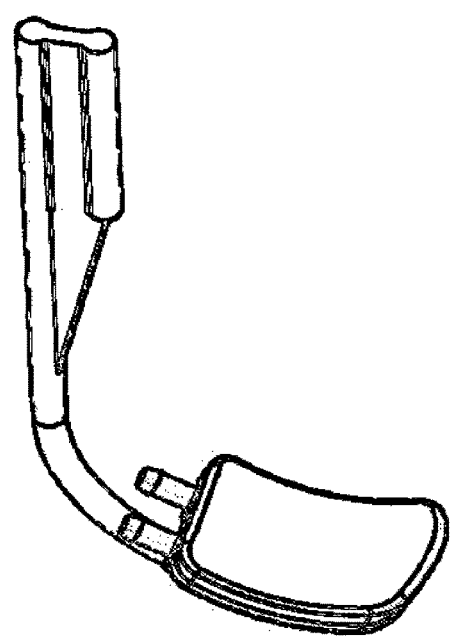

FIGS. 34A-34B illustrate a close-view of the arm of a sleep apnea treatment system.

FIGS. 35A-35D illustrate additional embodiments of the force traction system.

Figure 36A:
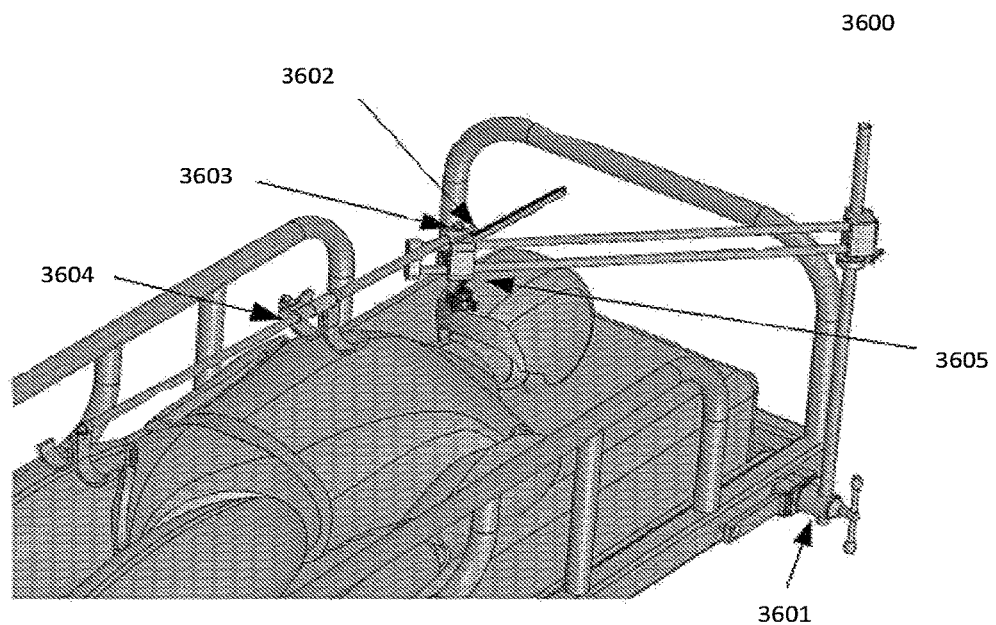
Figure 36B:
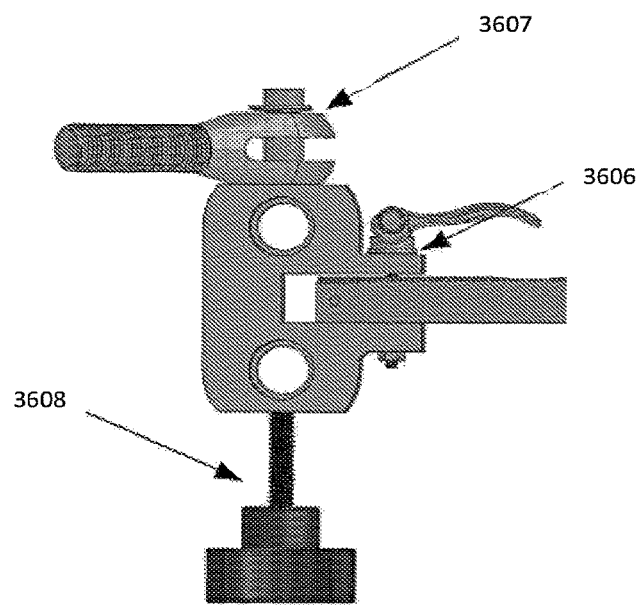

FIGS. 36A-36B illustrate one example of a mountable force traction system with a double barrel bearing.

Figure 37A:
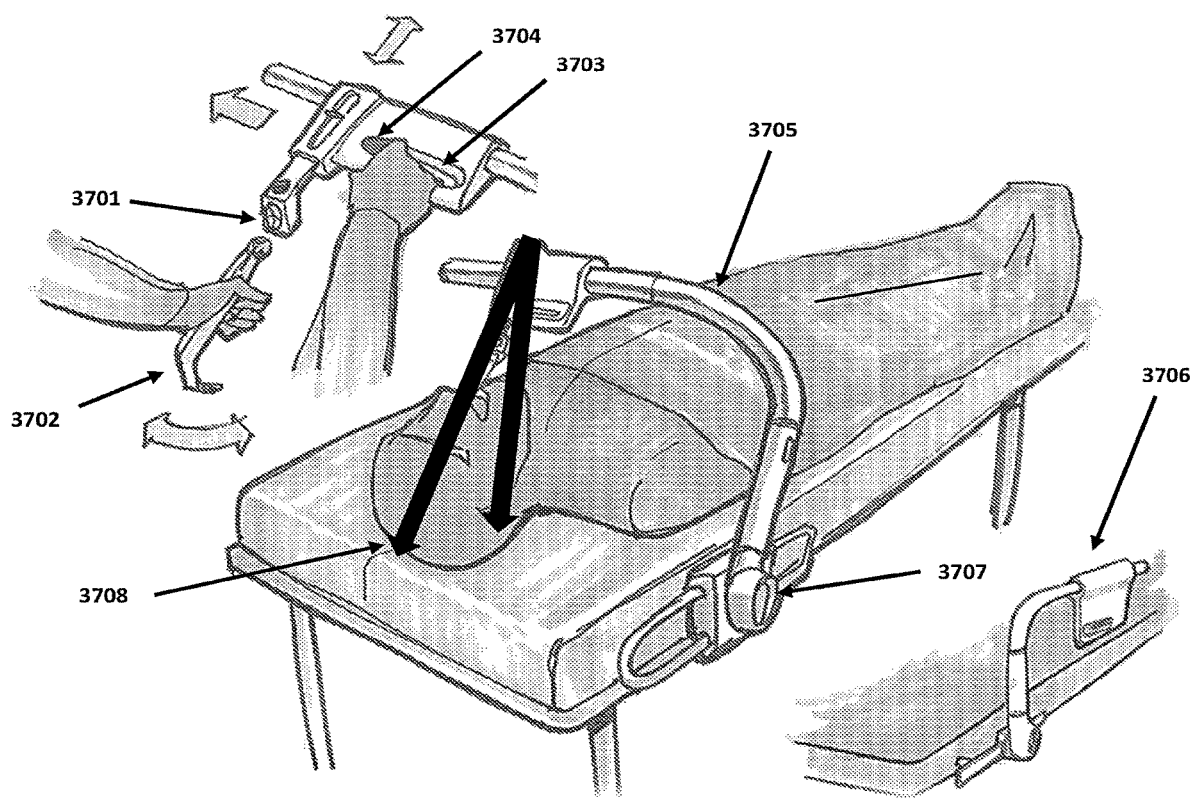
Figure 37B:
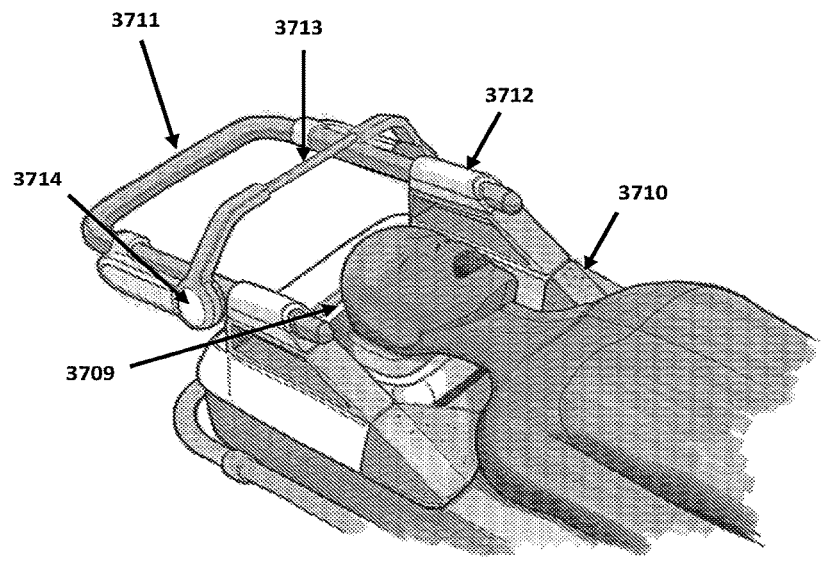
Figure 37C:
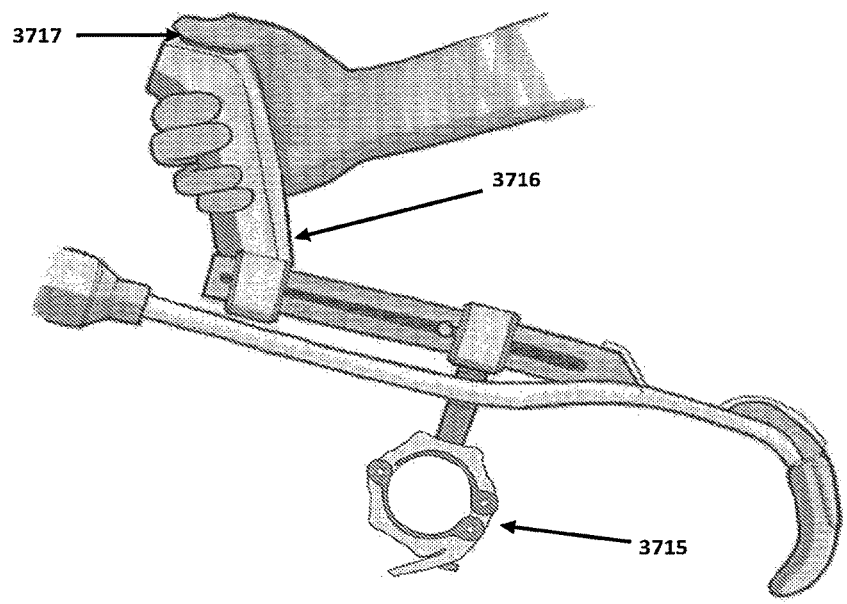

FIGS. 37A-37C illustrate examples of a mountable force traction system.

Figure 38A:
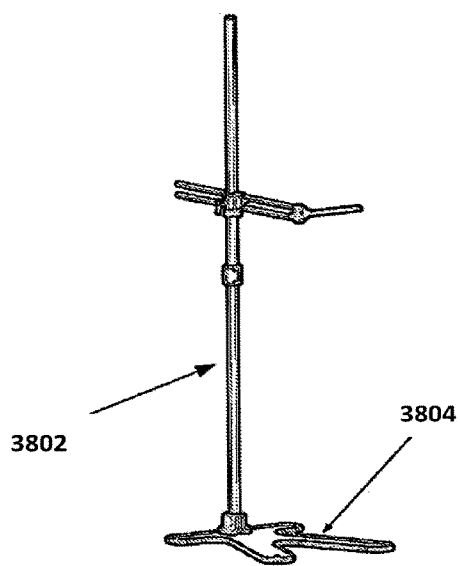
Figure 38B:
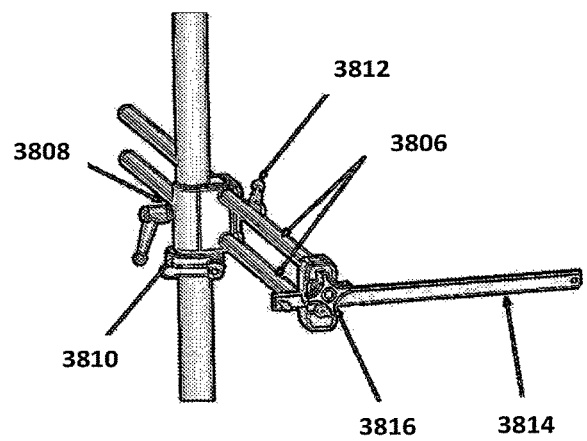
Figure 38C:
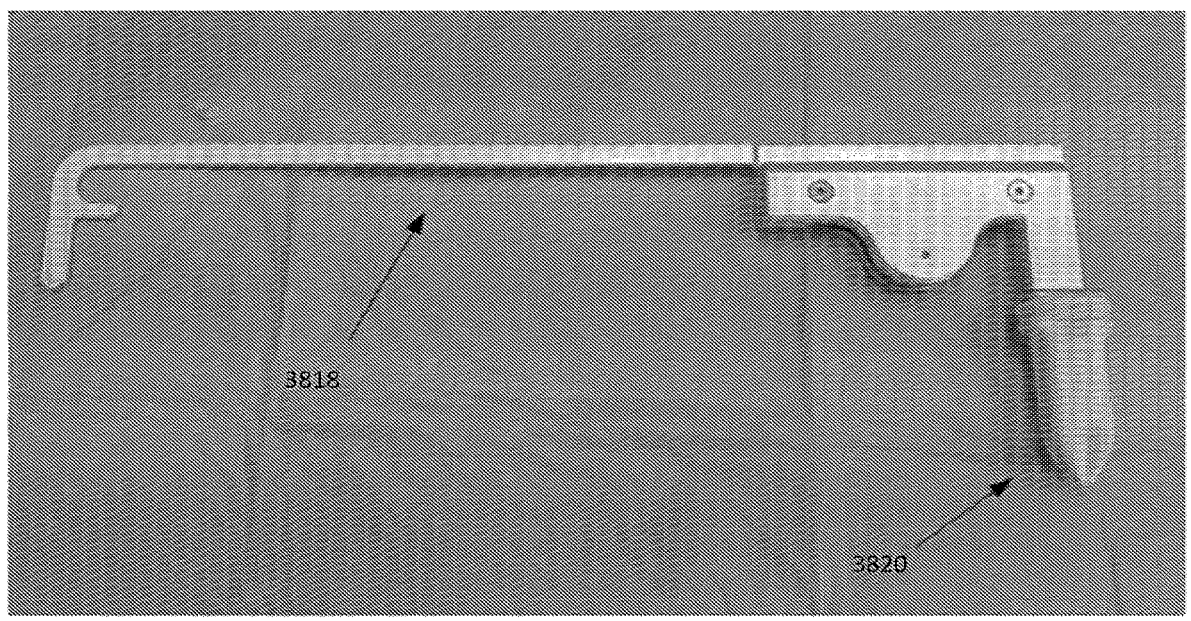

FIGS. 38A-38C illustrate one example of a standing force traction system with an attached alignment gauge.

Figure 39A:
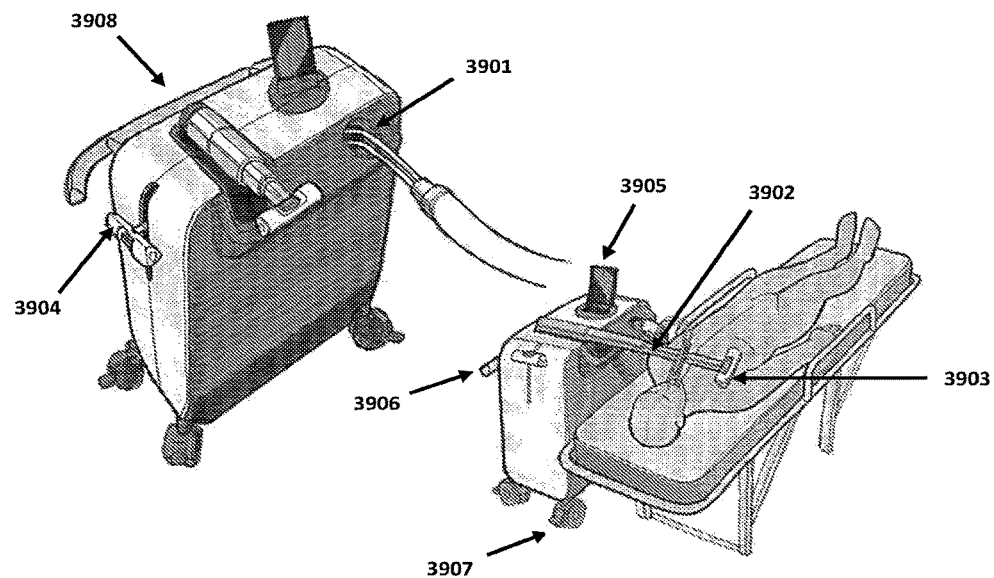
Figure 39B:
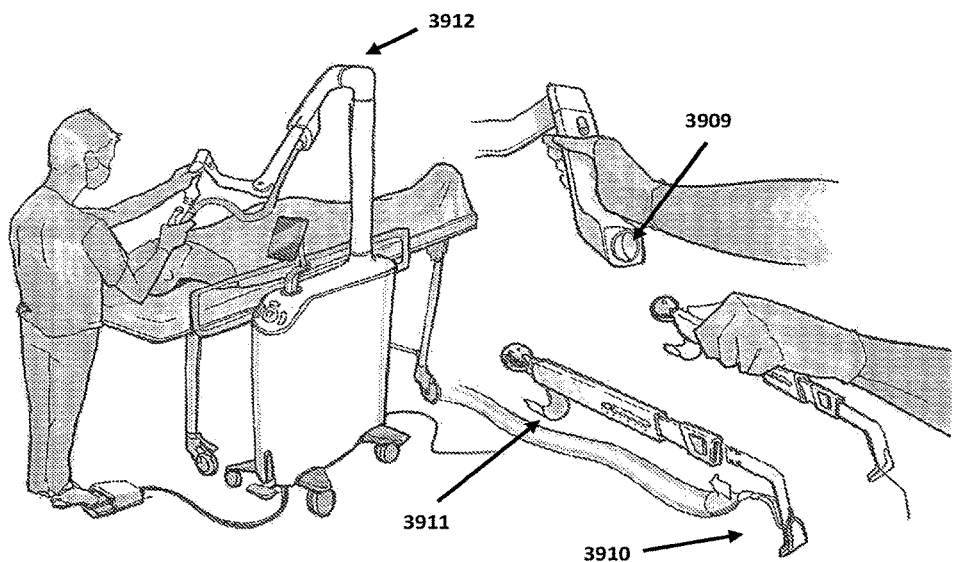

FIGS. 39A-39B illustrate examples of a cart mountable force traction system.

Figure 40A:
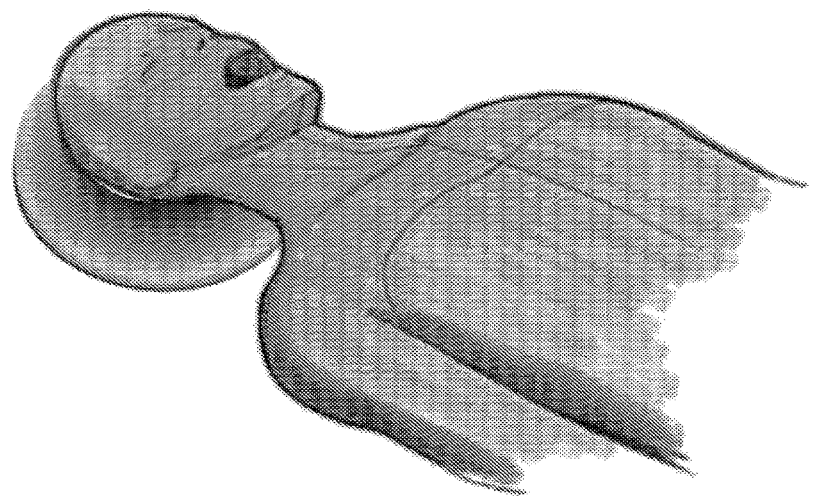
Figure 40B:
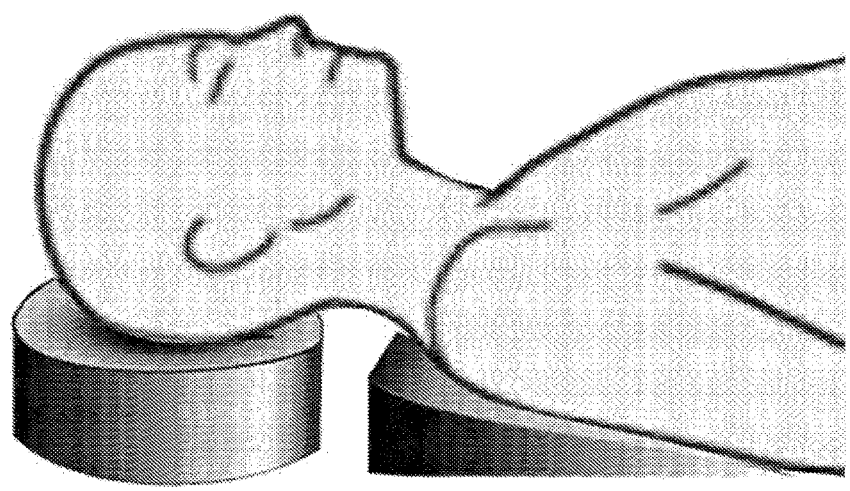

FIG. 40A-40B illustrates one example of customized padding to position the patient during treatment.

Figure 41:
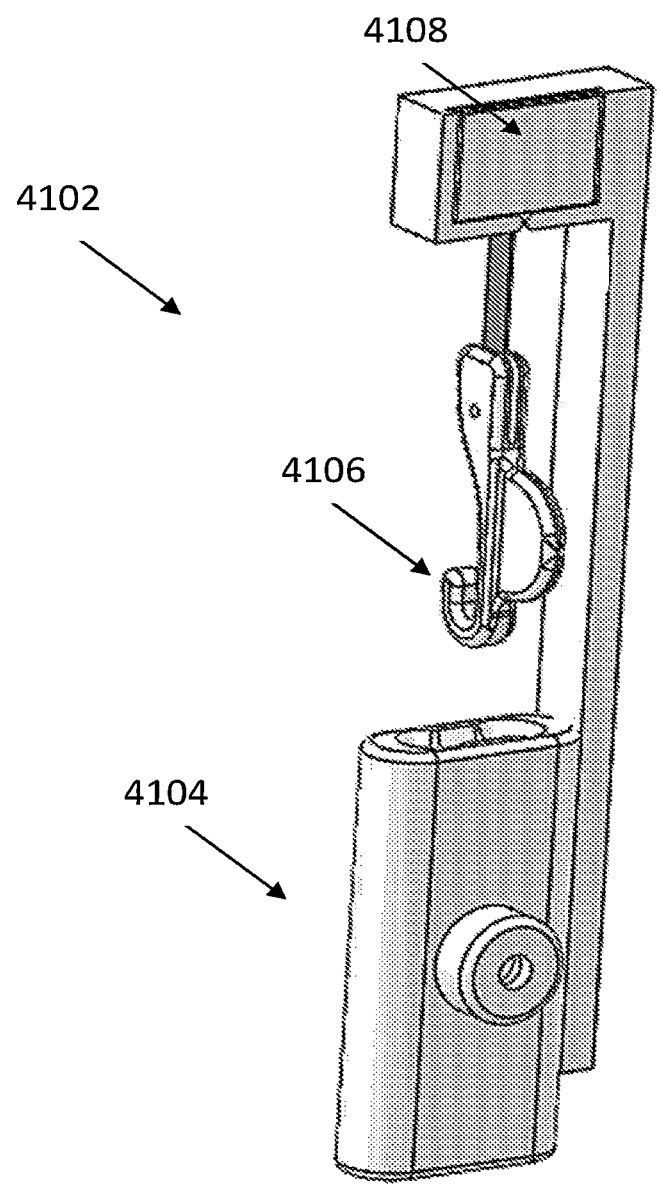

FIG. 41 is a close-up view of a constant force system.

Figure 42:
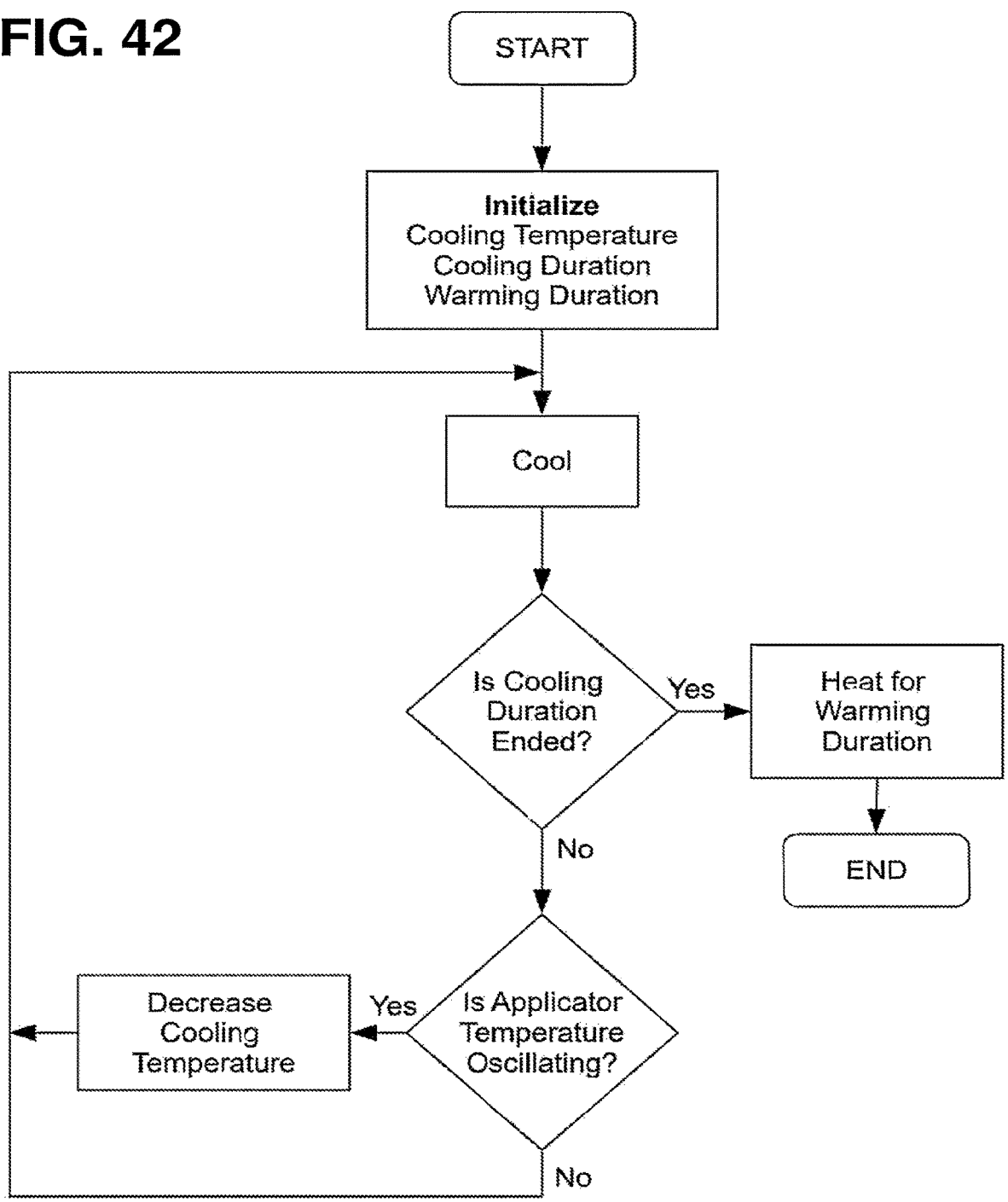

FIG. 42 illustrates a control algorithm flowchart.

Figure 43A:
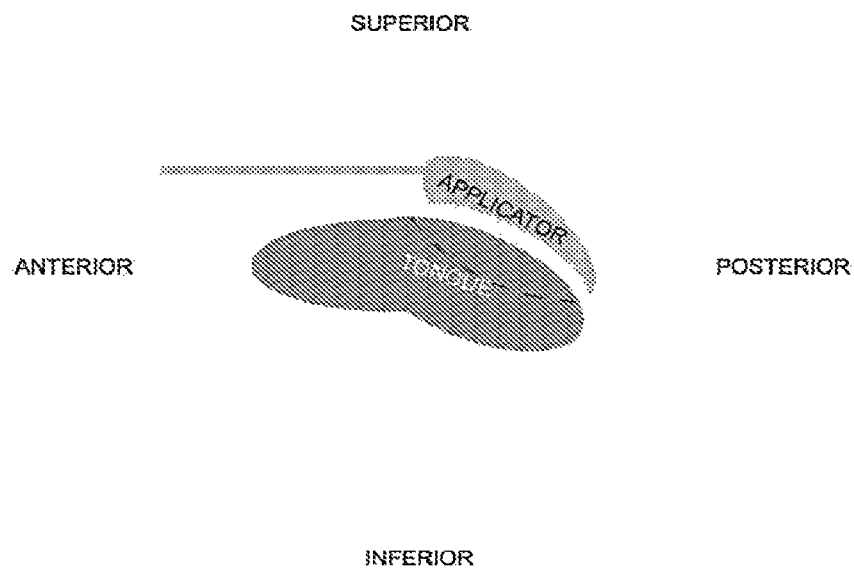
Figure 43B:
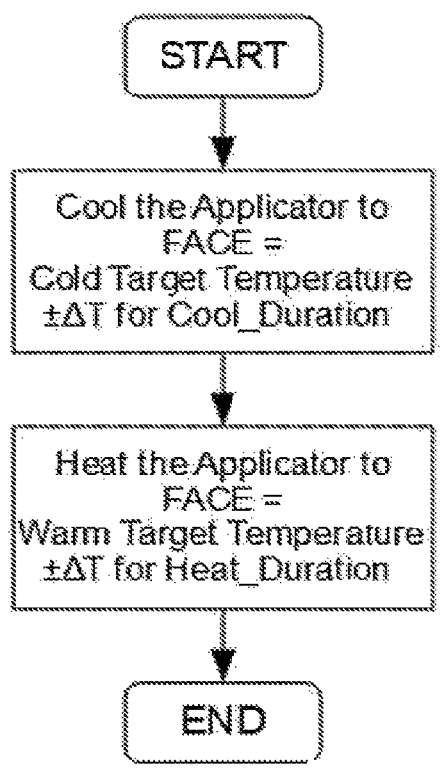
Figure 43C:
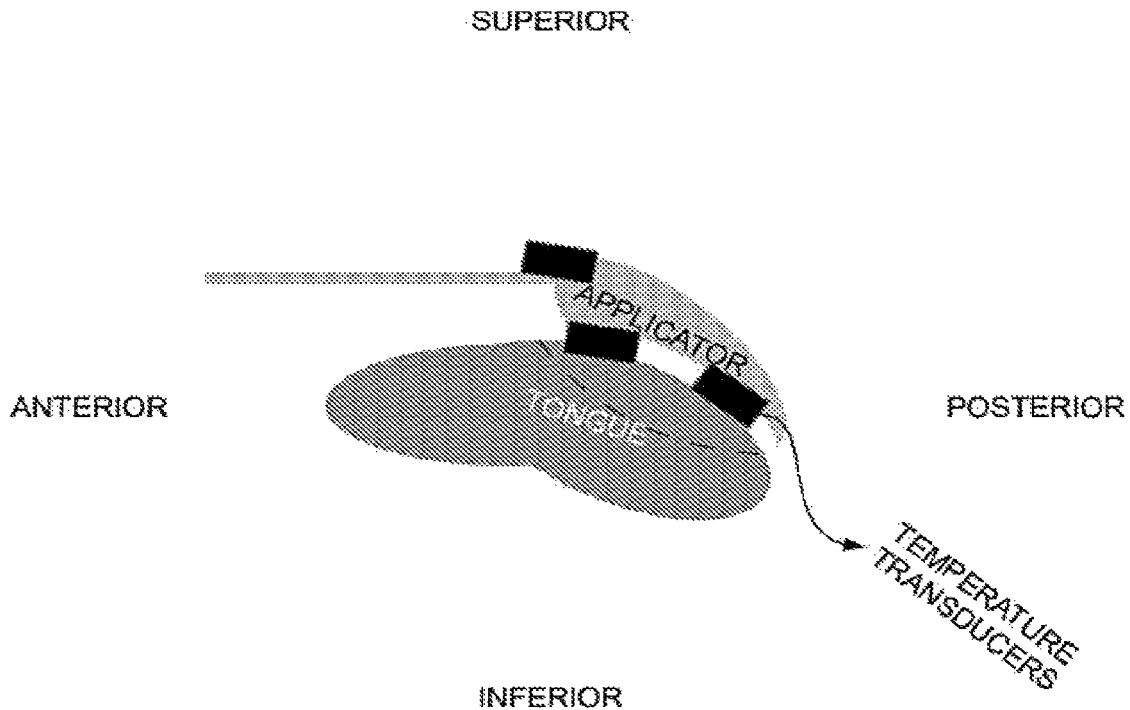
Figure 43D:
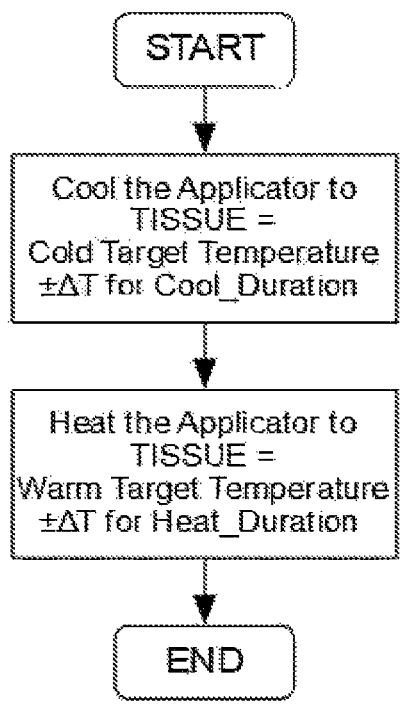
Figure 43E:
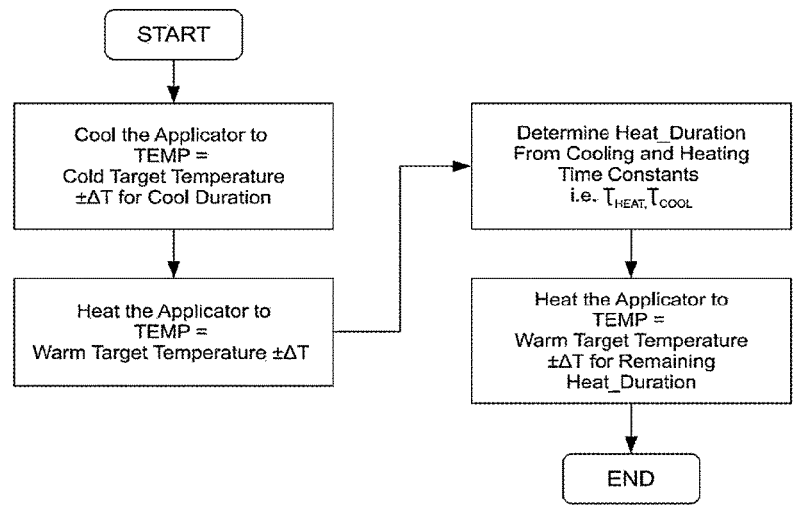
Figure 43F:
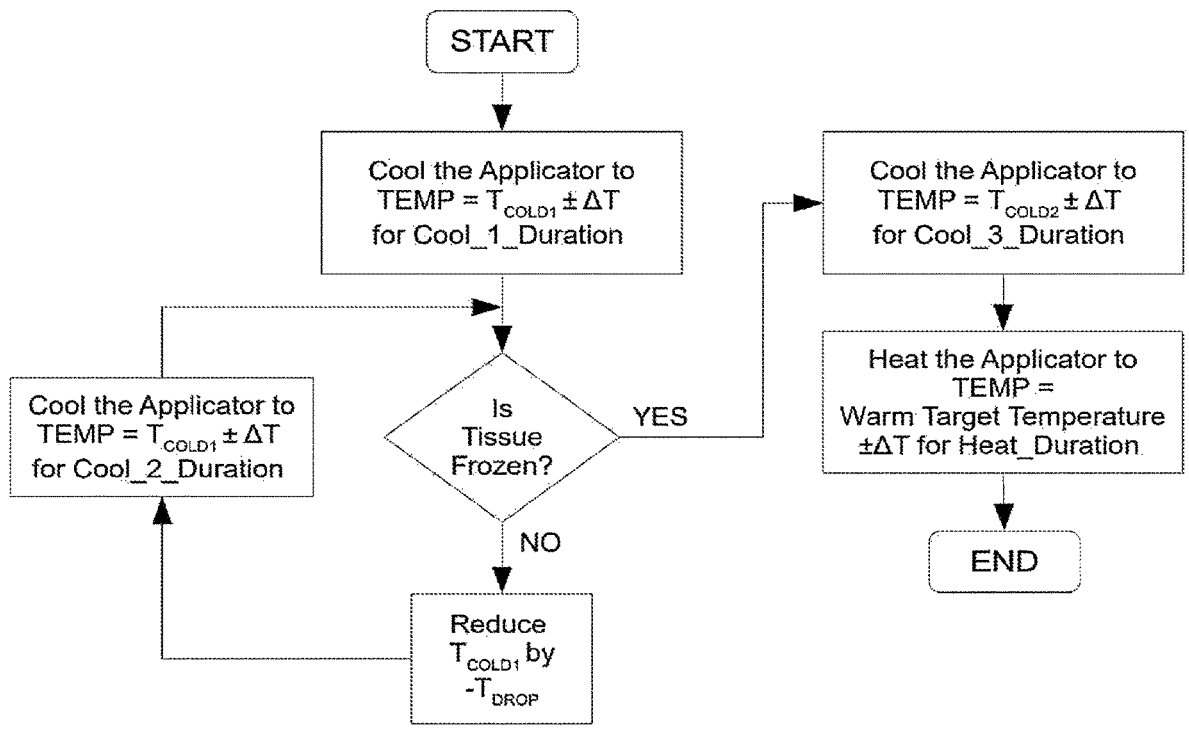
Figure 43G:
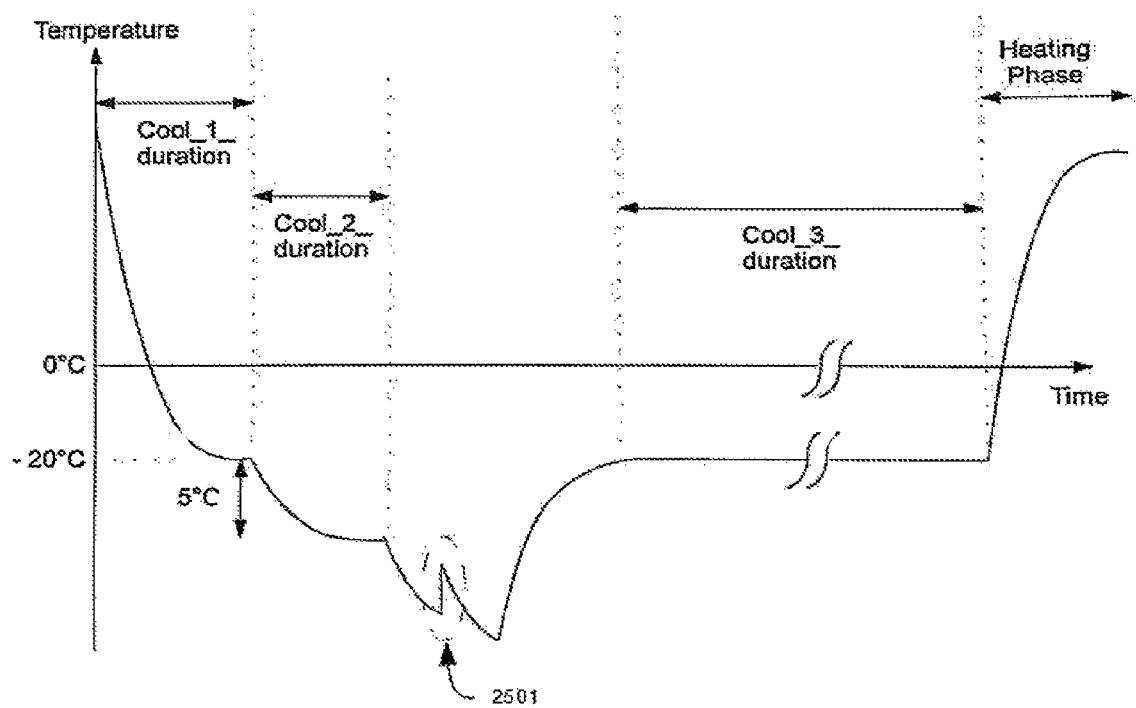
Figure 43H:
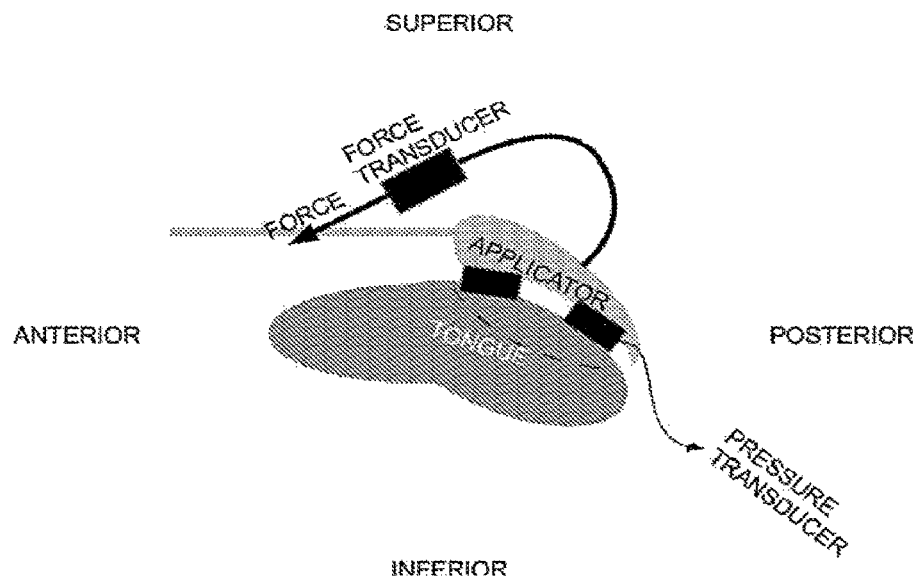
Figure 43I:
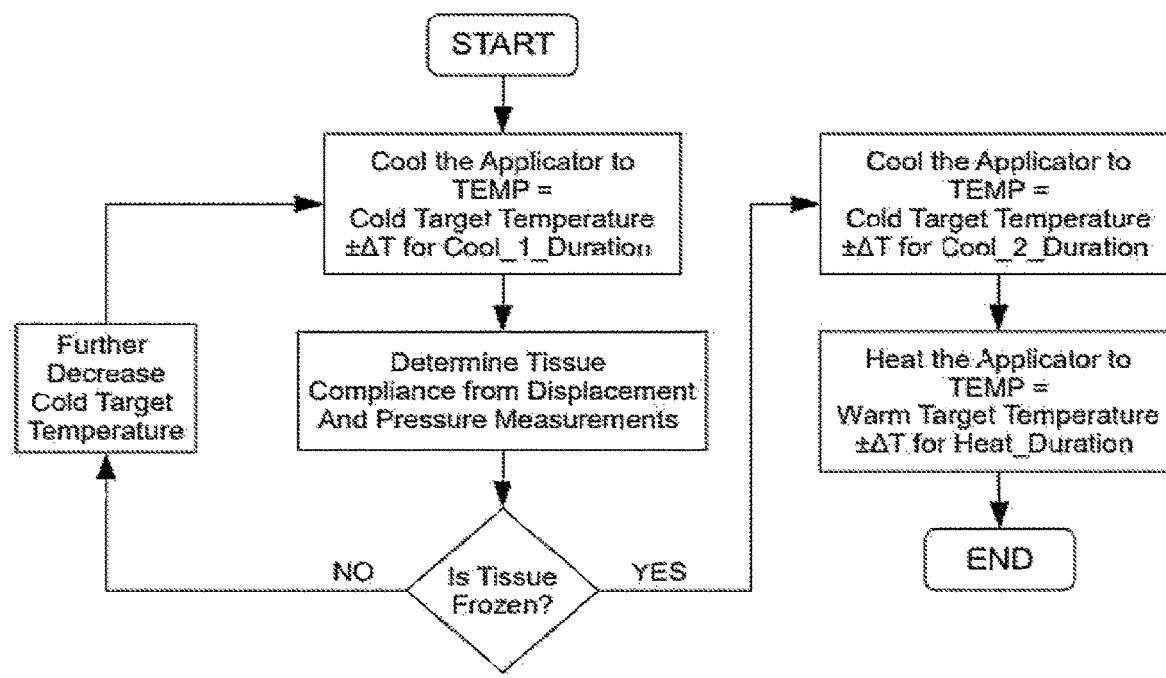
Figure 43J:
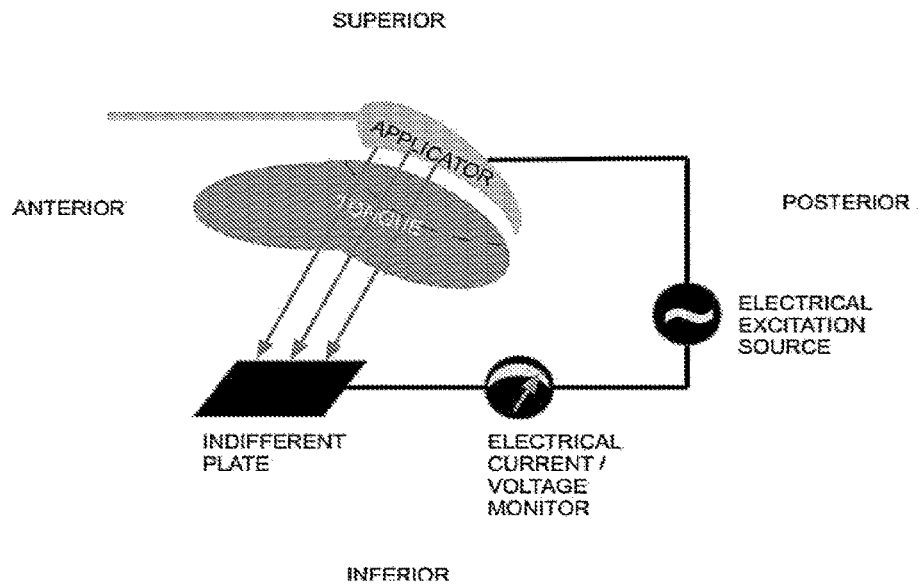
Figure 43K:
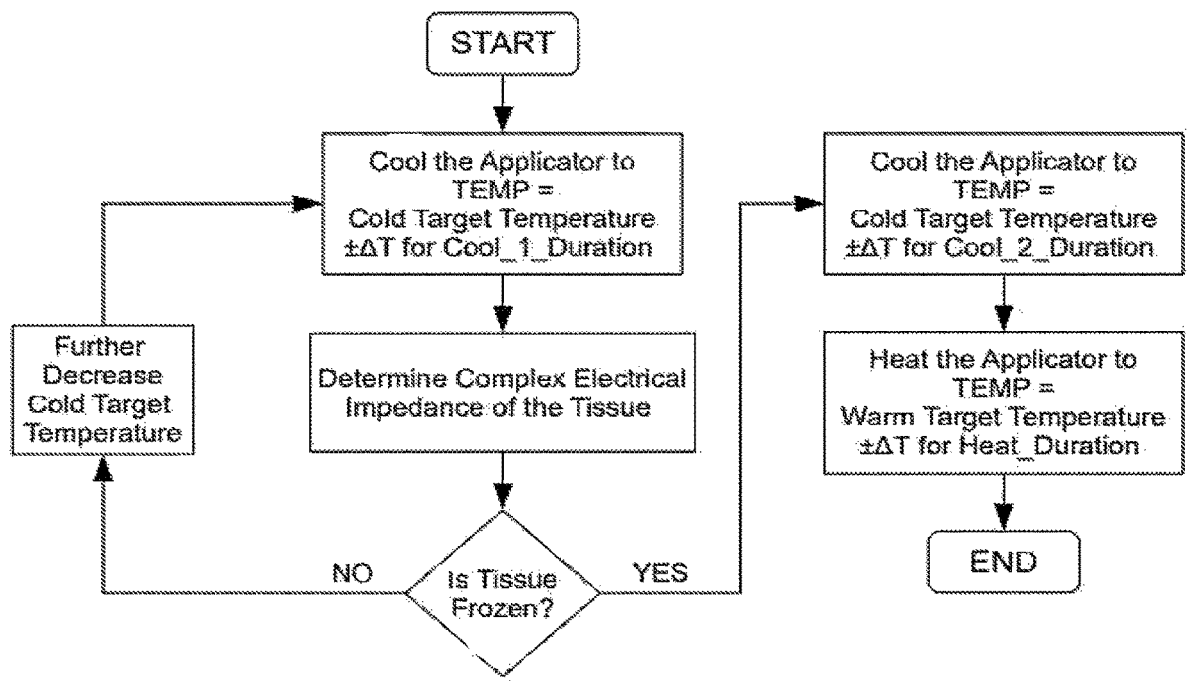
Figure 43L:
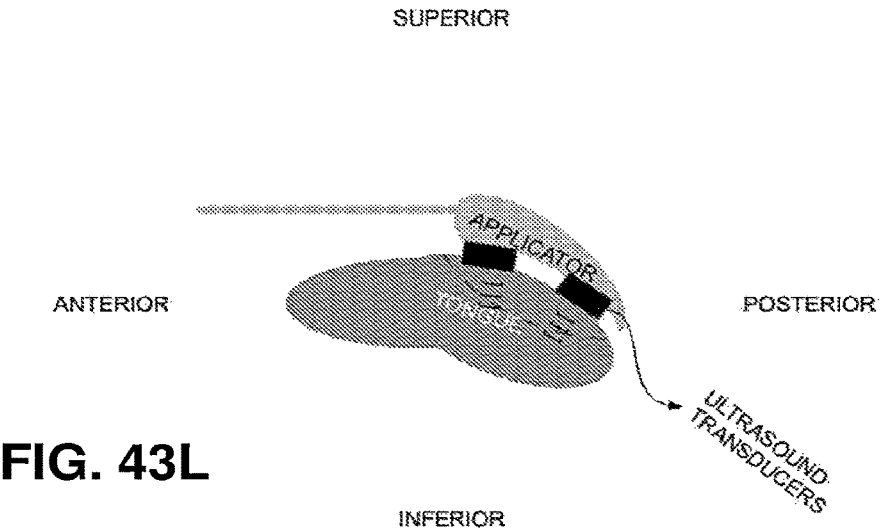
Figure 43M:
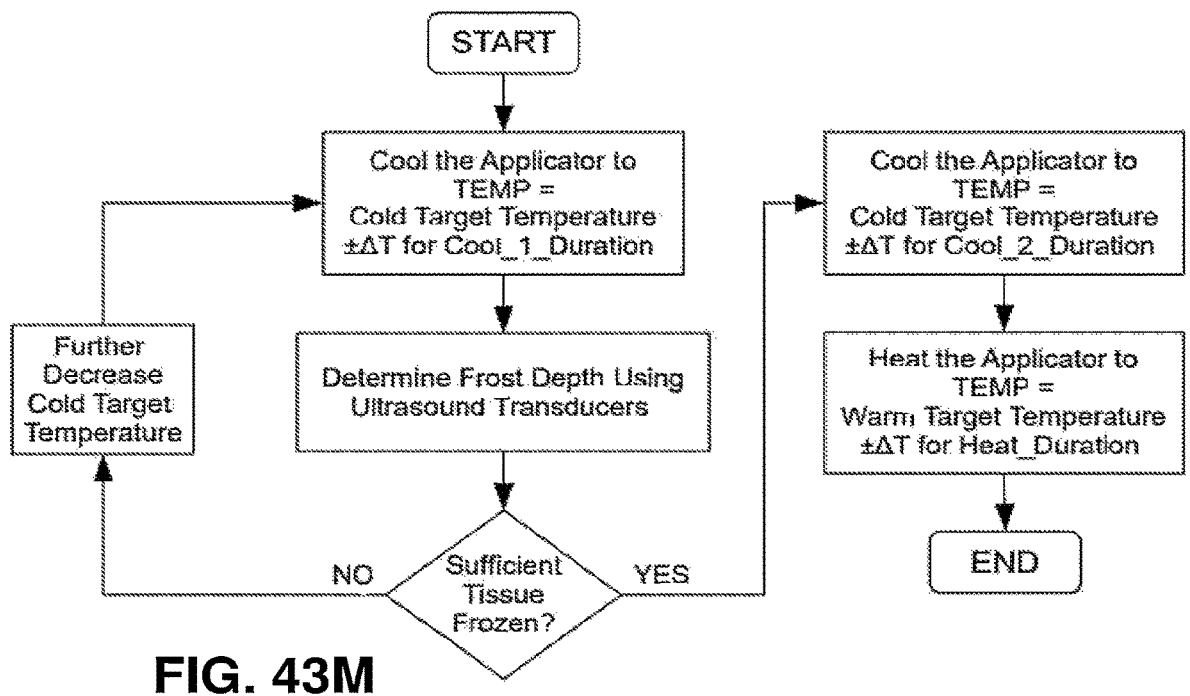
Figure 43N:
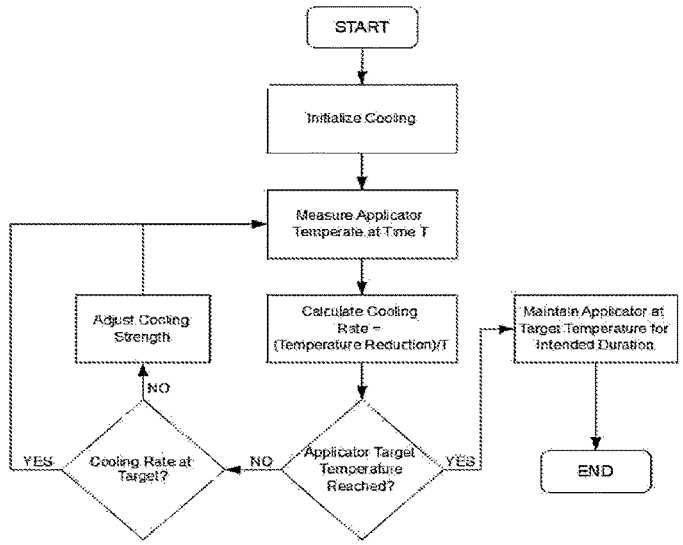
Figure 43O:
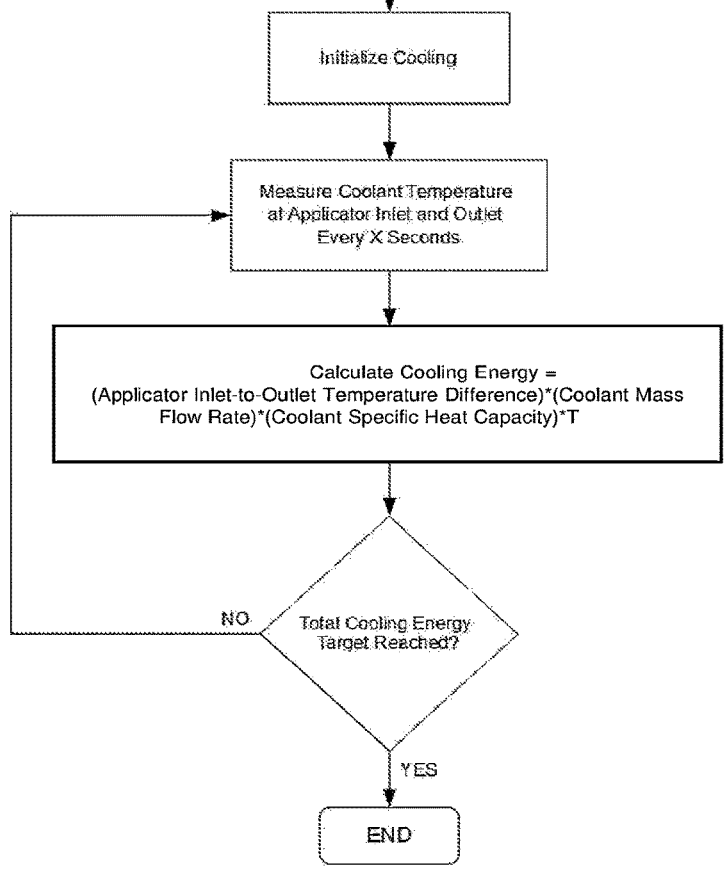

FIGS. 43A-43O illustrate various feedback algorithms for the control system and their possible configurations for base of tongue treatment.

FIGS. 44A-44D illustrate control algorithms for regulation of the temperature determinant.

Figure 45:
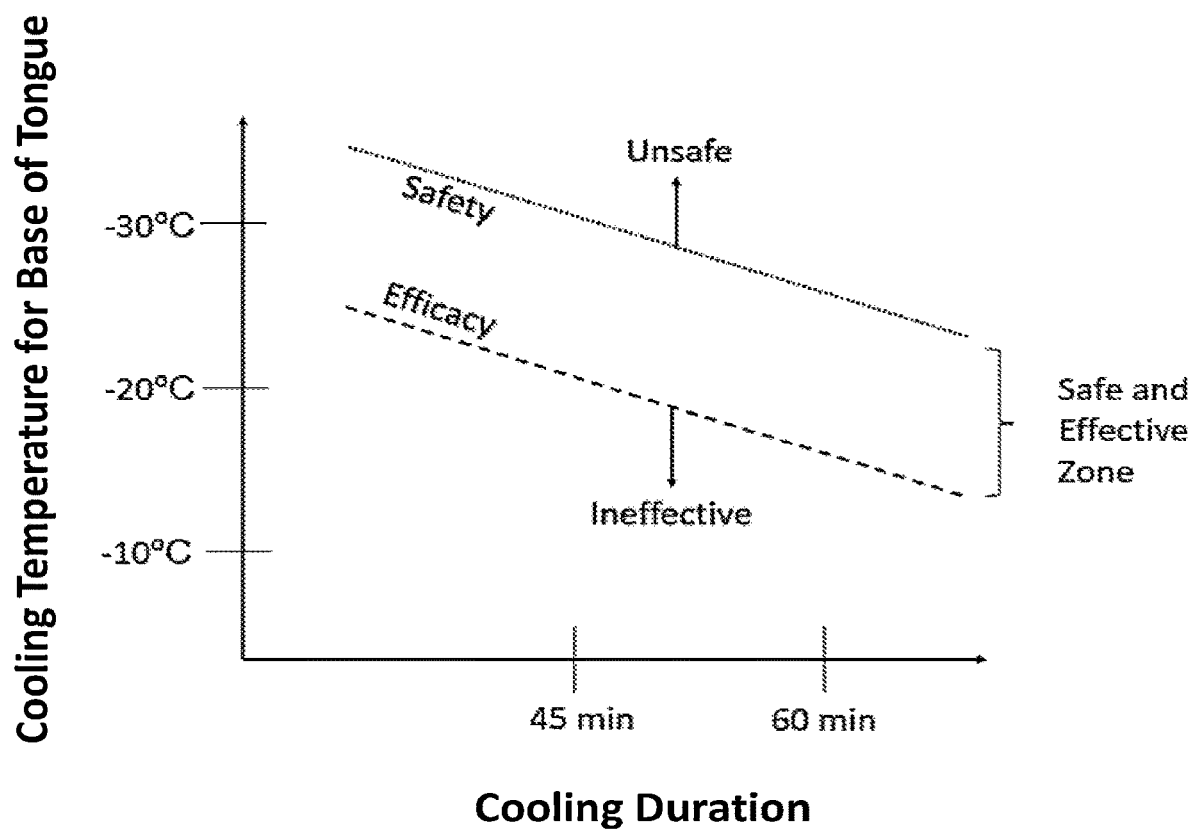

FIG. 45 illustrates the strength duration curves for the safety and efficacy of the therapy.

Figure 46A:
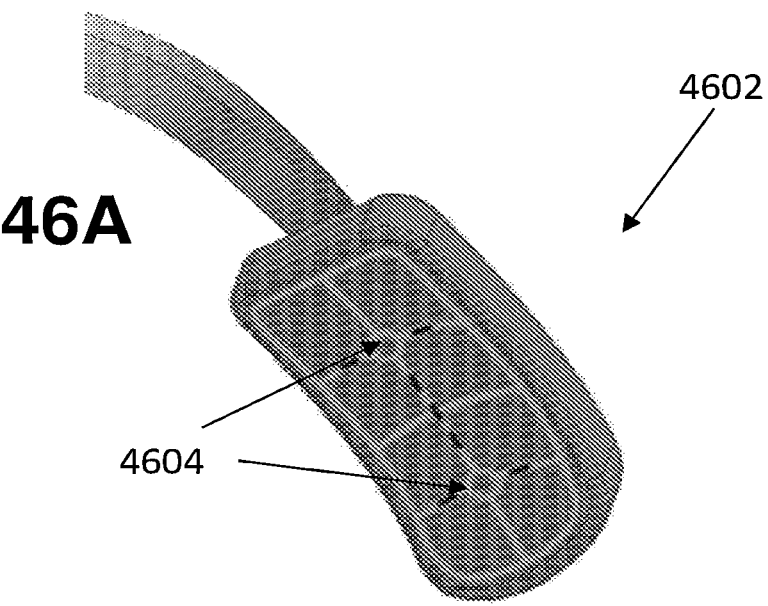
Figure 46B:
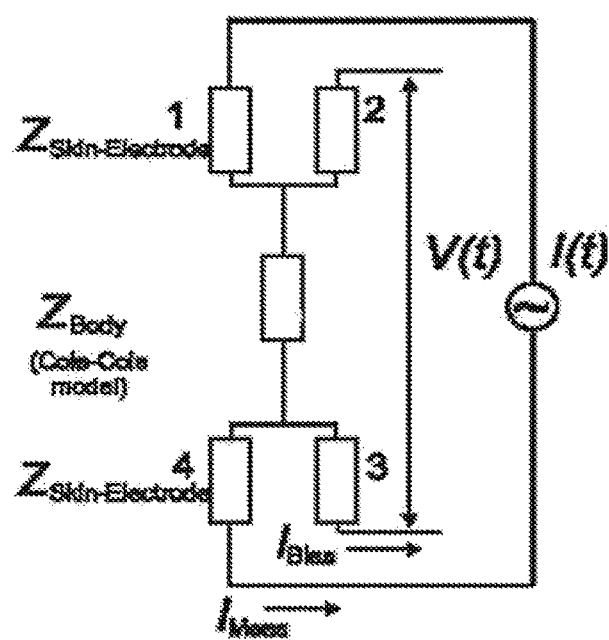

FIG. 46A-46B illustrates a device that uses bioimpedance measurements to predetermine if a patient is suitable for treatment.

Figure 47A:
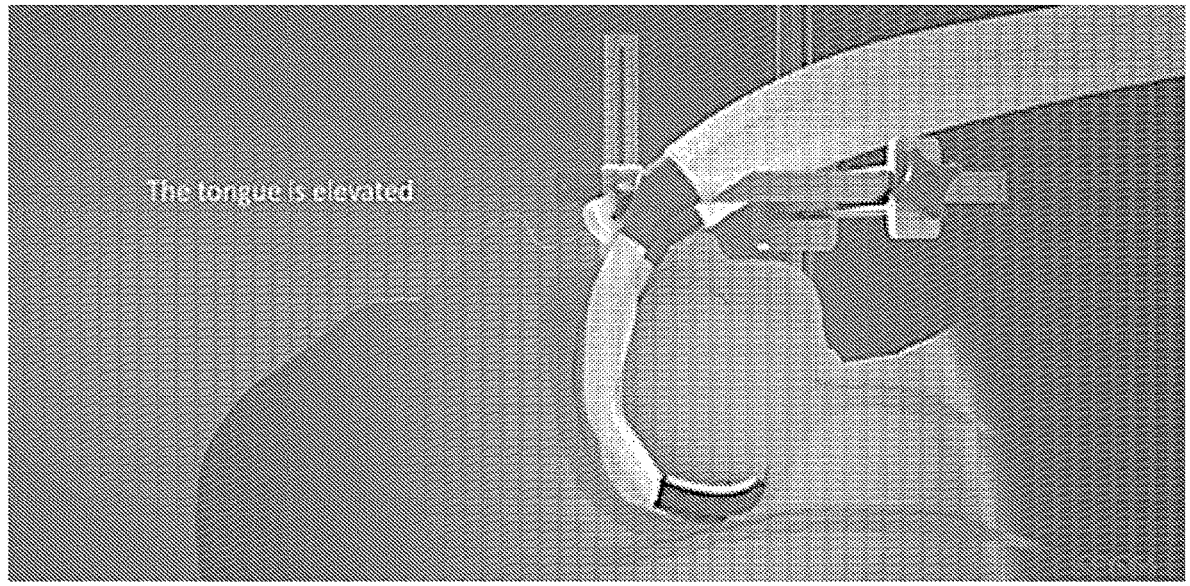
Figure 47B:
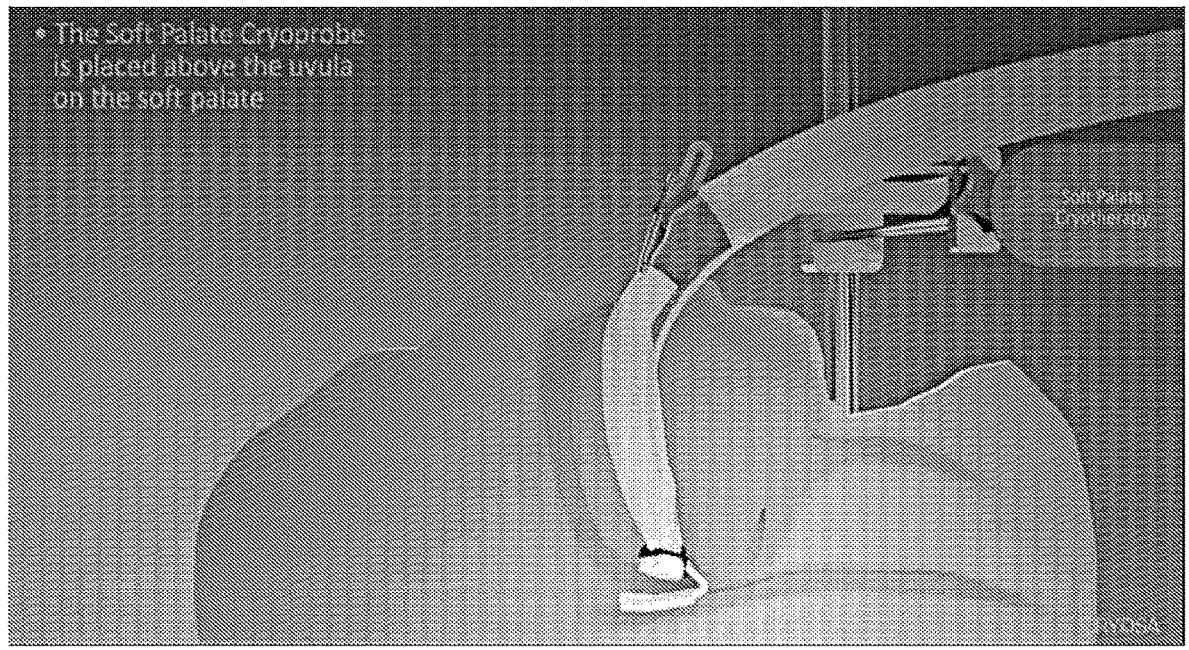

FIG. 47A-47B illustrates the sequential steps of the clinical procedure a patient undergoes with the obstructive sleep apnea treatment system.

Figure 48:
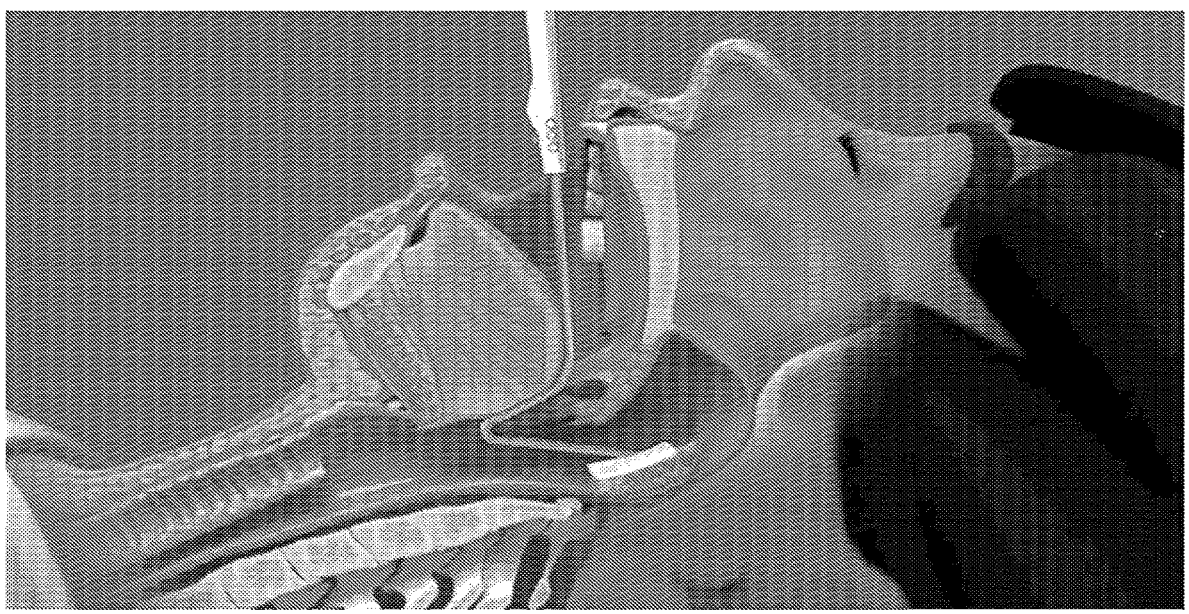

FIG. 48 shows the implementation of an Applicator used for adenoid removal.

DETAILED DESCRIPTION

Provided herein are devices and methods to treat obstructive sleep apnea. A sleep apnea treatment system 100, illustrated in FIG. 1A, can include four major components: an oral Applicator, a cryoprotectant, a temperature determinant, and a controller. The following description provides details and examples of design and operation of the overall system and its individual components. Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the teachings of the present invention, and the invention includes all such modifications.

Figure 1A:
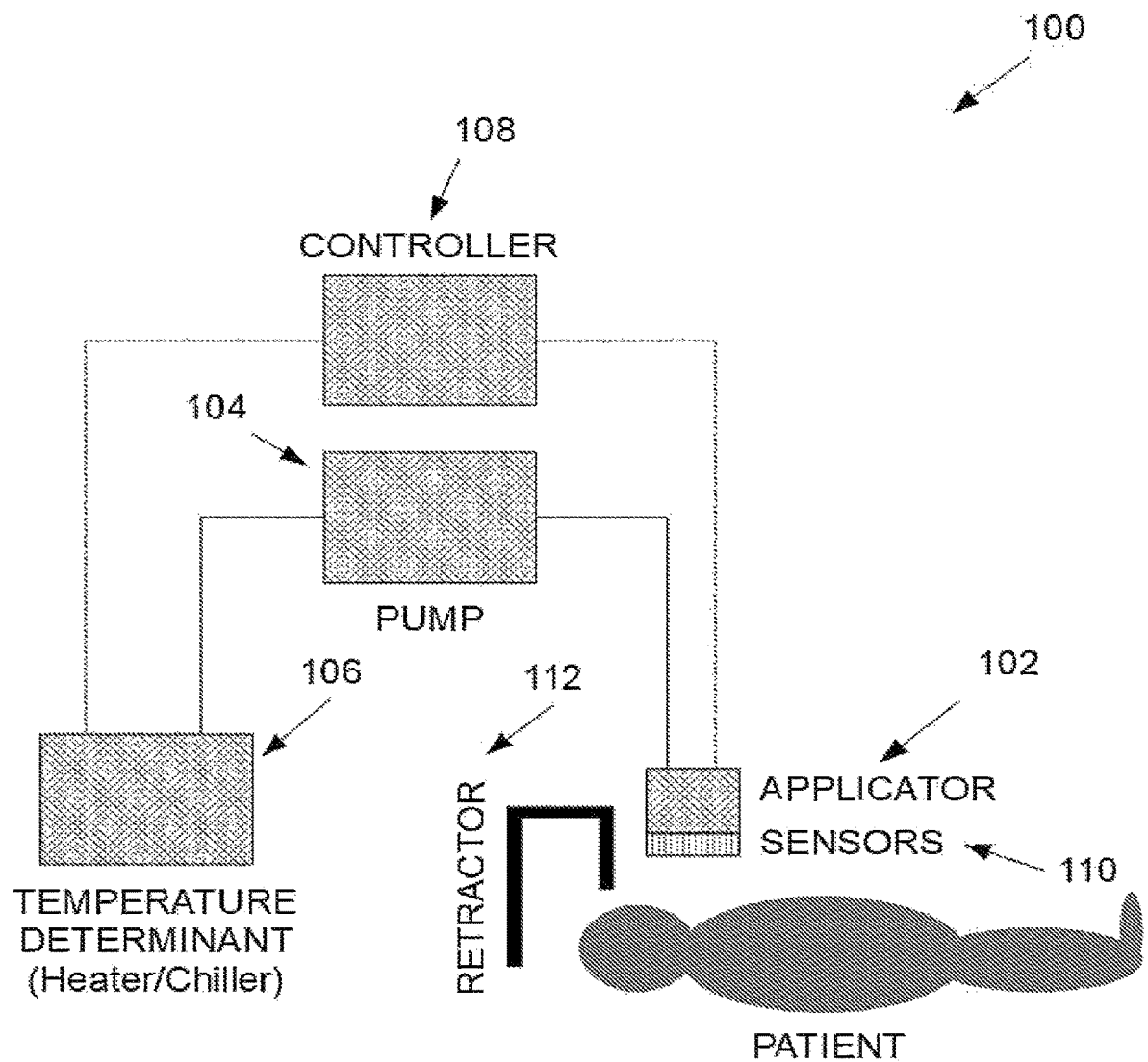
FIGS. 1A-1C illustrate embodiments of a sleep apnea treatment system.

FIG. 1A demonstrates one overall configuration of a sleep apnea treatment system 100 in a clinical setting, in which a controller 108 is connected to a temperature determinant 106, which has one or more lines connected to an oral Applicator 102. These lines to the Applicator may be connected or disjointed. In some embodiments, the lines may be connected by an additional line, incorporating a valve with the connection to turn on and off flow through this channel. In some implementations, the system can be configured to run a pre-cooling agent through the lines before treatment to ensure that the temperature throughout the lines is uniform and not effected by the temperature of the lines itself The temperature determinant 106 can be configured to store, generate, or produce a chilled or heated medium via a pump 104 to the Applicator. For example, the temperature determinant can be a simpler refrigerant chiller that couples the cold to a recirculating fluid that goes through the Applicator. In another embodiment, the temperature determinant can also be a Peltier device, either positioned locally on the chiller temperature probe or remotely from the Applicator, whereby the Peltier device chills a recirculating fluid that goes through the Applicator. In this example, there can also be a secondary loop of coolant to cool the Peltier device. Gas expansion systems could also be used by allowing a compressed gas to expand in or near the Applicator resulting in rapid cooling. In some examples, the temperature determinant can be a heating device configured to provide a heated gas or fluid to the Applicator.

The controller 108 can be an electronic controller governed by a human operator or computer/CPU system and be configured to control the overall operation of the system 100. The intricacy of the controller 108 can contain a control system with operations that range from very basic to very complex. In the most basic installments, the control system may only control and stabilize the temperature of the temperature determinant 106. In another example, the control system may prompt the user for the steps of the procedure (such as switching from cooling to heating), and issue warnings when the sensor measurements are out of range, requiring manual input to change the incorrect parameters. In more advanced installments, the controller may govern the main operations of the system, including turning on/off the pump, facilitating the outputs of pump speed, chiller temperatures, and heater temperatures, and terminating the therapy at the end of the session or in case of an anomaly. In the case where the control system is the most governing, the controller regulates the system based on feedback data from one or more sensors of the system and calculating overall system time constants, working as a PID system, allowing the controller to individualize the patient's treatment, which will be described in more detail below.

The controller 108 may run operations based on measurement and guidance systems within the sleep apnea treatment system, or simply output data for interpretation by the operator. This measurement system can consist of multiple sensors located on or within the devices of the heater/chiller and the Applicator. The measurement system may collect information consisting of fluid flow rate, fluid pressure, temperatures of the chiller, heater, or Applicator, Applicator pressure on the tissue, contact detection, etc.

The Applicator of the sleep apnea treatment system is designed and configured to be placed either interiorly or exteriorly to the oral cavity of the subject. The Applicator is the part of the system that is in direct contact with the target tissue or tissues of the patient to be treated. In some examples, the Applicator is constructed using metal, plastic, or ceramic components and can be sanitized or sterilized before use. The Applicator can be rigid or flexible, depending on the target tissue. Furthermore, the Applicator can also be reusable or disposable. The Applicator is designed and configured to both remove and deliver heat at rates in the range of 0.2 Watts to 95 Watts to and from the tongue of a patient for a period of 1 minute to 100 minutes. The Applicator can include one or more sensors 110 which can include, for example, temperature sensors, flow sensors, pressure sensors, etc. A retractor or fixture arm 112, which will be described in detail below, can be configured to hold the Applicator in place adjacent to a patient during treatment.

In some embodiments, the Applicator is composed of multiple parts. Each part of the Applicator may be connected to another part of the Applicator or may be independent of the other parts of the Applicator. Each part of the Applicator is capable of extracting heat and/or delivering heat from the tissue segments that it gets in contact. Furthermore, each segment could be different shape and size, and maybe designed to treat different parts of the tissues in the oral cavity. The Applicator may also have external markings to indicate the Applicator's midline to assist in proper placement in the oral cavity. These external markings should be colored to be easily visible in the oral cavity. For example, green and blue do not produce glare or blend in with the surrounding tissue, whereas red, white, and black may cause the external markings to become indistinct once inside the patient's mouth. Coolant flow to these individual parts of the Applicator could be configured to be in parallel, series or in combination of parallel or series. Furthermore, the design of each Applicator part may be different. For example, the Applicator part that is treating the tongue could be a rigid metal device while the Applicator part that is treating the lateral walls could be balloon type.

Since the anatomy of the oral structures vary from subject to subject, it is advantageous to design a range of Applicators and select the one that is most suitable for a given patient. Alternatively, the Applicator can be made from a compliant or a deformable material. In one embodiment of the invention, the Applicator is a constructed using a soft and stretchable elastic material, allowing it to have characteristics of an inflatable balloon. In that case, the balloon is initially advanced into place in the oral cavity and then inflated using a warm fluid to make sure that it makes firm contact with the surfaces. Afterwards, the fluid is chilled while maintaining the pressure to deliver the cryolysis therapy. At the end of the treatment period, the liquid that is in the Applicator is warmed and the Applicator is deflated before its removal. In some embodiments of the invention, the compliant balloon has uniform thermal conductivity and delivers the therapy to all surfaces that it comes in contact with. In other embodiments, the balloon has thermal insulation features, consisting of different materials and thickness at different sites, or additional air-filled chambers, to form thermal insulation to protect the oral structures that are not supposed to experience cold temperatures.

In any of the embodiments disclosed herein, the applicator and source of cooling fluid are configured to cooperatively cause cooling of a target oropharyngeal tissue when placed in contact with the target surface of the oropharyngeal tissue. Furthermore, the applicators and/or engagement member(s) of the applicators are configured to be cooled to a temperature sufficient to cause cryolysis of adipose tissue within the target oropharyngeal tissue.

Figure 1B:
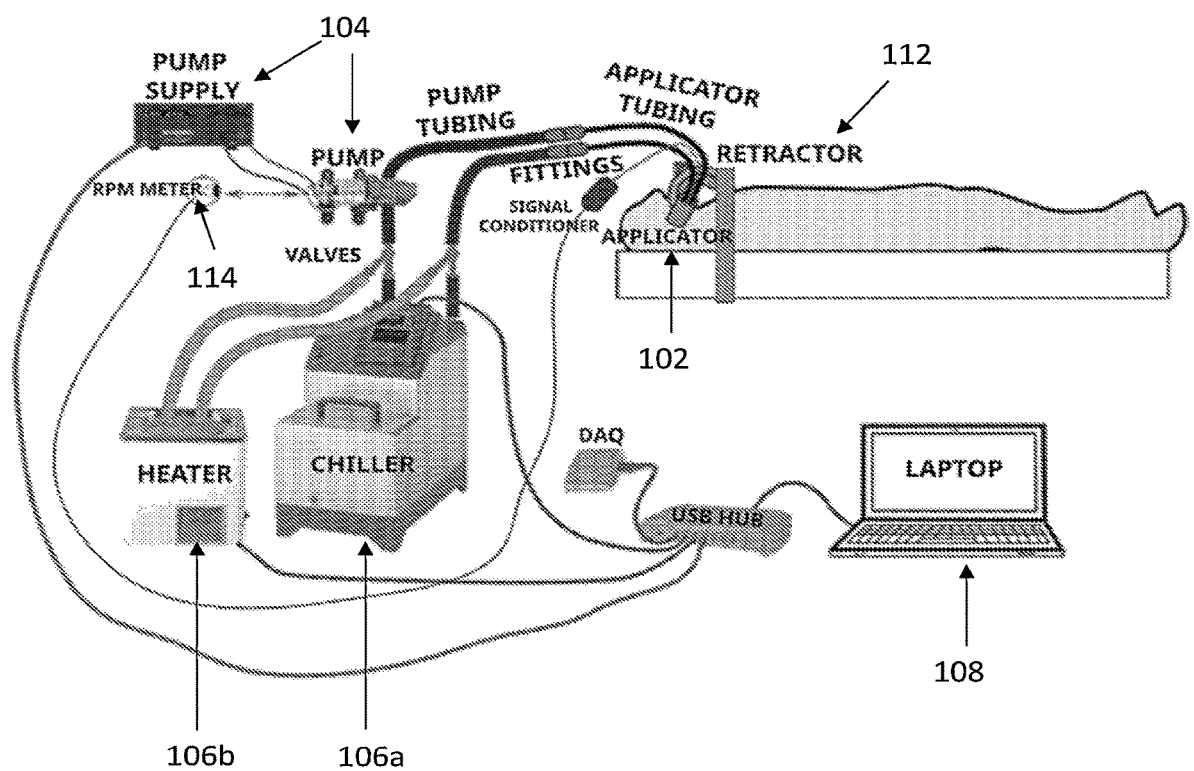
Figure 1C:
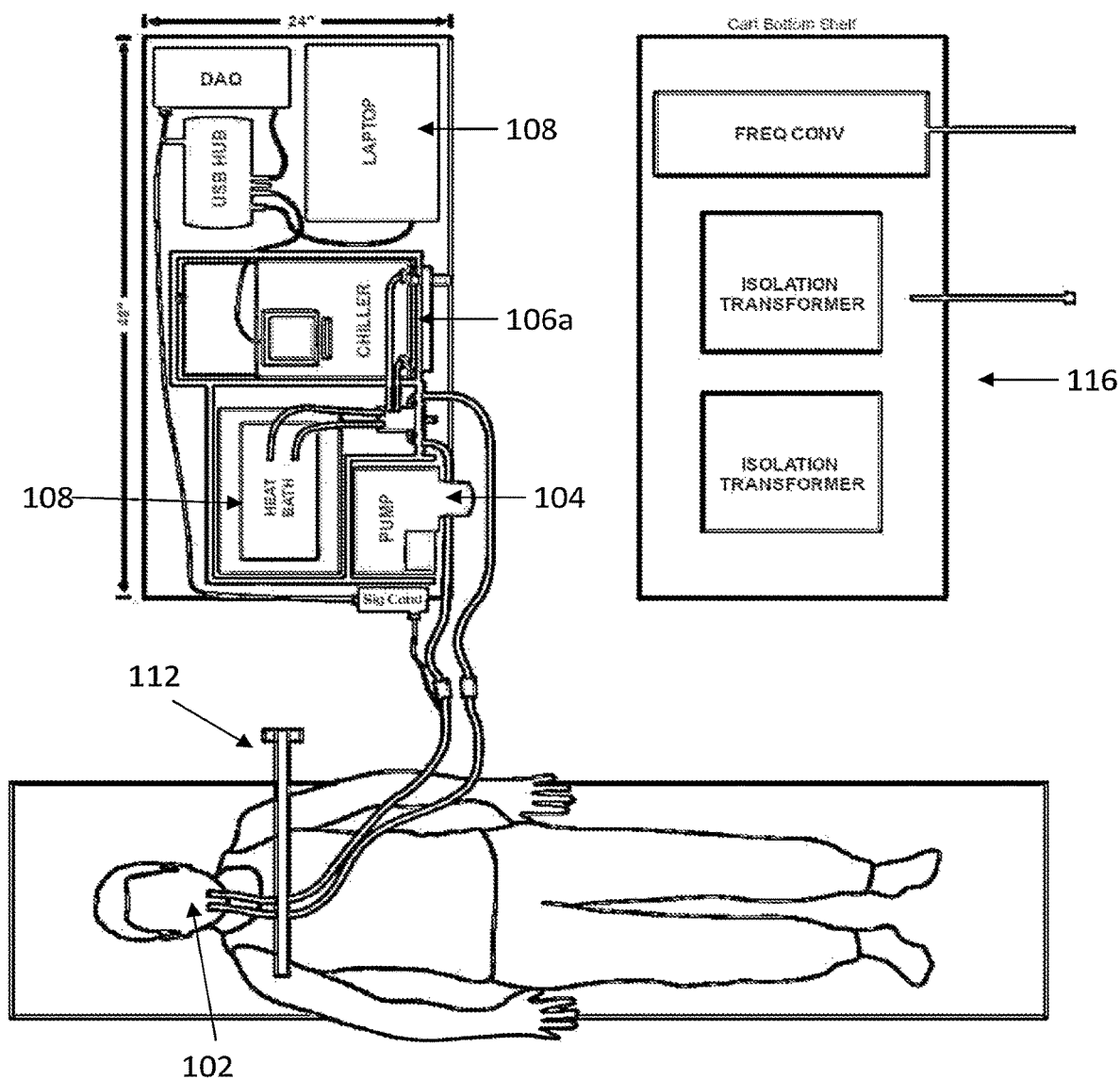

FIGS. 1B-1C is another embodiment of a sleep apnea treatment system, including at least an applicator 102, at least one pump/pump supply 104, a chiller 106a, a heater 106b, a controller 108 (e.g., a laptop or other computing device), and a retractor 112 as previously described. A flow sensor such as an RPM meter 114 can be used for monitoring of the fluid flow rate during a given treatment session. In some embodiments, the flow sensor or RPM meter can be incorporated into the pump/pump supply. If the tissue temperature is warmer than the desired one (e.g., as measured by a temperature sensor in contact with the tissue or the applicator surface), then the operator or the system (e.g., the controller) can increase the fluid flow rate, i.e., the pump RPM, to increase the heat extraction rate. Conversely, the operator or the system/controller can reduce the RPM to decrease the heat extraction, and in return the tissue temperature increases. The system shown in FIG. 1B shows the temperature determinant as separate heater 106b and chiller 106a with two separate tubes for delivery and removal of the heated/chilled medium from the temperature determinant to the Applicator. The system of FIG. 1B further includes fluid flow monitoring with a pump RPM counter and an in-line flow meter. A controller 108 (shown as a laptop) can be used for data acquisition, timing therapy duration, monitoring temperatures, governing temperature of the temperature determinant, and medical billing. The retractor system can be configured to position the Applicator, maintain a constant force/pressure over the tissue, and aid with visualization.

FIG. 1C shows another view of the system of FIG. 1B, and can include additional electronics 116 disposed in the cart, including but not limited to a frequency converter and one or more isolation transformer(s).

Figure 2A:
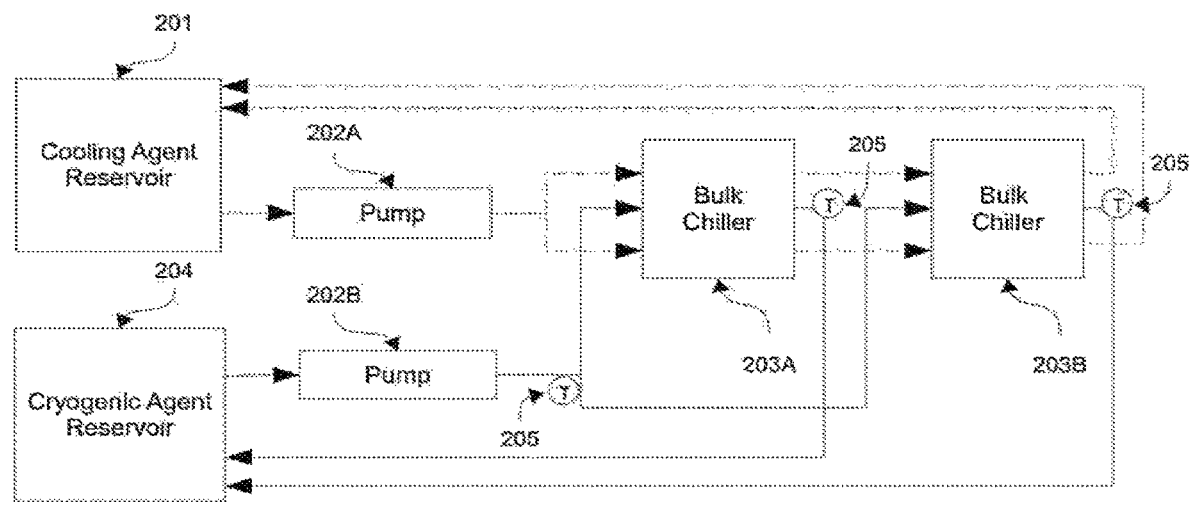
FIGS. 2A-2C illustrate the mechanics of an optional bulk cooling system.
Figure 2B:
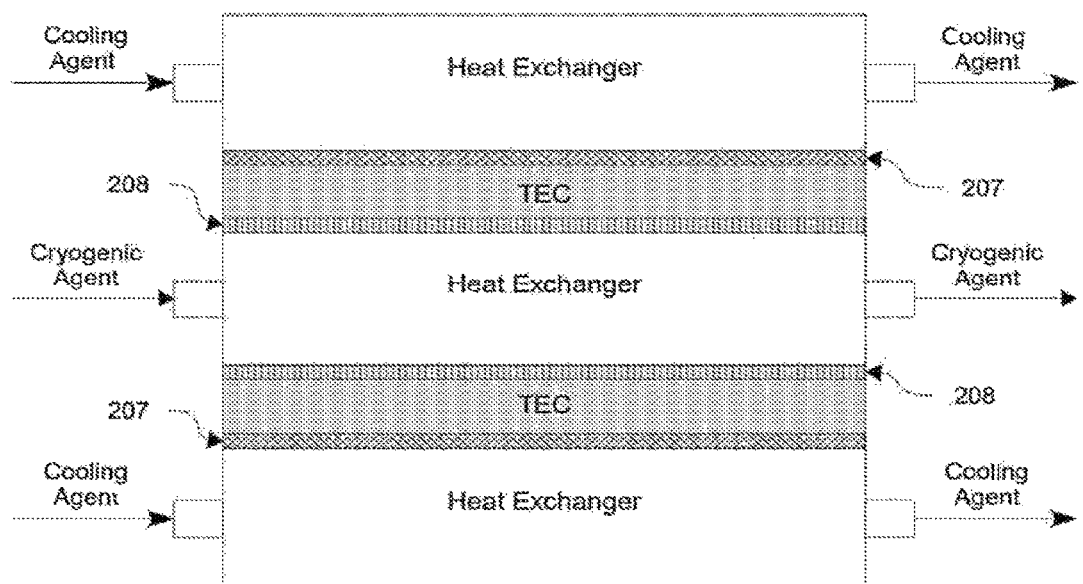
Figure 2C:
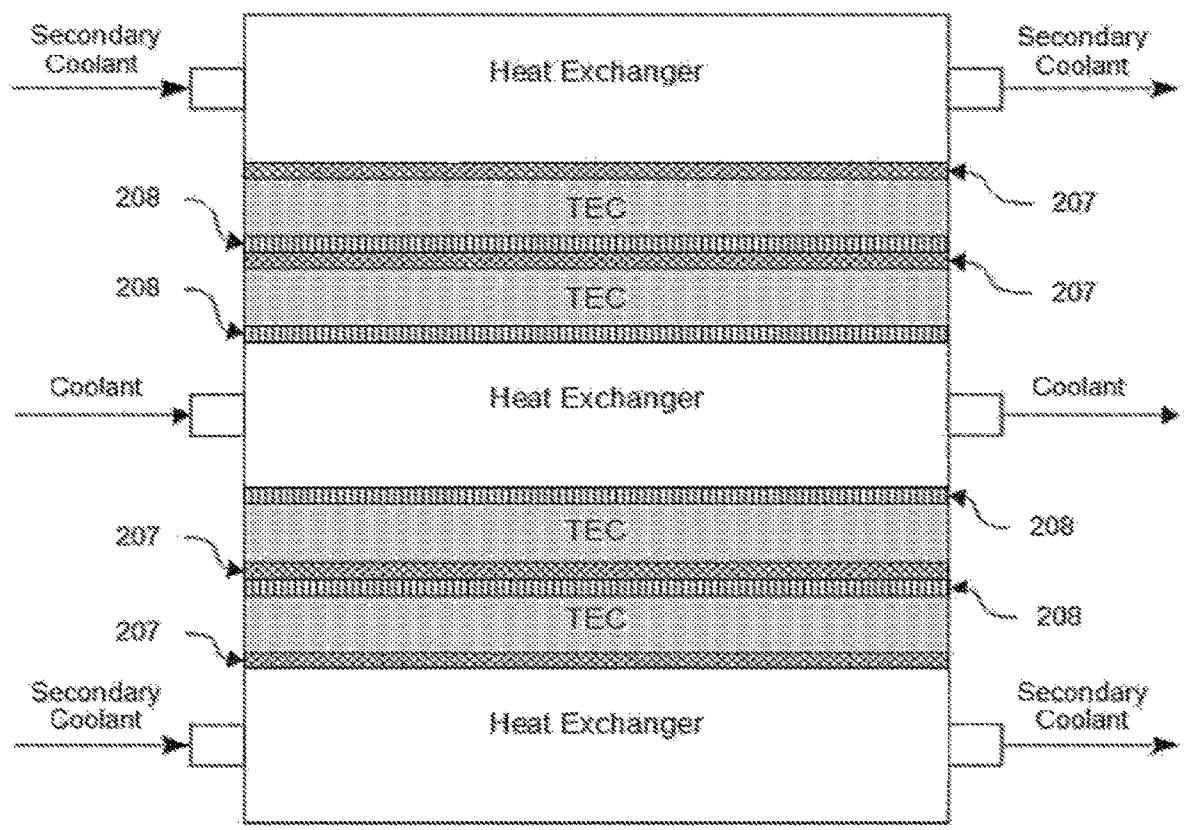

FIGS. 2A-2C illustrate one embodiment of the mechanics of a bulk cooling system configured to optimize the chilling of a cryogenic agent for a sleep apnea treatment system. An insulated or non-insulated reservoir 201 containing liquid with preferably high heat capacities such as water, glycol/water solutions, or dielectric fluids is connected to a pump 202A to transport the fluid to the inlets of the bulk chiller 203A via tubes. The cooling agent is then pumped out of the bulk chiller 203A via outlets to be transported to similar inlets of another (optional) bulk chiller 203B. In different embodiments, there may be one or more bulk chillers, depending on factors such as the desired temperature of the cryogenic agent. Once through the bulk chiller 203B the cooling agent flows back into the reservoir 201 to continue circulation.

An insulated reservoir 204, such as a Dewar flask, containing cryogenic agent is also connected to a pump 202B to transport the cryogenic agent to the inlet of the bulk chiller 203A and 203B, concurrently to the circulation of the cooling agent from reservoir 201. The cryogenic agent then exits the bulk chiller 203A and bulk chiller 203B to return to the reservoir 204 and continue circulation. In the illustration of FIG. 2A, the cooling agent circulates through the bulk chillers connected in series, whereas the cryogenic agent circulates through the bulk chillers 203A/B connected in parallel. This particular implementation allows the maximum amount of heat transfer from the cryogenic agent to the cooling agent, which in turn facilitates the cooling of the cooling agent itself. For example, the cryogenic agent could be a mixture of ethanol and water, and the cooling agent could be water. Other examples of cryogenic agents are as follows: A mixture of 75.5% ethanol ($C_2H_6O$) and 24.5% water ($H_2O$) (v/v), a mixture of 80% hexyl acetate ($C_8H_{16}O_2$) and 20% ethanol ($C_2H_6O$), a mixture of 80% heptyl acetate ($C_9H_{18}O_2$) and 20% ethanol ($C_2H_6O$), as well as other compounds or mixtures of compounds that show low viscosity ($\eta$), such as 5 µ Pa·s or lower at cold temperatures, such as −40° C. This system allows the transfer of heat from the cryogenic agent to the cooling agent. In this example, one can assume that the cryogenic agent would be brought to temperatures of −40° C. Heat extracted from the cryogenic agent as well as the heat produced by the TECs as a result of their self-heating would increase the temperature of the cooling agent. The cooling agent will need to be cooled back again for the next cycle, and that is done by dissipating its heat into the ambient environment, most likely to the air in the room. To improve the heat dissipation, highest temperature gradient between the cooling agent and the room temperature is desired. Since the room temperature is usually fixed around +20° C., it would be advantageous to increase the temperature of the cooling agent, which is accomplished by two bulk chillers connected in series. In different embodiments, the cooling agent and cryogenic agent may flow through the bulk chillers 203 in parallel or series. In addition to, one or more thermistors or temperature sensors 205 may be placed throughout the circulation of the cooling agent or the cryogenic agent. Preferably, a thermistor or temperature sensor 205 would be placed before and after the cryogenic agent passes through the bulk chillers 203A/B to compare the temperature differences of fluid exiting each bulk chiller.

FIG. 2B details one embodiment of the mechanisms for a bulk chiller. The bulk chiller in this embodiment can describe details of the bulk chillers 203A and 203B described above. A bulk chiller may include, for example, three heat exchangers with two thermoelectric coolers (TEC) placed between them. The heat exchangers allow fluid to be passed through via an inlet and outlet. The outermost heat exchangers are in contact with the hotter side of the TEC 207 as the cooling agent flows through the heat exchangers in order to provide a heat sink for the TEC. As the cooling agent flows through the outermost heat exchangers, the cryogenic agent flows through the innermost heat exchanger, which is surrounded with the cooler side of the TEC 208 to properly chill the cryogenic agent.

In the embodiment FIG. 2C of the bulk chiller, any number of TECs may be stacked between the heat exchangers. The TECS can be stacked in order to improve the TECs heat pumping capacity by reducing the temperature differential across each individual TECs, thus chilling the coolant faster. As shown in the embodiment of FIG. 2C, when multiple layers of TEC are implemented, the hotter side of a first of the TECs 207 can be placed next to, adjacent to, or in contact with the cooler side of a second of the TECs 208. While the embodiment of FIG. 2C shows two TECs between heat exchanger layers, it should be understood that any number of TECs can be implemented in other embodiments.

Figure 3:
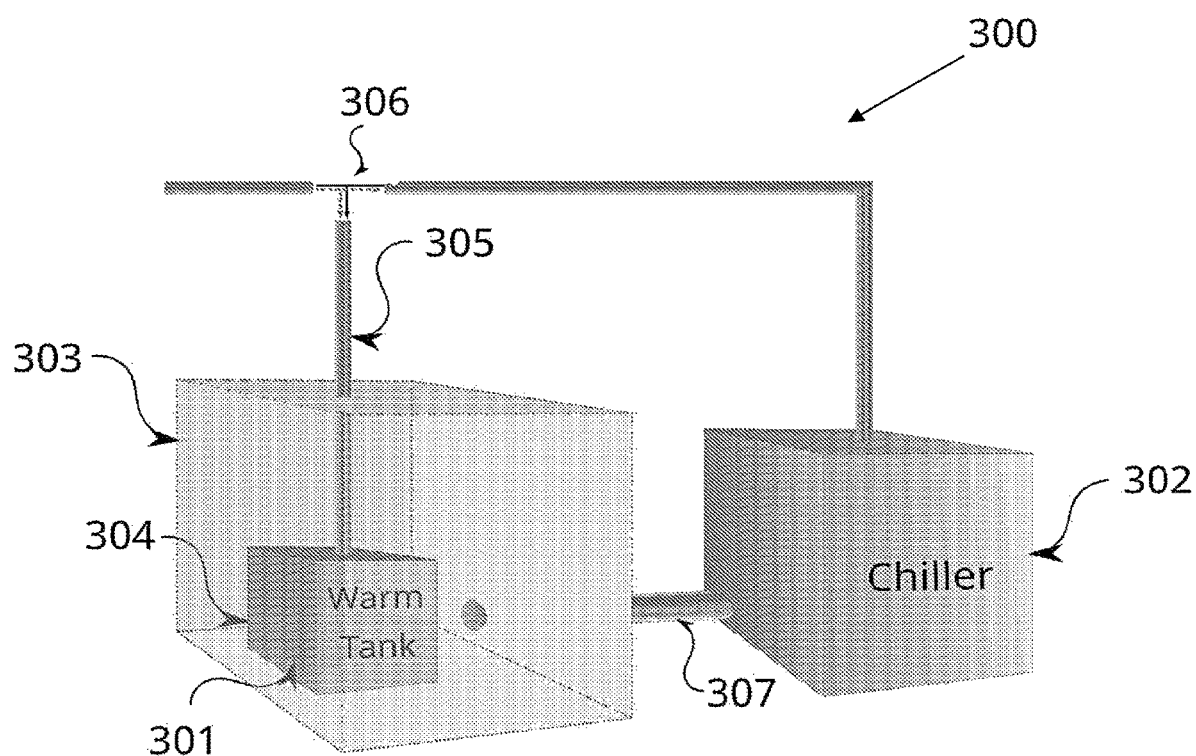
FIG. 3 illustrates one example of an optional configuration for heating the warm tank using the thermal discharge of the chiller.

FIG. 3 illustrates an embodiment of a temperature determinant system 300 comprised of a heater 301, chiller 302, and enclosure 303 to improve the efficiency of the warming tank 304. Similar to previous embodiments, the chiller 302 and warming tank 304 have fluid lines 305 to dispense coolant or a warm fluid to the Applicator, with a valve 306 to switch between administration of different fluids. A heater 301 is placed within the warming tank 304 and the warming tank 304 is surrounded by an enclosure 303 connected to an exhaust line 307 that feeds the chiller exhaust to the enclosed area, allowing the thermal energy produced by the chiller 302 to heat the warming tank 304. The enclosure is preferably made of material with a higher R-value, such as fiberglass or polystyrene.

The Applicator of the present disclosure can include one or more pieces, e.g., top and bottom, machined out of a metal or other suitable material such as aluminum, plastic, or stainless steel, and combined by screws, adhesive, or other similar techniques.

Figure 4:
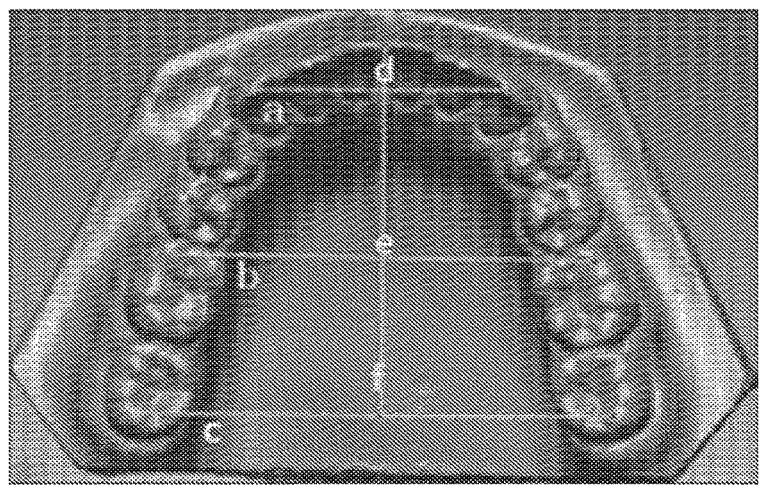
FIG. 4 illustrates one example of various dimensions of an Applicator based on the mean dimensions of a human patient's mouth.

FIG. 4 illustrates one example of various dimensions of an Applicator based on the mean dimensions of a human patient's mouth. The size of the tongue, and thus the size of the Applicator, is limited by the size of other oral structures. Applicators according to the present disclosure can be designed at different sizes, including having widths ranging from 20 mm to 40 mm and so on. Alternatively, the Applicator can be designed small enough to fit the majority of the population, e.g., 90%.

FIGS. 5A-5D illustrate various embodiments of an Applicator 502 that may be used to administer coolant to different areas of the oral cavity. The embodiment of FIG. 5A demonstrates one example of an Applicator used to apply coolant to the base of the tongue. The face of the Applicator may have a curvature that allows conformity to the base of the tongue so that the coolant may be administered evenly to all intended areas of the tongue. The face of the Applicator is intended to be placed midline to the tongue, but exact placement is dependent on the patient's needs and may be placed off kilter. The inlet and outlets of the Applicator that the coolant is administered through are located at the top of the Applicator in order to fit the curvature of the device. In addition, the handle that the Applicator of FIG. 5A is attached to may have a curvature similar to the oral cavity and pharynx region to allow proper placement of the face of the Applicator to the base of the tongue, in order to keep the patient comfortable and have more ease of use for those operating the device.

The embodiment of FIG. 5B demonstrates one example of an Applicator intended for reaching the retropalatal region of the oral cavity. The face 504 of the Applicator of FIG. 5B can be slightly curved and smaller in size to accommodate the curvature of the retropalatal region. The inlet and outlet tubes of the Applicator may be located directly behind the Applicator face to allow for a compact design, in addition to an Applicator handle located in-between the inlet and outlet tubes. This Applicator handle can be used to place or tilt the face of the Applicator in the desired treatment region. In some embodiments, an angle between the handle and the Applicator is adjustable, allowing the Applicator to rotate or articulate so as to better conform with the anterior surface of the soft palate. For example, the adjustment can be done with a set screw or a spring-loaded friction hinge 506.

As it is shown on FIG. 5C, the embodiment may contain an insulator positioned between the soft palate and the posterior wall. The use of an insulator can be configured to prevent the palate from being loose and being pressed against the posterior wall when the applicator is placed against the palate. The presence of the insulator also prevents the posterior wall from being exposed to any undesired cooling.

The embodiment of FIG. 5D demonstrates an Applicator 502 configured for reaching the lateral fat pads of the oral cavity. The Applicator 502 of FIG. 5D may have multiple applicator faces 509a and 509b for the different treatment zones of the lateral fat pads. As shown, the applicator faces 509a and 509b can be directed in opposite directions. These Applicator faces may actuated or pressed against the lateral fat pads with the desired pressure by way of the Applicator handle 508 which may comprise, for example, a scissor-mechanism including a hinge 510. Actuation of the handle 508 can cause the applicator to pivot at hinge 510, causing the applicator faces 509a and 509b to move apart to contact the opposing lateral fat pads. The Applicator handle of FIG. 5D can allow the desired pressure to be administered to the lateral fat pads by moving the two handles either closer together or further apart. Once the desired position of the Applicator is met, a latch may be locked to secure the position of the lateral fat pads face Applicator for treatment. The inlet and outlet tubes of the Applicator can be located directly behind the Applicator, located close to the handle to provide a compact design.

FIGS. 6A-6B illustrate one example of an Applicator half that includes a fluid flow channel. The fluid flow channel within the Applicator can be designed and configured such that it maintains a relatively constant cross section from the inlet to the outlet of the Applicator. The inlet and outlet are designed to receive and return a chilled or heated medium from the temperature determinant. In one embodiment, the average width of the channel is 5 mm and the average height is 3 mm. This design allows the fluid to flow at a relatively constant rate within the Applicator without having large fluctuations in the pressure and flow rate, which in turn minimizes the temperature variations on the Applicator surface while providing uniform heat extraction from the tissue.

Referring to FIGS. 7A-7B, in addition to the fluid channel that is in the Applicator, the other half of the Applicator can include two ports for making attachments to the fluid inlet and outlet tubes. This design allows the placement of one or two pairs of temperature sensors, typically thermistors, to sense the temperature of the fluid at the inlet and the outlet.

Additional passages can be provided on the Applicator to allow the placement of the sensors on the bottom surface of the Applicator, such that the wiring for these sensors can come from the top side of the Applicator, as it can be seen in FIGS. 8A-8B. These sensors may be connected to the arm of the Applicator by way of an electrical circuit, for example, an incorporated flex circuit within the arm of the device. In this implementation, although the passageways for the wiring allow the travel of the wires for the temperature sensors from the top side to the bottom side, these passageways are not in contact with the fluid channel that is within the Applicator.

FIG. 9 shows one example of the placement of temperature sensors in and around an Applicator. Briefly, a cryoprotectant combination (CPC) which will be described later, is placed around the Applicator. In FIG. 9, the CPC is shown as the cross hatched area. Inline temperature sensors, such as S1, can be used to measure the temperature of the fluid that is passing through the inlet and outlet ports of the Applicator. Block surface temperature sensors, such as S2, can be used to measure the temperature of the Applicator surface while the tissue temperature sensors such as S3 are used to measure the surface temperature of the tongue. In some embodiments, silicon may be placed in between the sensors and Applicator face. While the block temperature sensors can be adhered to the surface of the Applicator, the tissue temperature sensors may be stitched to the fabric of the cryoprotectant combination (CPC). Although there is no limit to how many temperature sensors can be used, in one example 5 sensors can be used in the Applicator and CPC.

The Applicator bottom surface (e.g., tissue contacting surface) can have many shapes. In one embodiment, shown in FIG. 10A, the curvature of the device along its long axis is such that it has a concave surface with decreasing radius of curvature (more curved) toward the distal end, which is configured to be placed in the posterior part of the mouth. In this embodiment, the cross-sectional view of the Applicator along its short axis, which is parallel to the coronal axis of the body when the device is placed in the mouth, has a convex curvature. This design allows the Applicator to press down on the tongue and make firm contact with the tongue tissue. The typical long axis length of the Applicator is 45±30 mm and short axis length of 28±18 mm.

In another embodiment, shown in FIG. 10B, the curvature of the applicator 1002 along its long axis is longer and more concave in curvature than that of the applicator in FIG. 10A to conform to the shape of the human tongue to increase effective contact area. In this embodiment, the width of the Applicator is configured to taper to the distal end of the device to reach into the vallecula while not obstructing the endotracheal tube. In some embodiments, the distal end can taper to a distal tip, as shown. Due to the increased concavity of this Applicator, the tongue would be more depressed to potentially enhance deeper fat treatment. The typical long axis length of the Applicator is 50±40 mm and short axis length of 20 mm±18 mm, allowing this Applicator to be more suitable for smaller oral cavities. Referring still to FIG. 10B, the applicator 1002 can include a first portion 1004 generally configured to contact the tongue, and a second portion 1006 generally configured to contact the base of the tongue and reach into the vallecula without obstructing the endotracheal tube. For purposes of this disclosure, the tongue is divided into the mobile tongue and the base of the tongue. The mobile tongue generally extends from the frenulum to the circumvallate papillae and is part of the oral cavity. The base of the tongue is posterior to the circumvallate papillae and is part of the oropharynx. In some examples, the first portion of the applicator can have a first concavity and the second portion can have a second concavity. The first and second concavities can be different, for example. In some embodiments, a bend, curvature, or concavity between the first portion and the second portion of the applicator results in the first portion of the applicator being generally or approximately orthogonal to the second portion of the applicator. In some embodiments, the curvature or concavity of the first and second portions of the applicator is designed and configured to match or conform to the anatomy of the patient, such that the curvature or concavity naturally allows the second portion of the applicator to reach down the base of the tongue into the vallecula.

FIGS. 11A-11C illustrates different embodiments of Applicators 1102 with applicator faces 1104 configured to treat the soft palate. FIG. 11A illustrates an embodiment of an Applicator 1102 that may be sized, shaped, and configured to treat the soft palate, while avoiding the uvula, endotracheal tube, and teeth. As can be seen in the drawing, the applicator 1102 may include a curved top portion shaped and configured to match the curvature of retropalatal region, but has a slight indent 1106 on a bottom portion towards the base of tongue to avoid the uvula. This indent may range from 5 mm to 15 mm in width to accommodate the size of the average width of the uvula.

FIG. 11B follows a similar to design to that of FIG. 11A to avoid the uvula while treating the soft palate. However, the applicator 1102 of FIG. 11B has a larger indentation towards the base of the tongue, giving the applicator a horseshoe-like shape, in order to completely avoid the uvula while treating posterior regions of the oral cavity with arms or extensions 1108.

The embodiment of FIG. 11C demonstrates an Applicator 1102 with a retainer 1104 to provide stability during treatment of the soft palate. The Applicator face is similar to that of the embodiment of FIG. 5B; however, a flexible retainer 1104 is attached to the top of the soft palate probe, with a hard spine 1106 to provide support to the retainer. The retainer can press against the hard palate in order to provide stability during treatment, with the retainer being 20 mm to 50 mm in length and 20 mm to 45 mm in width, to accommodate the size of the hard palate.

FIG. 12 shows a mechanical-based solution for articulation and placement of the soft palate probe, allowing an even force to be applied by the applicator face without moments. FIG. 12 illustrates an embodiment of an articulator that allows the face of the Applicator to articulate automatically at an angle of, for example, up to 30 degrees, or alternatively, up to 45 degrees, and match the angle of the soft palate utilizing pegs for the constant force springs 1201, a straight slot 1202, a custom clevis pin 1203, a pin 1204, a probe arm 1205, and a radial slot 1206. The device articulates by utilizing a constant force piston including constant force springs, a straight slot 1202, and a custom clevis pin 1203. Constant force springs are attached to the constant force spring pegs 1201 on top of the straight slot 1202 and attached to the custom clevis pin 1203 to control the force/pressure applied to the soft palate. A radial slot 1206 allows for the constant force pistons to rotate so that the force is normal to the soft palate. A pin 1204 is used to hold the mechanism in place until the physician has placed the probe, and removed to engage the mechanism, minimizing the reliance on the physician, and reducing probe placement variability. A pin 1204 and custom clevis pin 1203 allow the device to be attached to the probe arm 1205 to secure the device to a traction stand for procedure.

Other mechanical based solutions may be used for the articulation of the soft palate applicator, such as utilization of a balloon catheter or a steerable sheath. For example, a balloon catheter can be placed between the back of the Applicator face attached to a hinge and an immobile rod. By inflating the balloon catheter, a force is applied to the rod, which is repelled and directed towards the face of the Applicator in the direction of the oral cavity. This force then pushes on the Applicator, which is able to rotate on the X, Y or Z axis, depending on the placement of the hinge. Attaching the Applicator to a ball-joint with the addition of the balloon catheter may also allow articulation of the Applicator in the X-Y-Z axis. In addition to articulation, implementation of a balloon catheter would also allow an even force to be applied across the face of the Applicator. Another means of articulation would be attaching a steerable sheath to different areas of the Applicator, such as the back of the Applicator face to facilitate movement on the Z-X plane for positioning of the Applicator. Another example would be attaching a working channel containing an optical lens to a steerable sheath to obtain visualization in multiple directions. These methods may also be incorporated with Applicators intended for different treatment areas.

FIGS. 13A-13D illustrates multiple embodiments of Applicator probes 1302 that can treat multiple regions of the oral cavity. FIGS. 13A-13B illustrates a probe able to treat the base of tongue and the lingual tonsils. The applicator 1302 of FIGS. 13A-13B can include inlets 1304 and outlets 1306 for cooling fluid or medium, an insulated top surface 1308, non-insulated side or bottom surfaces 1310, and a shape 1312 that tapers toward the distal end to allow the applicator to reach into the vallecula. In shape, the Applicator tapers in width from proximal to distal end towards the vallecula, with a distal portion configured to treat the lingual tonsils. Insulation on top of the Applicator prevents injury to unwanted regions of the oral cavity, while non-insulated surfaces on the bottom and sides of the Applicator allow the Applicator to treat the intended target regions.

FIGS. 13C-13D illustrate an embodiment of an Applicator 1302 that can treat the soft palate, base of tongue, and lingual tonsils. FIG. 13B is similar to that of FIG. 13A, but has a spring-loaded arm 1314 mounted on the applicator 1302 with a separate soft palate probe 1316 configured to treat the soft palate. The soft palate probe is configured to articulate independently from the applicator 1302 via the spring-loaded arm. When the applicator 1302 is placed on the base of tongue, the soft palate probe 1316 is configured to be released to put pressure on the soft palate, allowing the soft palate to be treated along with the base of tongue without needing multiple applicators. The spring-loaded arm is configured to pre-bias the soft palate probe to apply force against the soft palate when deployed. As shown in the figures, the soft palate probe can include separate inlet/outlet tubes or lumens to supply a cooling fluid to the soft palate probe. The inlet/outlet tubes or lumens of the soft palate probe can be in fluid communication with the inlets/outlets of the applicator 1302, to allow cooling fluid that supplies the applicator 1302 to also supply the soft palate probe 1316.

In some embodiments, a chilled balloon or balloon-shaped Applicator may be used to concurrently treat one or more sites in the oropharynx (for example, the base of the tongue, the lateral pharyngeal wall, and/or the soft palate or uvula). The chilled balloon is selectively expandable between an expanded state and a deflated state and is configured to expand, in the expanded state, in the oropharynx to contact at least one of the pharyngeal walls and the palate (i.e., uvula).

FIGS. 14A-14B illustrate various additional embodiments of a needle Applicator designed to perform invasive cryolipolysis. In such embodiments, the needle Applicator may penetrate the tissue to deliver a cooling agent. In some examples, this cooling agent may consist of an ice slurry, composed of an ice content of preferably 20 to 40 percent, saline solution, and glycerol. In others, the needle Applicator may penetrate the tissue to administer vasoconstrictors and cryoprotectants to reduce blood flow and prevent unwanted ice formation. The needle Applicator may also penetrate and cool the tissue with surface contact. In some embodiments, hypertonic saline or Botox (e.g. $C_{6760}H_{10447}N_{1743}O_{2010}S_{32}$) can be delivered to augment the tissue modeling. FIGS. 14A-14D demonstrate an Applicator needle designed and configured for reduction of fat at the palate. Referring to FIG. 14A, a needle Applicator can be injected through the subcutaneous layer, under the chin and into the tongue, to penetrate the targeted tissue and administer a cooling agent. Referring to FIG. 14B, a needle Applicator can be placed intraorally, injecting a cooling agent into the dorsal surface of the tongue. The needle may also be placed midline or laterally through the lingual frenulum. Invasive means may also be applied to different areas of the oral cavity, such as the uvula, soft palate, lateral walls, and/or vallecula. For injection into the lateral walls, a needle Applicator penetrates through the lateral walls to inject a cooling agent with needles designed to prevent deep penetration, preferably only penetrating approximately 2 mm into the lateral walls to avoid contact with the carotid arteries. In some establishments, these protruding needles may also be curved.

FIG. 15 illustrates an embodiment of invasive cryolysis targeting the soft palate. In such embodiment the needle Applicator may enter intraorally through the mouth to penetrate the soft palate and inject a cooling agent, similar to what is described in FIG. 14A-14B, but this time into the soft palate.

In such embodiments, the needle Applicator is not limited to the number of penetrable attachments. The needle Applicator may be detachable or attachable to the non-invasive Applicator. Each penetrable attachment could be a different length, shape, or circumference. For example, the penetrable needle could be straight or curved. The needle Applicator may contain sensors at or near the needle tip in order to measure temperature, flow rate, depth of the needle, or pressure. Multiple attachments could also be applied to the needle Applicator to improve the efficacy of the penetration. For example, in one embodiment a needle Applicator could incorporate a suction system using a porous foam or plastic material that is not highly thermally conductive to pull the Applicator to the tissue firmly. Once properly placed, the needle Applicator may then inject small short needles into the tissue to administer a cooling agent to the targeted area. In another embodiment, a micro pump and syringe pump could be used in order to carefully monitor the amount and infusion rate of the cooling agent. In addition to, temperature sensors—which are typically thermistors—may record measurements at or near the needle tip and induce changes on the flow rate depending on the readings. In one example, if the temperature senor measured that the injection of the cooling agent was too warm, the flow rate could then be increased to maintain −5° C. In another embodiment, the needle Applicator could consist of a vacuum insulated needle in order to protect the tissue that the needle passes through and to keep the liquid as cold as possible until it reaches a targeted tissue.

FIGS. 16A-16B illustrates a concentric tubular probe implementation of an applicator 1602. This design can be used for the cooling of tissues by either contacting the tissues from the surface of the tissue (FIG. 16B) or by penetrating into the tissue to extract heat from deep tissue targets (FIG. 16A). For both embodiments, the fresh coolant is fed into the probe via an inner lumen 1604 and extracted using an outer lumen 1606. In some embodiments, the inner lumen can be concentric with the outer lumen. In one embodiment, the outer lumen can comprise the annular space between the inner lumen and an outer wall of the concentric tubular probe. FIG. 16A illustrates a penetrating version of the probe, which can be used for cooling large deposits of fat in the deep portions of the base of tongue. FIG. 16B illustrates a non-penetrating version of the probe which can be used for cooling the adenoids. Optionally, insulation can be placed over the outer tube to prevent cooling of non-specific tissues and concentration of the chilling effect at the distal end of the cooling probe.

FIGS. 17A-17B illustrates a double barrel probe design of an applicator 1702. As in the case of the concentric tubular probe described above, this design also can be used for the cooling of tissues by either contacting them from the surface of the tissue or by penetrating the tissue to extract heat from deep tissue targets. For both cases, the fresh coolant is fed into the probe via an inlet lumen 1704 while the return is provided by an outlet lumen 1706. FIG. 17A illustrates the penetrating version of this probe, which can be used for cooling large deposits of fat in the deep portions of the base of tongue. FIG. 17B illustrates the non-penetrating version of this probe, which can be used for cooling the adenoids. Optionally, insulation can be placed over both tubes to prevent cooling of non-specific tissues and concentration of the chilling effect at the distal end of the cooling probe.

FIG. 18 is an embodiment showing one example of Applicator packaging. The Applicator can be surrounded by a thermal insulator covering all surfaces except for the bottom (e.g., tissue contacting) surface. A cryoprotectant combination, including a cryoprotectant agent and a sheet, can cover all surfaces of the Applicator including the bottom surface. The sheet can be, for example, soaked in cryoprotectant that is attached to the Applicator.

FIG. 19 is an embodiment of an Applicator 1902 with potential sensor placements illustrated. Referring to FIG. 19, these sensors may be placed on or within the applicator for non-invasive measurement of parameters related to treatment or operation of the applicator or device. These additional sensors may comprise of pressure, fluid flow, contact, electrical impedance, temperature sensors, etc. For example, the Applicator can include an inline fluid temperature sensor 1904, an Applicator surface temperature sensor 1906, and a tissue interface temperature sensor 1908. In other examples, pressure sensors may be utilized to monitor fluid pressure at different locations to detect leaks and system anomalies, or to monitor the force and pressure that the Applicator is putting on the tissue. In one embodiment, the Applicator can include a temperature sensor to monitor the tissue temperature by penetrating the tissue, under the Applicator. For example, a nitinol needle could be flat on the Applicator during placement, but when a temperature change occurs, the needle changes shape and penetrates the tissue to allow temperature measurements at a predetermined depth.

FIG. 20 shows an alternate embodiment of an Applicator 2002, which can be an applicator similar to applicator 1902 including sensors 2004, 2006, and 2008. The applicator 2002 can include applicator packaging similar to that shown in FIG. 18. When compared to the embodiment that is shown in FIG. 18, the embodiment that is shown in FIG. 20 differs from that of FIG. 18 that the cryoprotectant combination is placed around the metal part of the Applicator, instead of going around the insulator. Pairs of adhesive sheets 2010 can be used between the metal Applicator and the cryoprotectant combination, and in between the cryoprotectant combination and the insulation. The advantage of the embodiment that is shown in FIG. 20 is the ease of manufacturing and higher reliability of the finished product.

FIG. 21A-21B illustrate additional embodiments of an Applicator 2102 with insulation. FIG. 21A illustrates an embodiment of insulation 2104 in direct contact with the Applicator 2102. The thermal insulation can surround the Applicator and can be designed to prevent the cryoablation of tissues that are to be preserved (i.e., non-target tissues). The insulation can be designed and configured to keep tissues that are in contact at or above +10 deg C even when the Applicator is at cold temperatures, such as −30 deg C. The thermal insulator may cover the sides as well as the top surface of the Applicator, but must not physically damage the tissues that come in contact with the insulation. In some examples, the insulation is solid or a structure with void spaces. The insulator may be plastic, or may be open or closed cell foam. In this embodiment, FIG. 21A shows a base of tongue Applicator surrounded by insulation, but any other applicator described herein may incorporate or utilize the insulation described with this embodiment.

FIG. 21B depicts a system configured to administer an applicator and insulator to the soft palate region, combining the two devices into one unit or system. The system of FIG. 21B works by way of capturing the soft palate between the soft palate probe and the insulator holder 2101. Insulation may be placed on the insulator holder 2101 by way of wrapping the insulation around the holder 2101 or by cutting a slit into the insulation to allow fitting onto the holder 2101. When cryotherapy is applied by the soft palate applicator to the soft palate, the insulator holder 2101 and insulation disposed thereon can be configured to be placed on the opposite side of the soft palate so as to protect other sensitive tissues beyond the soft palate from the cryotherapy.

FIG. 21B shows an adjustment mechanism 2110 that controls the relative positions and orientations of the applicator relative to the insulator holder and insulation. The adjustment mechanism 2110 can include a first shaft 2112 coupled to the applicator and a second shaft 2114 coupled to the insulator holder/insulator. The soft palate is easily captured between the soft palate probe 2102 and insulator holder 2101 by buttons 2103 and 2104 that allow the upwards, downwards, and or axial translation of the first and second shafts, the insulator holder 2101, and the soft palate probe. In addition to, the device also has a lever 2105 for deflecting the insulator in order to wedge the soft palate between the soft palate probe 2012 and insulator holder 2101. Once captured, the soft palate can be brought to the face of the probe by the upwards transition of the insulator holder 2101, or downwards translation of the soft palate probe. In some embodiments, the soft palate probe can incorporate a hinge or spring-loaded connection as described above to allow for translation or rotation of the soft palate probe relative to the tissue to be targeted. The device of FIG. 21B is also easily attachable to traction stands, incorporating a sliding spring clamp 2106 for attachment and ease of linear positioning. Contact and/or pressure sensors may also be utilized in conjunction with this device in order to apply the proper pressure to the soft palate, and ensure that contact is being made with the intended treatment region.

In other embodiments, the device of FIG. 21B may incorporate other ways for capturing the soft palate for insulation purposes. For example, the insulator holder 2101 of FIG. 21B may be replaced with an insulator attached to a hinge to hook around the soft palate once inserted into the oral cavity. This allows the insulator to always be aligned with the soft palate applicator, and could also incorporate a mechanism to pinch the soft palate with a known or predetermined pressure. Similarly, magnetic properties could allow the Applicator and insulator to be magnetically connected or drawn towards another once inside the oral cavity. In this embodiment, the insulator can be placed on the posterior side of the soft palate, and once the soft palate probe can be placed on the anterior side of the soft palate, the magnets on each component are then configured to lock or attract towards another to capture the soft palate between the insulator holder and the soft palate applicator.

FIGS. 22A-22B illustrates one embodiment of an insulator 2201 that is disjointed or disconnected from the Applicator to provide insulation and protection to different areas of the oral cavity. The insulator 2201 of FIG. 22A can be placed between the soft palate and the posterior wall of the oral cavity in order to protect the posterior wall and monitor changes in select variables, such as the temperature and the pressure. The insulator may be open or closed cell foam in order to allow flexibility and reach areas typically inaccessible in the oral cavity. The insulator can be a variable range of thickness with an indentation along the midline to prevent pressure from being applied to the spine. Sensors may be located on one or both sides of the insulator with the incorporation of a flex circuit. For example, pressure sensors or contact sensors may be attached in order to ensure the insulator is making even contact with the soft palate. Additionally, sensors or in the insulator can be used to determine when the entirety of the soft palate has been cooled. In some examples, the sensors on the insulator can be configured to monitor for a target temperature, and when the target temperature at the insulator is achieved, therapy can be automatically or manually stopped.

FIG. 22B provides an implementation of the insulator of FIG. 22A, where the disjointed or disconnected insulator 2201 is placed between the soft palate and the posterior wall in order to prevent cryoablation of tissues and nerves that are to be preserved. As shown in FIG. 22B, the insulator 2201 can be sized and configured to extend all the way from the soft palate out of the mouth of the patient, and can be positioned underneath or adjacent to the soft palate applicator, as shown. Temperature sensors 2204 are located on the insulator and sensors 2206 are located on the contact surface of the soft palate probe to compare the temperature difference between the anterior and posterior sides of the soft palate. By monitoring the temperature on different sides of the soft palate, it can be confirmed that the soft palate is cooled thoroughly; that is, the temperature sensor on the insulator is reading a temperature that is converging to the temperature sensor reading on the soft palate probe. For example, if the soft palate probe temperature is at −25° C. at the anterior side of the soft palate, it is expected that the posterior side of the soft palate cools to −5° C. which in turn would indicate a transmural treatment of the soft palate tissue. In another embodiment, temperature sensors may be located on the bottom of the insulator to monitor the temperature of the posterior wall and ensure that the posterior wall does not reach a temperature that could possibly cause cryoablation of the tissue and nerves.

Cryoprotectant combinations (CPC) can include a cryoprotectant agent and fabric sheet. A cryoprotectant agent can be pure glycerin or glycerol, or propylene glycol or any other non-toxic cryoprotectant compound that reduces ice formation in tissue at low temperatures, such as ethanol mixed with distilled water. The fabric sheet can be a porous textile material, made out of natural or synthetic fibers with overall sheet thickness in the order of 0.1 to 1.0 mm, preferably 0.4 to 0.5 mm. The fabric sheet can be wrapped around the Applicator and fixed mechanically or manufactured in the form of a sleeve and placed around the Applicator followed by cinching of a pre-installed thread for securing it in place. In either case, the fabric sheet that is soaked in cryoprotectant agent is used as a carrier for the agent.

Cooling and the heating of the Applicator is provided by convection where the fluid that is chilled or heated elsewhere is pumped through the Applicator. Typically, the chiller is set at a temperature in the range of 1° C. to 10° C. colder than the desired metal temperature of the Applicator. For example, if the desired metal temperature is −30° C., then the Chiller may be set at −35° C. It is also possible to set the Chiller to a much colder temperature at the beginning of the study, e.g., −40° C., to accelerate the cooling process. Regardless, by monitoring the temperature difference between the inlet and outlet fluids and knowing the flow rate, one can determine the amount of heat being extracted by the Applicator:

$$\text{Heat extracted}=(\text{OutletTemp}-\text{InletTemp})\times(\text{SpecificHeatOfFluid})\times\text{FluidFlowRate}.$$

Alternatively, one can calculate the heat extracted by monitoring the temperature differential between the Tissue Temperature Sensor and the Applicator Temperature Sensor, S2 and S3 in FIG. 20 respectively. In that case: Heat extracted=(TempS3−TempS2)/(Thermal ResistanceOfCPC).

Monitoring of the temperatures during a clinical procedure provides additional utility for device function. For example, a reading where one Tissue Temperature Sensor on the face of the Applicator indicates a much colder temperature at a location compared to another Tissue Temperature Sensor might suggest that the Applicator may not be making a firm, contact with the tissue at the location of the first Tissue Temperature Sensor, thus not uniformly distributing the cooling agent on the desired regions.

Monitoring of the temperatures during a clinical procedure provides additional utility for therapeutic efficacy. For example, oscillations and notches that are seen in Applicator Surface Temperature Sensors or Tissue Temperature Sensors might indicate that the deeper tissues may not be freezing completely. This could be caused when the Applicator is not sufficiently cold to freeze the deep tissues and keep them frozen. Initially, the deeper tissues may freeze, but since solids conduct heat better than the liquids, warmth from even deeper tissues may reach to the frozen section causing it to thaw. Thermal resistance of the thawed tissue increases, allowing it to freeze again, and the cycle repeats and resulting in the observation of thermal oscillations, which reduces the effectiveness of the adipocyte cryolysis. This freeze-thaw cycle can be avoided by lowering the Applicator temperature to halt the oscillations to keep the deeper tissues in frozen state and reduce the number of phase changes. Hence, during a clinical procedure, one can monitor the Applicator Surface Temperature and/or the Tissue Surface Temperature, and upon the observation of an oscillation, intervene by reducing the chiller temperature and/or increasing the fluid flow rate to increase the rate of heat extraction.

Warming of the Applicator during treatment can occur in a number of ways. A first option is to produce a warming curve in which the warmth is applied fast at first and then slowed down, without going above 37° C. A second option is to apply warmth as fast as possible to 40° C. For situations of re-warming, a PID control system may be used to achieve a specific rate of change or used to produce a curved that fits to a pre-defined curve with various rates. For example, a first rate that is very fast followed by a second rate that is much slower. To further utilize the warming procedure, the energy required to warm the tongue and/or the slope rate of warming the tongue could be used to calculate how much the tongue was cooled, as an efficacy indictor to verify good treatment. In one example, this could be calculated by mathematically measuring the area under the curve to assess how much cooling agent was applied to the tissue.

Warming of the Applicator during an emergency or at the end of the clinical treatment must be done at a high rate also to minimize the unintentional damage to the tissues that are near the surface. Minimum heating rate is 0.25° C./sec, preferably 0.4° C./sec or higher. This can be done by flowing warm fluid in the Applicator. Heating for this can be a direct inline heater, a heating reservoir or an aluminum bead reservoir which has the additional advantage of eliminating the need to store water. Having a heater that stores a warm mass with large heat capacity is beneficial in case of loss of heating ability or partial power failure. Similarly, a direct inline chiller or a cold reservoir may also be maintained in the case of an emergency where the tissue cooling demand during the initial part of the treatment exceeds the capacity of the chiller.

There are additional clinical tools that can be used during the treatment procedure. One of them is the cryoprotectant brush that can be used for the application of the cryoprotectant agent to the all-oral structures, such as the vallecula, tongue, epiglottis and even the palate. The brush can have bristles, or could be shaped as round or oval structure resembling a large Q-tip or look like a back scrubber. In either case, a cryoprotectant brush can be dipped into the cryoprotectant agent, and rubbed against the oral structures before the procedure to coat them with the cryoprotectant agent.

Another device that can be used for the preapplication of the cryoprotectant agent is an oral spatula as illustrated in FIG. 23. The illustrated device can be fairly flat and used to reach to the back of the mouth to deliver cryoprotectant agent that is pushed in from a proximally mounted syringe. This device has the advantage of delivering known amounts of cryoprotectant agent to desired locations.

An alternative, and simpler device is shown in FIG. 24. This device resembles a fly swatter where a relatively rigid frame, constructed out of metal or plastic is used to hold in place a mesh containing the cryoprotectant agent. In this case, the mesh is first soaked in cryoprotectant agent, and then the entire device is positioned on the tongue for a predetermined amount of time before the procedure to apply the cryoprotectant to the tongue surface.

FIG. 25 illustrates an Applicator 2502 with the ability to dispense and suction a cryoprotectant agent (CPA). The Applicator 2502 of FIG. 25 is configured for cryoprotectant dispensing through ports 2504 via a cryoprotectant inlet tube 2506 and suctioning via ports 2508 and a cryoprotectant outlet tube 2510 that runs similarly to the inlet and outlet lines that allow the flow of the coolant. CPA may be dispensed through ports 2504 in the bottom of the Applicator that can vary in a diameter of 2 mm to 10 mm depending on the viscosity of the cryoprotectant agent. In regards to FIG. 25, the location of the CPA channels may not only be midline to the Applicator, but also on the perimeter of the Applicator to reach the entire area of the treatment region. CPA application occurring via Applicator allows possible automation of CPA dispensing, such as having the controller regulate the volume of cryoprotectant applied, or set cryoprotectant application for a certain time and/or fluid flow rate, allowing the optimal amounts of cryoprotectant to be applied to reduce waste, ensure proper application, and reduce operating time.

Suctioning of the CPA may occur concurrently or subsequent to dispensing. For example, CPA application may occur for the duration of the treatment, however after 60 seconds of dispensing, suctioning may commence to ensure that CPA pooling in the vallecula does not arise. FIG. 25 depicts suctioning ports 2508 on the top anterior side of the Applicator to more easily access areas where CPA pooling may occur, such as the vallecula; and may further include a suction outlet having a coupling to couple to a hose, and a suction channel connecting the suction inlet and suction outlet. In different embodiments, the Applicator further includes a suction inlet located on the contact surface, which may be towards the distal or anterior end of the body. Suctioning at the contact surface would allow the removal of the CPA as well as tightly adhering the Applicator to the tongue; thus, one or more suction inlets may be present to ensure proper contact with the entire area of the Applicator. In addition, contact sensors may be disposed on the contact surface of the Applicator to allow for automation of suctioning for optimal application. For example, if the Applicator is not securely on the treatment region, the contact sensors could relay information to the controller, which would subsequently decrease pressure of the inlet and adhere the Applicator more tightly to the treatment region.

In some embodiments, the heat exchanger further includes a suction inlet located on the contact surface; a suction outlet having a coupling to couple to a hose; and a suction channel connecting the suction inlet and the suction outlet. In some embodiments, the suction outlet is located (i) at the distal end of the body and (ii) proximal to the cooling inlet and cooling outlet.

Cryoprotectant agents of lower viscosity represent a special difficulty during their application to the target tissues and while trying to monitor the resulting concentration of the agent following the application. Cryoprotectant agents that are constructed in gel form allow the volume of CPA applied to remain constant while also making their application easier for the physician. FIGS. 26A-26B illustrate a cryoprotectant agent in the form of glycerol-gel contained in a silicon pouch that adheres to different surfaces. FIG. 26A depicts a cryoprotectant agent that is in a gel form and adheres to the bottom of the Applicator prior to the insertion of the device in the patient's mouth. In this embodiment, the cryoprotectant can adhere to the cryoprobe before application in order to ensure that the treatment area has cryoprotectant on all regions of the contact surface of the Applicator. FIG. 26B depicts the same CPA in glycerol-gel form, however the glycerol-gel is first placed on the treatment area, with the Applicator then placed on top of the glycerol-gel. The casing containing the glycerol-gel may include a mucoadhesive polymer such as carboxymethylcellulose in order to adhere to the surface of the treatment area, such as the base of tongue. To place the CPA pouch, a spatula-like device may be used to cup the packet and slide or flip the pouch onto the treatment region. In these embodiments, the glycerol-gel comes pre-made and sealed in a pouch, requiring the physician to only open the package and place the cryoprotectant on the probe or treatment region to apply the cryoprotectant agent, reducing operation time. Additionally, the packaging of the cryoprotectant can be biodegradable. For example, the silicon casing may be made out of alginate and gelatin, and be cross-linked in various combinations for different degradation rates to ensure that the cryoprotectant casing does not dissolve before the operation is complete. Furthermore, the gel may be delivered in sterile or non-sterile form.

The Applicator should be placed in the correct position in the mouth of the patient for the optimal treatment efficacy, which is generally the most superior and posterior section of the tongue. Since that region falls in the back of the tongue, it tends to be difficult to verify that the Applicator has been placed appropriately. In some embodiments, the systems and methods can include fluoroscopy-based, visual, and mechanical methods to address this problem, which will be described next.

FIG. 27 shows a fluoroscopy-based solution for the placement of an Applicator in the mouth. In this embodiment, a radio opaque ring 2701 is placed over a trachea tube and the ring is pushed to position near the epiglottis. Later on, the Applicator is placed in the mouth, under fluoroscopy guidance, and guided to the radio opaque ring to allow for accurate and precise positioning of the applicator relative to the target tissues.

FIG. 28 shows another fluoroscopy-based solution for the placement of the Applicator in the mouth. In this embodiment, a radio opaque frame 2801, such a steel wire, is pre-bent and placed over the tongue by pushing it all the way to the back, assuring that the distal end of the wire frame is in the vallecula. Next, the Applicator can be placed in the mouth, under fluoroscopy guidance, and guided to the radio opaque ring to allow for accurate and precise positioning of the applicator relative to the target tissues.

FIG. 29 shows another solution to visualization problems to facilitate proper placement of an applicator. In this embodiment, an endoscope is advanced, either through the nasal passageway, or within the oral cavity. FIG. 29 shows the path of the endoscope for a nasal passage. The Applicator is placed in position using visual guidance from the endoscope. FIG. 29 also shows an optional enhancement where a fiber optic wand that is used for the illumination of the outer frame of the Applicator. Self-illumination of the Applicator would allow it to be easily recognized even when it is submerged under a pool of saliva and/or cryoprotectant fluid.

FIG. 30 shows an ultrasound-based solution to visualization problems while also monitoring the thickness of ice formed during treatment. In this embodiment, an ultrasound transducer is placed underneath the chin, just before the crevice of the neck, allowing visualization of the base of tongue on a screen to properly place the Applicator on the treatment region. In addition, the use of an ultrasound transducer allows the monitoring of ice thickness formation on the base of tongue by measuring the distance from the ultrasound probe to the Applicator, and, once ice is formed, measuring the distance from the ultrasound probe to the ice formation. Thus, once these two distances are measured the ice thickness can be computed by calculating:

$$\text{Ice Thickness} = (\text{Distance from Ultrasound Probe to Applicator}) - (\text{Distance from Ultrasound Probe to Ice Formation})$$

Measuring the amount of ice formed would allow physicians or the controller to determine if ice is accumulating during treatment, and whether or not the temperature of the coolant needs to be changed. In another embodiment, ultrasound transducers may be placed on the Applicator's contact surface, further discussion of this method is below in relation to FIG. 43L and FIG. 43M.

FIG. 31A shows an embodiment of an Applicator 3102 with two working channels 3104, with one working channel containing an optics camera in line with the Applicator to assist with visualization before, after, or during operation and the other channel containing a flexible suction tube for the removal of excess of saliva, blood and cryoprotectant from the oral cavity. Visualization through the optical camera can be accomplished by mounting a small camera on the Applicator in one or multiple locations to allow the user to actively monitor the placement of the probe, and confirm proper placement of the probe for operation. To assist in visualization, a working channel may be used to enclose the optical camera, such as an endoscope. The working channel, or tube, can be made of any material. However, clear tubing is more effective as it helps the user orient the location. The tube length can be made so that the endoscope can utilize its bending mechanism to visualize the end of the probe and its placement in relation to the epiglottis, soft palate, and vallecula. For example, for proper visualization during the base of tongue treatment, the working channels would preferably be a length that is longer than the soft palate and shorter than the epiglottis, while still being able to be placed down into the vallecula space. A secondary function of this working channel is to deliver suction to critical areas for sterility and visualization. The ID of the tube is such that it can fit a flexible suction tube, as well as a scope. While the embodiment of FIG. 31A shows two working channels, any number of working channels may be added to the Applicator.

FIG. 31B illustrates potential locations 3106 for the optical camera to be mounted. The channel may be mounted along the arm, or on the Applicator insulation. If it is on the Applicator insulation it will be mounted on the left or right side, and follow the inlet or outlet tubing accordingly. A light source can be mounted in a similar fashion to provide illumination. Working channels may be configured as an attachment to the handle or to the Applicator itself Furthermore, it can be suspended from the handle. There may be one working channel on either side, i.e., right or left, or two channels may be provided to allow better visualization that may be necessitated due to placement of the endotracheal tube.

Temperature measurement made on the Applicator can be transferred to the Console for processing by a computer or electronic controller and for informing the medical professionals. As it's shown in FIG. 1C, these analog signals could be carried out from the Applicator to the Console in analog form and then converted into digital. FIG. 32 shows another embodiment of an applicator 3202 where the analog signals representing the temperature measurements from temperature sensors 3204 are converted into a series of digital signals on board the Applicator before being transmitted to the Console. In that case, the on-board electronics can contain amplifiers and signal conditioners 3206, an analog multiplexer 3208, an analog to digital converter (ADC) 3210, and a serial driver 3212 for the transmission of the data. The ADC may have a resolution in the range of 8 bits to 16 bits, and the serial driver may also perform the duties of the brand protection, such as sending the serial number. The board electronics can be connected to the Console via few wires, such as power, reference or ground and the serial data, or by wireless connection (e.g., wifi, Bluetooth, or some other wireless communication protocol). To reduce power consumption and the risk to the patient, it is preferable to operate at low voltages, such less than 5 Volts. The digital data transfer scheme has the advantage of increased reliability due to few leads and improved RF immunity. On board electronics unit could be constructed using radiation hardened electronics or housed in a metal structure or a cavity within the Applicator to allow the finished device to be sterilized using e-beam or gamma ray techniques.

Referring to FIGS. 33A-33B, the Applicator can be attached to a fixture arm via joint that might have 1, 2, 3, or more degree of freedom, i.e., pitch, roll and yaw. This gimbal type attachment allows the force that is applied by the Arm to be distributed more uniformly over the target tissue surface. The fixture arm might have many different shapes and curvatures, which is determined based on the rest of the fixation system, also known as the traction system, which is described in detail below.

FIGS. 34A-34B illustrate a close-view of the arm 3410 of the sleep apnea system, which can include an attachment point 3402 for the constant force system described above and to the Applicator. The arm can have a profile/radius that corresponds with the radius of the human hard palate. Referring to FIG. 34B, the arm can include a cross-section that provides guide features that provide stability and eliminate unintended rotation.

Figure 35A:
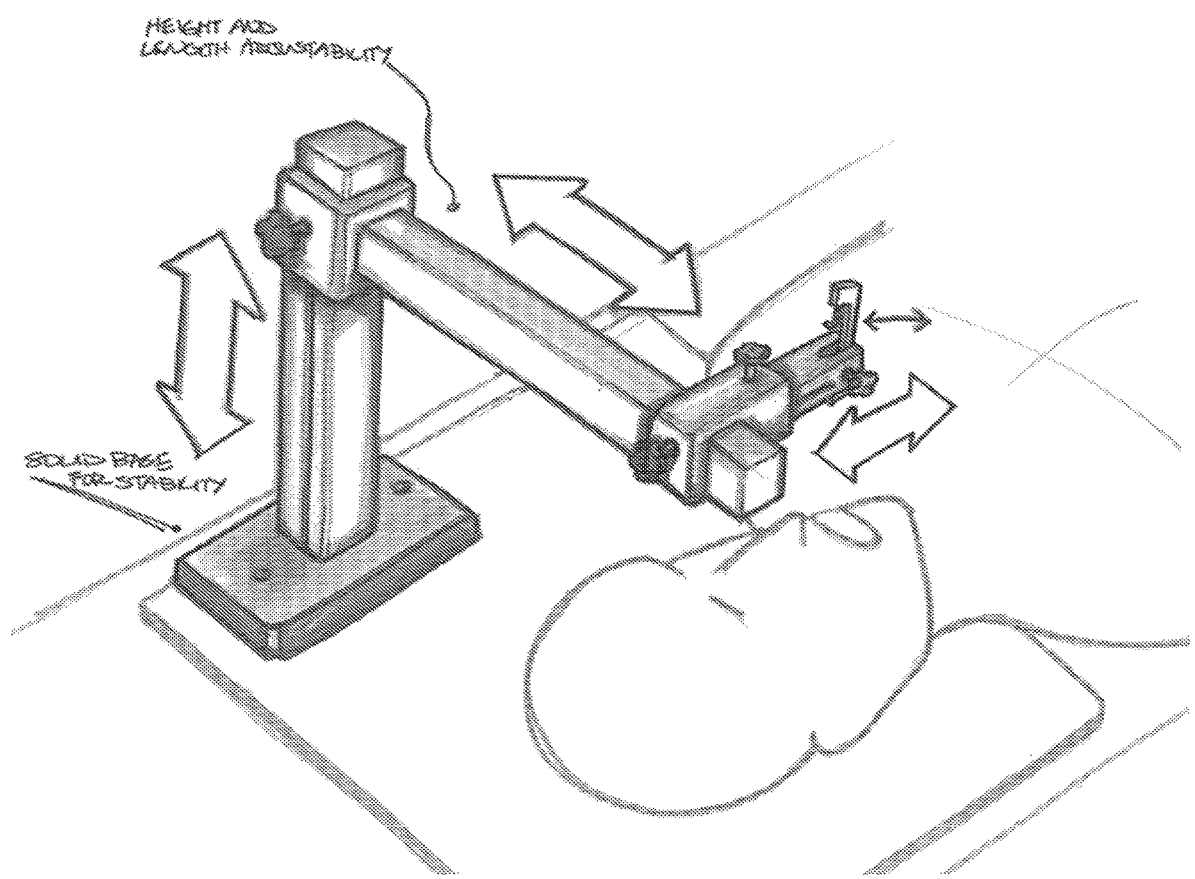
Figure 35B:
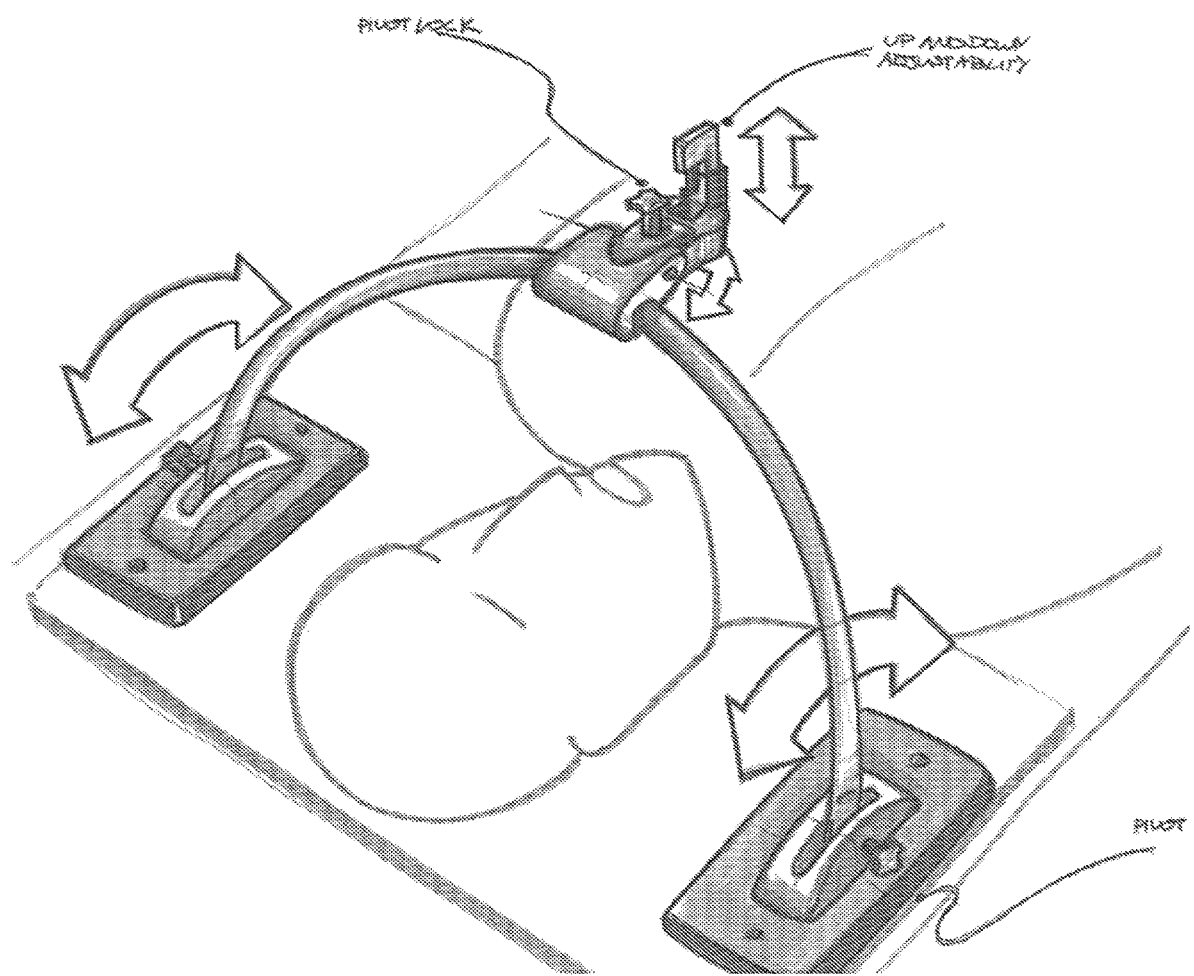
Figure 35C:
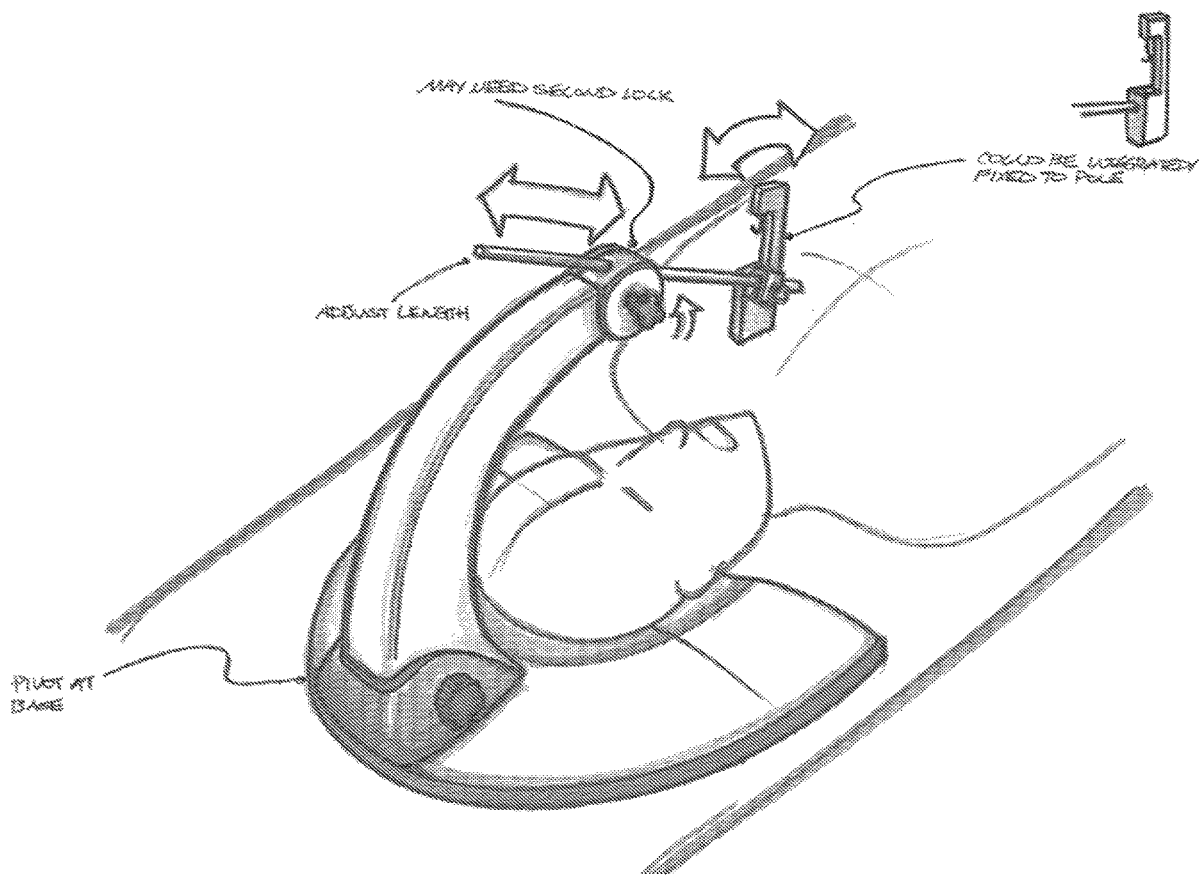
Figure 35D:
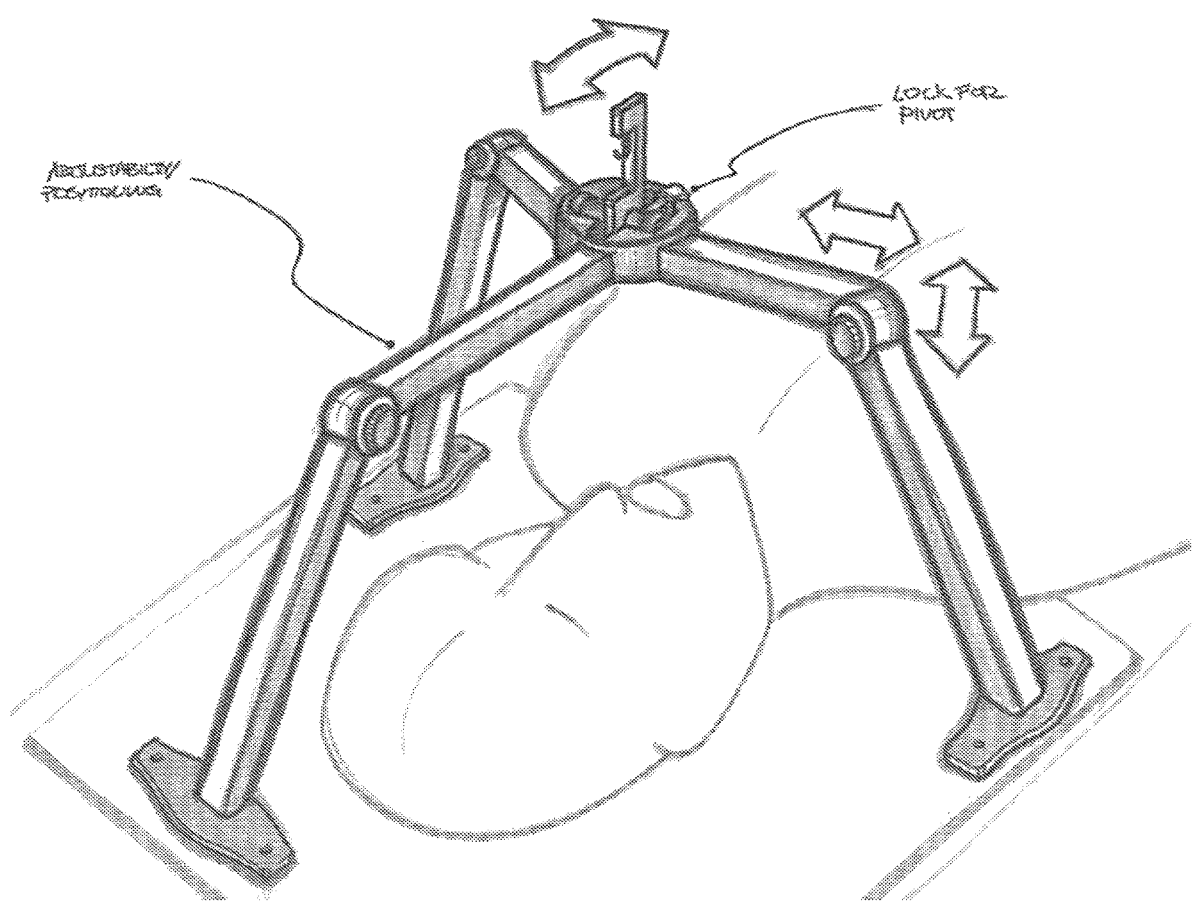

FIGS. 35A-35D illustrate additional embodiments of the force traction systems. The embodiment of FIG. 35A allows for adjustability along the XZY axis. This embodiment can be side mounted to allow easier patient placement under the system. In one example, the pivot point could be smaller or closer to the size of the device to minimize bulkiness. The embodiment of FIG. 35B provides an arc-shaped support in which the entire fixture pivots at the base for ease of positioning around the patient. The pivot can not only adjust the height of the arm with respect to the patient, but also the angle of the arm to the patient. The embodiment of FIG. 35C includes a plate that holds the patient's head and provides stabilization for the fixture. The system can pivot at the plate to allow for length and angle adjustability. The length and pivot may include separate locks. FIG. 35D illustrates another embodiment of the force traction system which can include a tripod design which provides for exact positioning around the patient. Each leg of the tripod can be pivoted and locked in place during positioning.

FIG. 36A-36B illustrates one example of a mechanical design of a mountable force traction system 3600. FIG. 36A provides detail of the overall system of the mountable stand, where the stand may be mounted to a bed or a bed frame. To mount the device of FIG. 36A, a Clark socket 3601 can be attached to an external support to provide stability and vertical adjustment of the stand. The Clark socket 3601 is attached to a similar device described in FIG. 36B to allow vertical and rotational movement of the connected traction arm 3602, tube holder pivot 3603, and telescoping tube holder 3604. The rotational maneuverability of the traction arm 3602 and telescoping tubes 3604 facilitates movement in the XY plane by way of a double barrel bearing 3605, allowing the traction arm 3602 and telescoping tube holder 3604 to be placed in an optimal interface placement and out-of-the-way positioning during procedures. The double barrel bearing 3605 is connected to the tube holder pivot 3603, allowing additional rotation around the tube holder pivot 3603 and varying degrees of freedom from the component of FIG. 36B. The implementation of the telescoping tube holder 3604 may be used to hold the inlet and outlet telescoping tubes of the application device. This implementation allows constant force and pressure of the Applicator as varying positions of the tubing may cause the Applicator to put too much or too little pressure on the treated area while operating. Additionally, different positions of the tubing may elicit different flow rates of the coolant throughout the procedure. FIG. 36B includes an additional device of the mountable force traction system that facilitates rail and tube rotation of the telescoping tube holder 3604 around the tube holder pivot 3603. The clamp 3606 of the double barrel bearing 3605 is connected to the traction arm 3602 of the mountable force traction system 3600 to allow rail rotation. Rail rotation facilitates movement along the y-axis to allow proper alignment of the Applicator to the patient's mouth. The pin 3607 is connected to the tube holder pivot 3603, allowing the telescoping tubes to rotate on the XY-plane. The bearing brake 3608 can be used to secure the double barrel bearing 3605 in place for procedure. The use of the double barrel bearing 3605 also allows the mountable traction stand to securely clasp and position the telescoping tube holders 3604 so that the tubes connected to the Applicator will be secured and positioned properly during the procedure.

FIGS. 37A-37C illustrate multiple embodiments of bed-mounted traction stands and their components. FIG. 37A illustrates a bed-mounted armature that only requires one connection point to the bed in order to optimize the amount of space the physician has to work in. The device has an attachment point 3701 that allows the applicator 3702 to be inserted into the traction stand, acting as a ball joint for rotation along the XYZ planes. Once inserted, the applicator can move along the XY-plane for accurate placement in the oral cavity via the handle 3703. The handle 3703 has a locking lever 3704 to allow the physician to hold down while positioning the device, and release once in place to lock the position of the applicator. Additionally, this handle 3703 is ergonomically placed for the physician to be standing at the head of the bed for adduction and abduction of the applicator. The attachment limb 3705 allows rotation of the device via a pivot joint so that the device may be moved out of the way 3706 while the patient is laid down onto the operation table. This device may be able to be secured to the table by way of clamp 3707 that can be connected to the table.

The pointers 3708 illustrate the detection paths of position sensors that may be placed on different embodiments of traction stands. These sensors would alert physicians if the patient were moving during operation, possibly changing the position of the applicator in the oral cavity. In one example, the position sensor path could be directed at the midline of the patient's head, whereas the other path would be directed just outside the side of the patient's head.

FIG. 37B illustrates a bed-mounted traction stand that cradles the patient's head for procedure while simultaneously aiding in the operation. The bed-mounted traction stand of FIG. 37B is able to be placed on the operating table, where the material on the bottom may be rubber to increase friction and prevent the device from moving. Once secured on the operating table, the patients head can be placed in the height adjustable headrest 3709. The adjustability of the headrest 3709 allows for the patient's neck to be craned in a way that opens up the oral cavity more, making placement of the applicator easier. In addition, the foam component layer 3710 near the patient's shoulder and neck area also allows more articulation of the neck while comfortably lifting the shoulders. Once the patient is placed, the frame 3711, which may be made of metal bent tubing, is slid over the patient, allowing movement about the Y-axis, and locked passively into place by way of cantilevered rods 3712. This sliding feature allows the frame to be moved out of the way for the patient to be placed in the device. In addition, the frame 3711 can have a probe articulation mount 3713, which would allow the probe to be placed onto the mount and rotate about the x-axis. In addition, the attached probe may also move along the x-axis direction. The articulation mount 3713 would limit the probes movement during operation so that different pressures are not being placed on the target region, and allow the probe to be locked at an optimal angle and position for placement into the oral cavity by including locks on the articulation mount's joints 3714.

FIG. 37C illustrates a device that can be attached to the articulation mount 3713 of FIG. 37B by an attachable clamp 3715 while holding the probe. The clamp 3715 can be locked onto the articulation mount 3713 by way of clamping the rod 3713, creating something similar to a hinge joint. The handle 3716 allows the physician to slide the applicator backwards or forwards in the patient's oral cavity. The movement along the Y-axis is helpful in ensuring contact with the target tissue. A thumb trigger 3717 is included to lock the applicator in place once proper pressure/contact is made with the target area.

The features of FIG. 37B-37C allow ideal physician ergonomics, with the physician placing the applicator into the patients mouth at the head of the bed by way of adduction and removing the applicator from the patients mouth by abduction.

FIG. 38A-38C illustrates the mechanical design of the force traction system 3800. FIG. 38A provides detail of the overall stability of the stand, in which a traction stand 3802 can be connected to a baseplate 3804, or attached to a surgical table or other structure, such as a Mayo stand or tray, depending on the height and stability of the stand. The Mayo tray may be positioned over the patient in order to allow proper positioning and stability of the alignment gauge. FIG. 38B provides additional mechanical details of the force traction system. A crossbar 3806 can be used to connect the traction rail 3814 to the alignment gauge 3818 of the sleep apnea device. The crossbar may be held in place along the Z-axis by a crossbar upright lock 3808, allowing motility to provide adjustment in height based on the patient's chest depth while also facilitating 360-degree rotation. This rotational maneuverability facilitates placement of the traction frame 3804 but allows the frame to be out of the operating field during placement. A crossbar collar 3810 may also be placed along the traction stand 3802 to restrict movement of the crossbar 3806 along the Z-axis. This placement ensures the crossbar 3806 will not injure the patient if the crossbar upright lock were to malfunction. The crossbar 3806 may also have a crossbar extension clamp 3812 to allow extension and retraction of the crossbar 3806 to aid in proper placement of the sleep apnea device. A traction rail 3814 can be connected to the crossbar 3806 by way of a traction rail locking knob 3816. This traction rail 3814 can be used as a guiding agent for the alignment gauge 3818 of the sleep apnea device, where the traction rail locking knob 3816 stabilizes and locks the traction rail 3814 into place. This traction rail 3814 allows for angular and positional alignment along the frame with the arm guide. A probe cover 3820 may be placed on the alignment gauge to prevent cross contamination during the exam. The alignment gauge of FIG. 38C may attach and detach to the traction rail 3814. The alignment rail 3818 is a fixed length piece which may be used to determine the location of the patient's mouth with respect to the traction stand for ensuring proper placement of the cryoprobe when the procedure in underway. The probe at the end of the alignment rail 3818 is covered with a sterile pouch 3820 so that it may be placed over the sterile field of work.

FIGS. 39A-39B illustrate different embodiments of a cart-mounted traction stand. FIG. 39A illustrates a cart system with a tube set connection 3901 and an attached traction stand 3902. The tube set connection 3901 can hold the applicator tubes that deliver coolant to the applicator, while also allowing the tubes to retract inside the cart, so that an unnecessary length of tubing was exposed during the procedure. The cart can have an attachable region for the traction stand so that the applicator can be mounted. The traction stand 3902 can be extended from the cart via boom adjustment handles 3903 in order to have the cart components out of the way when an operation is not being performed. In addition, the traction stand can be moved up and down via an additional boom adjustment handle 3904 for aiding the physician in placing the applicator. Other features of the cart system include a swivel LED interface 3905, that may aid in visualizing the inside of the oral cavity for positioning of the applicator in the mouth, such as a console based endoscope. The cart can be moved by a maneuvering handle 3906 and locked into place via locking canisters 3907 on the wheels. The cart may also have additional rods 3908 for storage and hanging of devices.

The cart system of FIG. 39B is similar to the traction stand of FIG. 37A, but with a cart attachment rather than a bed attachment. Similarly, the device has an attachment point 3909 that allows the applicator 3910 to be inserted into the traction stand, acting as a ball joint for rotation along the XYZ planes. The traction stand has an additional notch 3911 for holding the telescoping tubes, so they do not get in the way during procedure or cause any unwanted pressures. The armature 3912 of the traction stand can be attached to the cart so that the arm is able to rotate out of the patients face once the procedure is over. Other features of the cart include cannister locking wheels and a swivel LED screen that aids in visualization during the procedure.

FIG. 40A-40B illustrates customized head and shoulder padding to properly position the patient during the procedure. FIG. 40A depicts head padding in a donut shape to allow the patients head to comfortably rest with their head lowered and jaw lifted to aid the physician in placing the Applicator. FIG. 40B depicts similar head padding with the addition of shoulder padding in order to lift the shoulders to angle the neck of the patient more comfortably, and more easily access the oropharynx region. The padding material can be open cell polyurethane, or any material that is comfortable for the patient yet dense enough to keep the patient in the same position. The size of the padding can come in variable sizes for different sized patients. The padding may also include built in contact and/or pressure sensors to monitor the patient's movement during the procedure.

FIG. 41 is a close-up view of a constant force system 4102, which can include an arm guide 4104 configured to receive the arm of the sleep apnea treatment system. The arm guide can include a threaded hole and locking knob configured to lock the arm into place. The constant force system can further include a hook 4106 that attaches to the arm and a constant force spring 4108 which is configured to pull on the hook and arm.

Guidance systems can provide additional aid with proper placement of the Applicator and treatment for the patient. These guidance systems may consist of MRI imaging, ultrasound imaging, and electrical impedance tomography (EIT). In one example, MRI imaging or ultrasound imaging of the patient before treatment can provide patient anatomy, utilized as a guide for Applicator placement. Motor actuators may also be included based off of this imaging for aid with position the Applicator. Further utilization of these devices will be discussed in more detail below.

FIG. 42 illustrates a control algorithm flowchart, according to one embodiment. When the algorithm begins, the treatment system can initialize the cooling temperature, the cooling duration, and the heating duration of the Applicator. The system can then apply the cooling to the tissue for the cooling duration at the cooling temperature. During the application of cooling, temperature sensors disposed at the surface of the Applicator can measure the temperature and be used by a controller to determine if the surface or tissue temperature is oscillating or changing. If not, then the cooling temperature is not changed. If, however, the surface or tissue temperature is changing, the cooling temp can be appropriately adjusted. After the application of cooling for the cooling duration, the Applicator can be warmed at the warmed temperature for the heating duration. Then the treatment process is ended.

Multiple sensory feedback systems and control algorithms can be combined to further enhance the safety and efficacy of treatments. FIGS. 43A-43M illustrate multiple embodiments of a control algorithm flowchart during the initialization, cooling, and warming processes, in which the controller can perform different feedback algorithm operations, or none at all. The embodiment of FIG. 43A utilizes no sensors, hence the operation is completely open loop and temperature is controlled by the algorithm of FIG. 43B. Due to no sensors being present, the algorithm provides no sensory feedback from the tissue and runs solely on procedure time. The treatment is initialized by a predetermined and fixed cooling duration, denoted Cool_Duration, in which the system cools the Applicator face for a predetermined and fixed amount of time, reaching a desired cooling temperature. After the cooling process is complete, the system similarly warms the Applicator face for a predetermined and fixed amount of time (denoted as Heat_Duration), reaching a desired warming temperature. Once reached, the treatment process is ended.

To illustrate an example of the embodiment of FIG. 43A and algorithm FIG. 43B working in unison, the temperature determinant, which is the chiller and heat combination, would be set to the desired temperature control as a fixed temperature. During the cooling phase of the treatment, the coolant fluid would be chilled by the chiller of the temperature determinant. The chilled fluid would then be pumped through insulated tubing before it reached the Applicator. During the travel through the tubing, the fluid warms up, usually by about 3° C., as it picks up heat from the surroundings. Additional rise of approximately 2° C. in the temperature may be observed when moving from the coolant that is within the Applicator to the bottom surface of the Applicator that is near the tissue, bringing the total positive increase in the temperature difference between the face of the Applicator and the Chiller of the temperature determinant to approximately 5° C. To bring the Applicator to a desired temperature, the temperature determinant can be set to a temperature that is 5° C. colder than the desired Applicator temperature. For example, if the desired Applicator temperature is −30° C., then the chiller of the temperature determinant will be set at −35° C. If the ambient temperature is +20° C., then the temperature differential between the coolant and the environment would be more than 65° C., explaining the heat gain by the coolant during its travel from the Chiller of the temperature determinant to the Applicator. During the heating phase, the warm fluid coming from the heater of the temperature determinant will start at +37° C. and would have less than a 20° C. temperature difference from the ambient, hence it would not lose much heat. Therefore, one may choose to set the heater of the temperature determinant to +37° C., or to a temperature that is slightly higher, such as +39° C. This method of open loop temperature control would have the advantage of not needing sensors or a sophisticated feedback controller.

The embodiment of FIG. 43C utilizes temperature sensors that are in contact with the tissue in order to provide feedback to the control algorithms of FIG. 43D, FIG. 43E and FIG. 43F. This particular implementation has only temperature sensors, hence the operation can be closed loop. During the cooling phase of treatment, temperature control is achieved by adjusting the temperature of the temperature determinant, the coolant flow rate, or both, to maintain the Applicator at the target temperature. As it was described earlier, during the cooling phase, the Applicator temperature is about 5° C. warmer than the temperature of the chiller of the temperature determinant. However, due to the large thermal mass of the chiller, the response time could be longer than desired. Hence, the finer corrections can be achieved with the changes in the coolant flow rate. For example, an increase in the coolant flow rate would enhance the delivery of chilled fluid to the Applicator, which in turn would increase the rate of heat extraction, and lower the temperature of the Applicator. Conversely, one can lower the coolant flow rate to allow the temperature of the Applicator to raise. Since the flow rate can be changed at will and rapidly, the modulation of the flow rate would allow a finer control of the Applicator compared to changing the temperature of the chiller of the temperature determinant. However, there will be practical limits on the coolant flow rate. For example, the coolant flow rate cannot be less than zero. There is also an upper limit on the coolant flow rate which is determined by the properties of the coolant pump and the resistance of the system to fluid flow. Hence, the optimal temperature control algorithm may employ both methods of temperature control, i.e., the temperature of the chiller of the temperature determinant and the rate of the coolant flow.

The algorithm of FIG. 43D provides one implementation of sensory feedback from temperature sensors disposed at the surface and/or inlet and outlet of the Applicator to control treatment duration, and may focus on the control of the tissue temperature rather than the Applicator face temperature. The treatment is initialized by a predetermined and fixed cooling duration, denoted Cool_Duration, in which the system cools the Applicator tissue for a predetermined and fixed amount of time, reaching a desired cooling temperature. After the cooling process is complete, the system similarly warms the Applicator tissue for a predetermined and fixed amount of time (denoted as Heat_Duration), reaching a desired warming temperature. Once reached, the treatment process is ended.

The algorithm of FIG. 43E provides another implementation of sensory feedback from temperature sensors disposed at the surface and/or inlet and outlet of the Applicator to control treatment duration, and may be implemented by the configuration of FIG. 43C. When the algorithm begins, the system can cool the Applicator to TEMP, which is a predetermined and fixed cooling duration. During the application of cooling, temperature sensors can measure the temperature and determine the heat duration from the cooling and heating time constants (τ_HEAT, τ_COOL). In one example, the heat duration can follow an equation of:

$$\text{Heat\_Duration} = 5 \text{ min.} + 20 * \max\left[f_0\right](\tau\_\text{HEAT}, \tau\_\text{COOL})$$

This equation is output by temperature sensory data collected during the cooling duration of the process. The Applicator TEMP is then warmed for the calculated heating duration and the treatment process is ended.

The algorithm of FIG. 43F provides another implementation of sensory feedback from temperature sensors disposed at the surface and/or inlet and outlet of the Applicator to control treatment duration, and may be implemented by the configuration of FIG. 43C. When the algorithm begins, the algorithm cycles through a list of checks, the first being a predetermined and fixed time limit for the cooling phase labeled Cooling_1_Duration. If the cooling phase is complete and the tissue is frozen, then the heating is started. If the cooling phase is not complete, that is, the tissue is not frozen, then the algorithm checks to see if the face temperature of the Applicator is above a maximum temperature. If the Applicator phase is above the maximum temperature, the algorithm attempts to lower the Applicator by decreasing the temperature of the chiller of the temperature determinant for a predetermined and fixed cooling duration, designated Cool_2_Duration. In some embodiments, the algorithm may increase the coolant flow rate to correct the temperature, as discussed above. If the face temperature of the Applicator is not above the maximum temperature, the algorithm checks to see if the face temperature of the Applicator is below the minimum allotted temperature. If that is the case, the algorithm attempts to increase the Applicator temperature increasing the temperature of the chiller of the temperature determinant, or, in some embodiments, decreasing the flow rate, as discussed above, before repeating the cycle. Once the tissue is frozen, the Applicator is cooled further for a predetermined and fixed amount of time, denoted as Cool_3_duration, to a target temperature of TCOLD2±ΔT. After this duration is finished, the Applicator is heated to a target temperature for a predetermined and fixed Heat_Duration. Once this heating duration has finished, the treatment process is ended. A temperature vs time scale of the algorithm of FIG. 43F can be seen in FIG. 43G, describing each cooling and heating duration in the algorithm. The sudden "positive jump" 4301 that is seen in the temperature trace indicates a phase change, alerting the algorithm that the tissue is now frozen, initiating the Cool_3_duration. The jump in the temperature trace is believed to be due to the release of latent heat of freezing from tissue and/or the Applicator-tissue interface.

The embodiment of FIG. 43H utilizes force transducers in order to monitor the changes in tissue compliance to assure that the tissue underneath the Applicator is frozen during the treatment procedure based on the algorithm of FIG. 43I. The algorithm of FIG. 43I provides sensory feedback from pressure transducers located on the face of the Applicator to determine a proper cooling temperature. The Applicator TEMP is reduced to a target temperature for a predetermined first cooling duration, where after the force and pressure transducers determine tissue compliance from the given displacement and pressure measurements recorded to determine if ice formation occurred. If the tissue is not frozen after this stage, the cooling target temperature is further decreased and cooled until a frozen state is reached, repeating the same cycle. Once the tissue reaches a frozen stage, the Applicator TEMP is reduced to the determined cooling temperature for a predetermined and fixed second cooling duration, in which this second cooling duration may be a different amount of time from the first. After this duration, the Applicator TEMP is raised to the target temperature for the remaining heating duration and the process is ended.

The embodiment of FIG. 43J utilizes low level AC currents that are applied to the tongue to detect changes in the electrical impedance of the tissue to assure that the treatment volume in frozen during the clinical procedure based on the algorithm of FIG. 43K. The algorithm of FIG. 43K provides sensory feedback from electrical impedance to determine the frozen tissue size and/or the composition of the tissue underneath the Applicator. The Applicator TEMP is reduced to a cold target temperature for a predetermined first cooling duration, after which the complex electrical impedance of the tissue is determined by use of electrical impedance sensors, registering the size of frozen sections of the tissue as electrical impedance, giving:

$$Z_{FROZEN} = Z_{PRESENT} - Z_{PRE}$$

where $Z_{PRE}$ is the complex electrical impedance of the tissue prior to the treatment and $Z_{PRESENT}$ is the complex electrical impedance of the tissue at the moment measurement. Once a section of the tissue is frozen, the movement of the ions in that region becomes slower than the unfrozen section of the tissue, and the conduction of electricity occurs via capacitive instead of resistive means, which is what is detected by the above equation.

If the tissue is not frozen after this stage, as it may be indicated by a minimal change in the quantity $Z_{FROZEN}$, then the cooling target temperature is further reduced and the probe is cooled until a frozen stage is reached, repeating the same cycle. Once the tissue reaches a frozen stage, the Applicator TEMP is cooled to the determined cooling temperature for a predetermined and fixed second cooling duration, in which this second cooling duration may be a different amount on time from the first, and the electrical resistivity of the tissue. After this duration, the electrical resistivity of the tissue reduces to approximately half of its value when warm, and the Applicator TEMP is warmed to the target temperature for the remaining heating duration. Once this target temperature is met, the process is ended.

The embodiment of FIG. 43L utilizes ultrasound transducers to detect changes in the acoustic impedance of the tissue to assure that the treatment volume is frozen during the clinical procedure based on the algorithm of FIG. 43M. The ultrasound transducers are used to detect the boundary between the frozen (solid) and the unfrozen (soft) tissue, since the ultrasound reflects at the boundary with a reflection coefficient given as:

$$\Gamma = \frac{Z_2 - Z_1}{Z_2 + Z_1}$$

Where $\Gamma$ is the reflection coefficient, $Z_1$ is the acoustic impedance of region 1, i.e. the solid tissue, and $Z_2$ is the acoustic impedance of region 2, i.e. the unfrozen tissue.

The algorithm of FIG. 43M provides sensory feedback from ultrasound transducers located on the Applicator face to determine frozen tissue size. The Applicator TEMP is cooled to a cold target temperature for a predetermined first cooling duration, where the frost depth is determined by the use of an ultrasound transducer by way of boundary reflection between frozen (solid) and unfrozen (soft) tissue. If a sufficient amount of tissue is not frozen after this stage, the cooling target temperature is further decreased and cooled until a sufficient size is attained, repeating the same cycle. Once the tissue reaches a frozen stage, the Applicator TEMP is cooled to the determined cooling temperature for a predetermined and fixed second cooling duration, in which this second cooling duration may be a different amount of time from the first. After this duration, the Applicator TEMP is warmed to the target temperature for the remaining heating duration and the process is ended. In this process, once the tissue is frozen, the acoustic impedance of the tissue increases to approximately twice that of warm tissue.

The embodiment of FIG. 43N utilizes RF heaters to periodically and quickly warm the superficial layers of the tissue while keeping the deeper tissues cold by way of the algorithm of FIG. 43O. The algorithm of FIG. 43O allows the heating of the shallow tissue with RF heater electrodes attached to the bottom of the Applicator to minimize mucosal damage. The algorithm of this embodiment cools the Applicator TEMP (in which TEMP can be either the face or tissue temperature) for a predetermined and fixed cooling duration while periodically turning on the RF heater. After the cooling duration is reached, the Applicator face or tissue temperature is warmed to a target temperature for the heating duration, ending the treatment process.

One application of this embodiment is using the RF heater for periodic heating of the tissue under the Applicator to reduce frost bite damage. For example, the tissue that is 4-5 mm deep may be over cooled and could be beyond the reach of the cryoprotectant agent, in which a RF heater would be needed.

The algorithm of FIG. 43N utilizes temperature sensors to perform cryolysis with a controlled cooling rate. In this embodiment of a control algorithm, the control algorithm is utilized to cool the treatment region with a linear cooling rate rather than an exponential rate. To do so, once the algorithm is initialized, the Applicator temperature is measured via temperature sensors. From this measurement, the cooling rate is calculated by dividing the temperature reduction by the time taken to reach that temperature. If the Applicator target temperature is not reached, and the cooling rate is not at the target, the cooling strength is adjusted and the Applicator temperature is read again until the Applicator target is reached. If the Applicator target temperature is not reached but the cooling rate is at the proper target, the Applicator temperature is measured again until the Applicator target temperature is reached. Once the Applicator target temperature is reached, the Applicator is maintained at the target temperature for the intended duration. Once the duration of treatment has finished the operation is ended.

The algorithm of FIG. 43O utilizes total energy readings for treatment by setting a desired about of cooling energy for the treatment and terminating the operation once that amount of energy is reached. Once the algorithm is initialized the coolant temperature is measured at the Applicator inlet and outlet every pre=determined second interval. The cooling energy is then calculated and if the cooing energy target is not reached the algorithm is looped again, starting with the measurement of coolant temperature at the Applicator inlet and outlet. Once the cooling energy target is reached, the operation is ended and treatment is ended.

Referring to FIGS. 43A-43O, all embodiments are described in regards to treating the base of tongue. However, all control algorithms presented may be used for any treatment region, with the proper physical embodiment. For example, treatment of the soft palate probe could require temperature sensors placed on the soft palate probe and soft palate insulator, regulating the treatment by measuring the posterior side of the soft palate, using a control algorithm similar to FIG. 43A.

Control algorithms may not only be for regulation of treatment parameters, but can also be useful for equipment testing and operation of the temperature determinant. For example, the controller may use the resistance for testing of the probe's digital circuitry/temperature sensing. Using the known resistance values built into the probes digital circuit, once the probe is connected to power/console the digital circuitry can read the resistance values and verify that they are the expected values. If the values are the expected values, then the probes digital circuitry and sensors are working correctly. Similar techniques can be used to test different microcontrollers and hardware being utilized throughout the system. Another example of a self-testing system would be verifying the pressure of the system to ensure there is no blockage or leakage. For example, upon console initiation fluid can be ran between cold and warm tanks with a pump, and if the pressure reading in the fluid is above or below an expected value, the console can notify the user that something is wrong. This concept can be used during a specific self-test on start-up or during a procedure to ensure the probe does not have a blockage. This means of self-testing may be used any time before, during, or after a procedure.

Figure 44A:
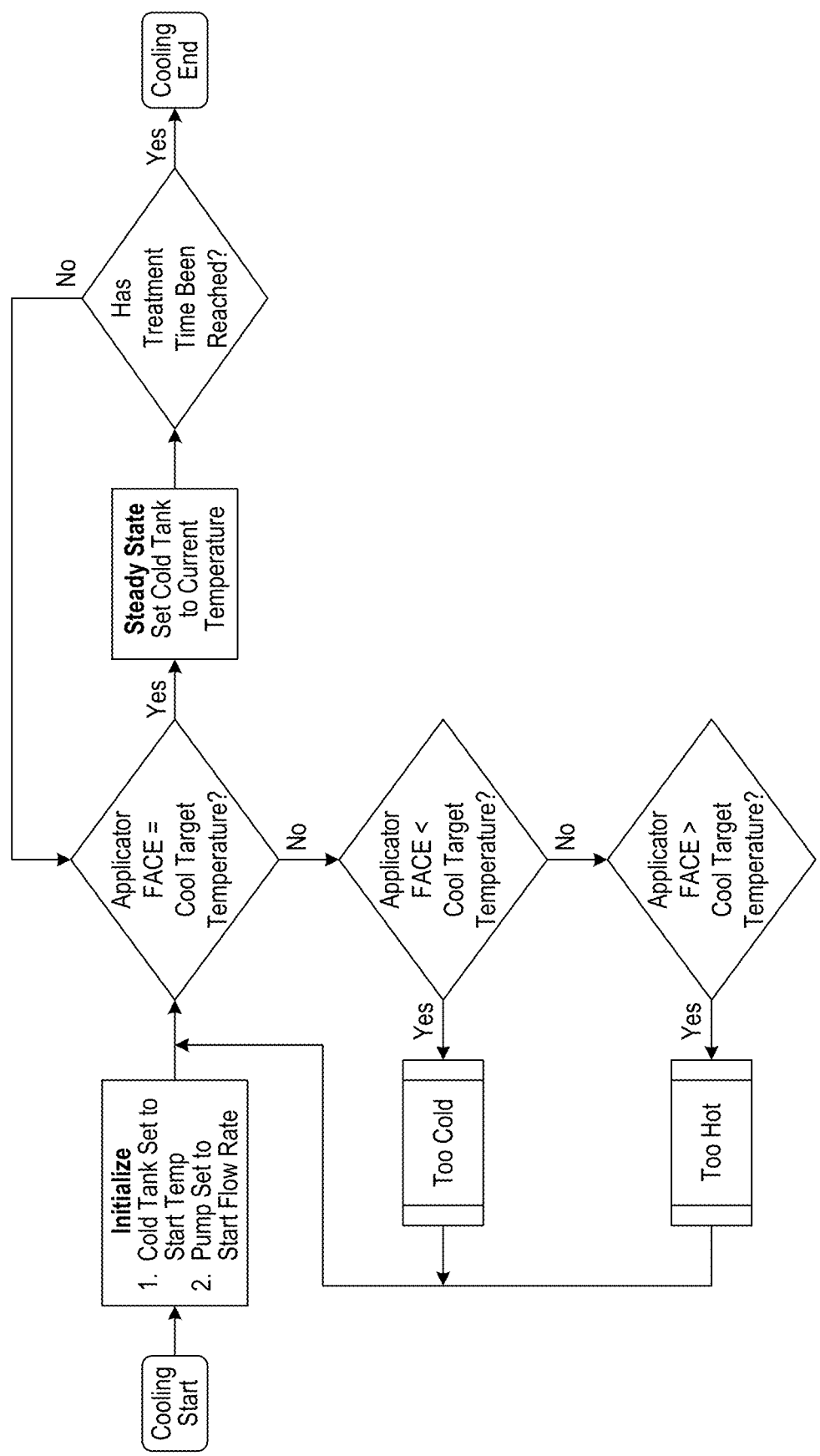

FIGS. 44A-44D illustrate an algorithm for the automatic control of the temperature determinant. FIG. 44A illustrates the cooling process from the beginning to end of the operation. Once the operation begins, the temperature determinates parameters are initialized by setting the desired temperature of the chiller and the desired flow rate of the pump. The temperature of the applicator face is then checked by way of temperature sensors to see if the applicator face is within the proper range of the desired treatment temperature. If not, the face temperature of the applicator is checked to see if it is too cold or too hot for treatment. If the applicator face is too cold, the subroutine "TOO COLD" is performed, shown in FIG. 44C. If the applicator face is too hot, the subroutine "TOO HOT" is performed, shown in FIG. 44D. Once the applicator face is in range of the target temperature, the chiller is set to the current temperature of the applicator face and the chiller and applicator are in steady state. To ensure that the chiller and applicator stay in range of the target temperature, the algorithm checks to see if the treatment time has been reached. If not, the temperature sensors check to see the temperature of the applicator face and repeat the process described above. If the treatment time has been reached, the cooling algorithm is ended.

Figure 44B:
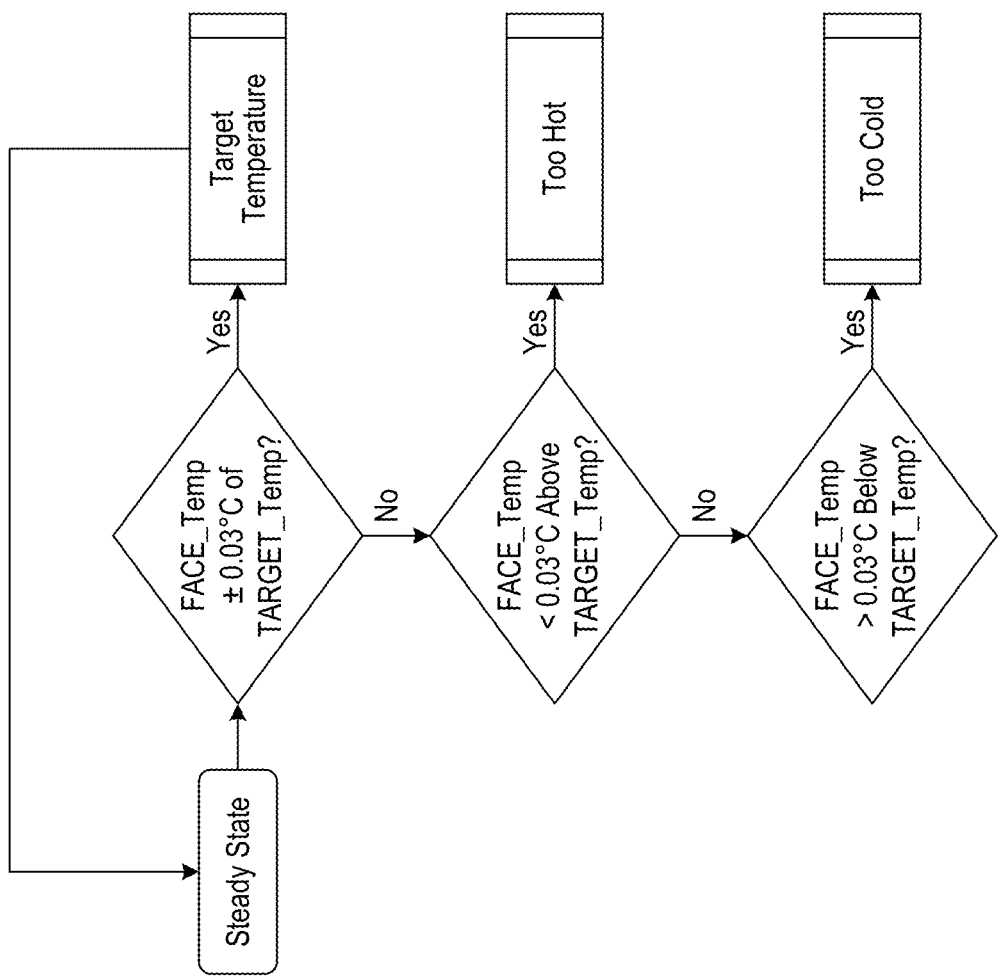

FIG. 44B illustrates an embodiment of the algorithm that specifies the temperatures for "target temperature," "too cold," and "too hot." In this embodiment, for the algorithm to register that the face temperature of the applicator is within the desired range, the face temperature of the applicator must be ±0.03° C. from the predetermined target temperature. For the algorithm to register that the temperature is too hot, the face of the applicator must read greater than 0.03° C. above the target temperature. Lastly, for the algorithm to register that the temperature is too cold, the face of the applicator must read 0.03° C. below the target temperature.

Figure 44C:
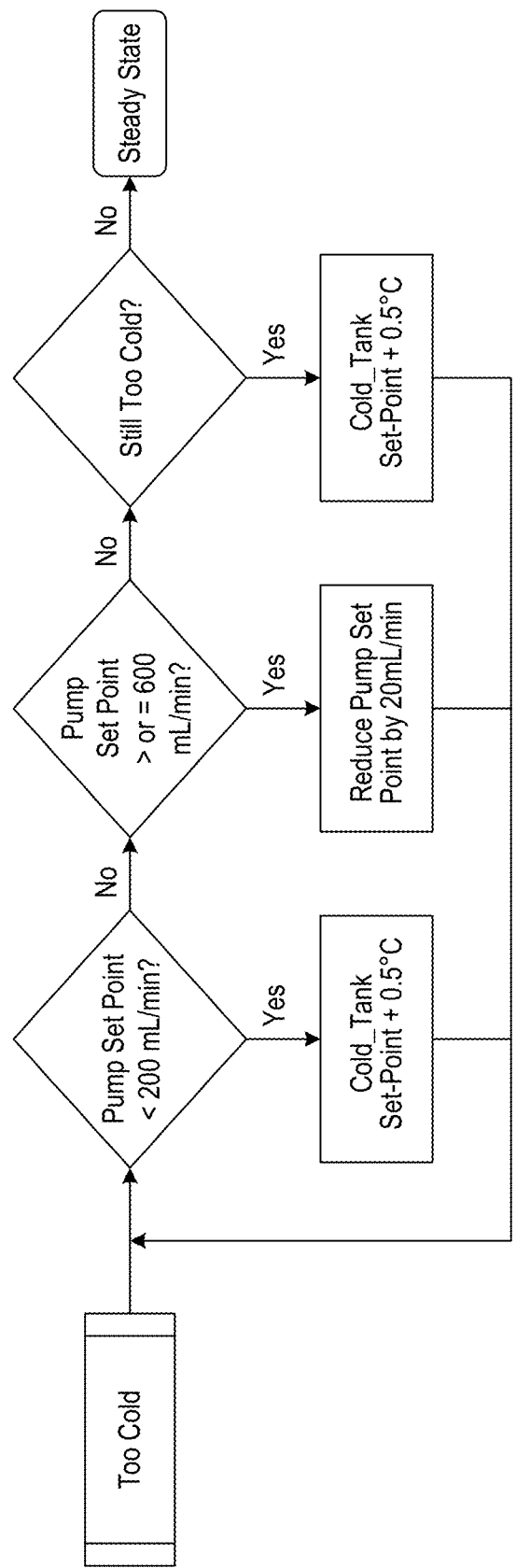
Figure 44D:
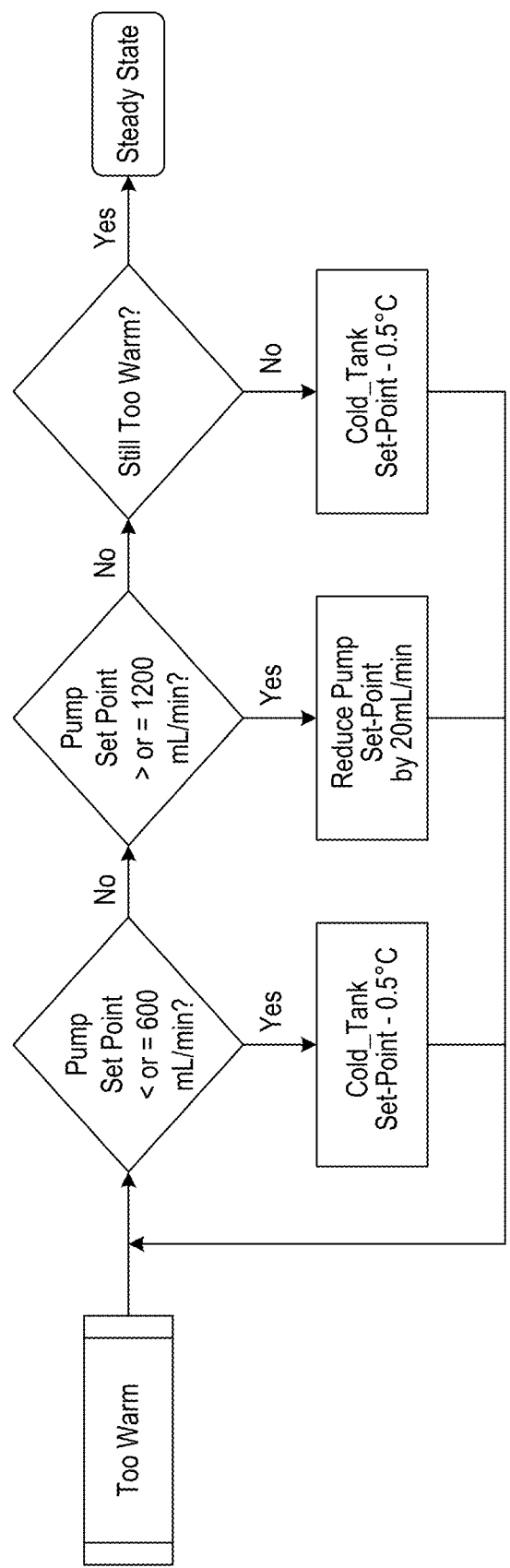

FIGS. 44C-44D describes the subroutines in the main temperature determinant algorithm for driving the face applicator temperature towards steady state with the chiller. For both subroutines, the Applicator temperature is controlled by adjusting the speed of the coolant pump as well as the temperature of the coolant reservoir. Until the target temperature is reached, the pump is ran at maximum speed. Afterwards, the fine control is achieved by regulating the pump speed while alterations in the reservoir temperature provides the course corrections. FIG. 44C illustrates an embodiment of the subroutine for correcting the temperature of the applicator when the applicator face is too cold. In this embodiment, the pump setpoint desired is between 200 to 600 mL/min. To acquire this pump speed, the algorithm checks if the pump speed is too low, and if so increases the pump set point by 20 mL/min. If the pump speed if too high, the pump set point is reduced by 20 mL/min. If the pump set point is between 200 to 600 mL/min, the algorithm checks to see if the chiller is still trying to cool; if so, the chiller set point is increased by 0.5° C. If the chiller is not still trying to cool, the pump speed and chiller are within their desired parameters and the applicator temperature is corrected.

FIG. 44D illustrates an embodiment of the subroutine for correcting the temperature of an applicator when the applicator face is too hot. In this embodiment, the pump setpoint desired is between 600 to 1200 mL/min. To acquire this pump speed, the algorithm checks if the pump speed is too low, and if so increases the pump set point by 20 mL/min. If the pump speed if too high, the pump set point is reduced by 20 mL/min. If the pump set point is between 600 to 1200 mL/min, the algorithm checks to see if the chiller is still trying to cool; if so, the chiller set point is decreased by 0.5° C. If the chiller is not still trying to cool, the pump speed and chiller are within their desired parameters and the applicator temperature is corrected. Upper and lower limits placed on the pump speed assures the continuous operation of the control system while protecting the pump from being damaged. Furthermore, the upper limit imposed on the pump speed assures that the internal fluid pressures do not exceed safe limits causing coolant leakage. FIGS. 44A-44D described embodiments with specific parameters such as pump speed and chiller temperature, however, these parameters may be altered depending on the treatment.

Utilization of these feedback mechanisms allows the possibility of fully automated control systems. For example, the controller may pick initial treatment parameters, such as the power to apply to start the cooling, based on population parameters, and then switch to custom values based on the patient's specific information; such as the rate of cooling per Watt. In other examples, the controller may utilize a parameter estimator. In the most advanced installment, the controller may extract information from the sensor data, and if allowed by the operator, the controller individualizes the treatment to patient, by calculating cooling energy, estimating the overall system time constant (including chiller, pump, Applicator, tissue and human body) and works as a PID controller. In response to unwanted outcomes, such as oscillations in temperature control or discontinuities, the system may also make needed changes to provide proper treatment to the patient. For example, if oscillations are observed in the time vs. temperature traces, the system could respond by decreasing the Applicator pressure to suppress the oscillations. In response to discontinuities caused by unknown factors, the system may interpret then based on previous observations/outcomes from other patients and adjust treatment accordingly. Having a fully automated control system is also beneficial in the case of a physical or system error, in which the system can detect the error and issue a warning or stop treatment if, for example, a leak is detected. The embodiments of FIGS. 43A-43O are not mutually exclusive, and the invention may employ some, all, or none of the feedback algorithms or various combinations of the algorithms as described above.

FIG. 45 shows a typical strength—duration curve for the therapy as a function of the therapy duration and therapy temperature. Below the efficacy line shown as a dashed line, therapy is ineffective since either the temperatures are not cold enough or the treatment is not long enough to cause cryolysis. Above the safety line shown as a dotted line, there is a potential for damage to the mucosa or the epithelium. Hence, it is preferable that the treatment parameters be chosen such that they fall within the safe and effective zone.

FIGS. 46A-46B illustrate a device 4602 for pretreatment bioimpedance testing and the theory behind the device, to determine whether a patient is suitable for cryolysis. The device of FIG. 46A is shaped similar to the base of tongue applicator, with bioimpedance sensors 4604 disposed on the bottom of the device and configured to measure, sense, or obtain quadripolar impedance measurements from the target tissue. With impedance measurements, the resistance and reactance are read, giving a full impedance measurement while also changing the frequency of the electrical signal. Using these measurements, the phase angle can be calculated (either onboard the device or remotely on the console/controller), which may be used for calculating a patient's fat percentage, since fat and muscle cells respond differently to electrical signals at a certain frequency. When the patient's fat percentage is calculated, a determination can be made if the target tissue is a candidate for cryo therapy according to the other embodiments described herein. FIG. 46B describes the relationship between phase angle, impedance, resistance, and frequency.

FIGS. 47A and 47B demonstrate the procedure a patient undergoes with a sleep apnea treatment system of the present disclosure, where FIG. 47A illustrates the first stage of treatment; the application of the base of tongue cryoprobe or applicator. It should be understood that any of the applicators described herein can be substituted in this embodiment for the base of tongue cryoprobe or applicator. The patient is prepared for treatment by first having a bite block placed within the patient's mouth to ensure adequate opening and stabilization of the jaw. Additionally, a teeth guard is placed over the lower teeth to provide protection to the underside of the tongue. A cryoprotectant agent is then applied to the cryoprobe, base of tongue, epiglottis, and vallecula. The cryoprobe is then secured in place on the target tissue (e.g., the base of tongue by the traction stand), which may assure that the optimal contact force is maintained between the cryoprobe and the target tissue. The fluid management system then circulates the coolant through the cryoprobe, extracting heat and cooling the target tissue for a period of time at a predetermined temperature. For example, the circulation of coolant through the cryoprobe may be applied for 60 minutes while brining and keeping the cryoprobe temperature at −27° C. Treatment temperatures in the range of −2° C. to −40° C. can be used. After the treatment duration is completed, the fluid management system circulates warmed coolant through the cryoprobe, rewarming the base of tongue, again for a predetermined time and temperature. For example, the rewarming of the base of the tongue may last for 10 minutes while the probe is brought and kept at a temperature of +37° C. At the end of the rewarming phase, the first stage of the treatment is concluded, the base of tongue cryoprobe is removed and the second phase of treatment may commence.

FIG. 47B illustrates the second phase of treatment; utilizing the retropalatal cryoprobe. First, a cryoprotectant agent is applied to the cryoprobe, soft palate, lateral fat pads, and surrounding tissue. Afterwards, the cryoprobe is secured in place on the soft palate by the traction stand. The fluid management system then circulates coolant through the cryoprobe, cooling the soft palate for a predetermined time and temperature. For example, the circulation of coolant through the retropalatal cryoprobe may be for 30 minutes while bringing and keeping the retropalatal cryoprobe to a temperature of −20° C. Treatment temperatures in the range of −2° C. to −40° C. can be used. After the treatment duration has ended, the fluid management system circulates warmed coolant through the cryoprobe, rewarming the soft palate for a predetermined time and temperature. For example, the rewarming of the base of the tongue may last for 10 minutes at a temperature of +37° C. After the rewarming phase has ended, the retropalatal cryoprobe is removed and the second stage of the treatment is completed.

Lymphoid tissue found in the upper airway may contribute to sleep apnea and be reduced using controlled cryogenic temperatures or other methods of selective destruction. The adenoid pad found in the superior border of the nasopharynx is an example of this lymphoid tissue.

In some embodiments, an Applicator can be introduced nasally or orally to reach the pad. The Applicator may make contact with the entire surface or partial surface of the adenoid pad and delivery a temperature sufficient to cause immediate or delayed destruction.

For the oral introduction, the Applicator is advanced from the oral cavity passed under the soft palate before turning up in cranial direction toward the adenoids. Steering could be accomplished using image guided methods, such as fluoroscopy or endoscopy.

In some embodiments, the Applicator may be rigid with a fixed angle to reach to adenoid pad. In other embodiments, the applicator may be flexible or steerable.

In some embodiments, the Applicator may cause heat exchange through metal, plastic or other rigid material. In other embodiments, the Applicator may be a balloon.

In some embodiments, the Applicator may be a balloon embedded in a single or multiple camera flexible nasopharyngoscope.

It is to be understood that although the above description of the Applicator is summarized by emphasizing its use on tongue and soft palate tissues, nothing in the description prevents its use on the fat containing tissues including but not limited to the oropharynx, the hard palate, the uvula, the lateral pharyngeal wall, or the lingual tonsils. Furthermore, various kinds of Applicators, including but not limited to the surface contact type, penetrating type, multi-segment type and balloon type can be designed and used on one or more of the fat containing tissues as listed above.

The various illustrative embodiments of devices, systems, and methods described herein are not intended to be limited to the particular forms disclosed. Rather, they include all modifications and alternatives falling within the scope of the claims.

The various illustrative embodiments of devices, systems, and methods described herein are not intended to be limited to the particular forms disclosed. Rather, they include all modifications and alternatives falling within the scope of the claims. The claims are not intended to include, and should not be interpreted to include, means-plus- or step-plus-function limitations, unless such a limitation is explicitly recited in a given claim using the phrase(s) "means for" or "step for," respectively.

What is claimed is listed below:

1. A device for treating obstructive sleep apnea, the device comprising:

an applicator including
- a hollow interior portion having one or more baffles that at least partially define a flow path through the hollow interior portion;
- an inlet port fluidically coupled to the hollow interior portion, wherein the inlet port is configured to receive a fluid;
- an outlet port fluidically coupled to the hollow interior portion, wherein the outlet port is configured to remove the fluid; and
- an active surface sized and shaped to contact oropharyngeal tissue of a patient, wherein:
- the active surface is thermally coupled to the hollow interior portion such that, in operation, heat from the fluid is transferred through the active surface,
- the active surface includes a proximal region having a first width and a distal region having a second width smaller than the first width,
- the active surface includes a long axis extending from the proximal region to the distal region and a short axis angled relative to the long axis,
- the active surface is curved and includes a radius of curvature that decreases in a distal direction along the long axis,
- a thickness of the applicator decreases in the distal direction along an entirety of the long axis such that the applicator includes a first thickness at the proximal region and a second thickness smaller than the first thickness at the distal region.

2. The device of claim 1, wherein a width of the active surface decreases in the distal direction along the entirety of the long axis.

3. The device of claim 1, wherein the thickness of the applicator tapers in the distal direction along the long axis.

4. The device of claim 1, wherein the long axis has a concave shape and the short axis has a convex shape.

5. The device of claim 1, wherein the applicator comprises a first side and a second side opposite the first side, wherein the inlet port and the outlet port are positioned at least partially at the first side of the applicator, and wherein the active surface is positioned at the second side of the applicator.

6. The device of claim 1, wherein the inlet port and the outlet port are positioned at a proximal end of the applicator.

7. The device of claim 1, wherein the applicator comprises a first portion and a second portion coupled to the first portion, and wherein the first portion and the second portion together define the hollow interior portion.

8. The device of claim 1, wherein the applicator comprises a first portion and a second portion fixedly coupled to the first portion, and wherein the first portion includes the inlet port and the outlet port and the second portion includes the active surface.

9. The device of claim 1, wherein the active surface extends in the distal direction along the entirety of the long axis.

10. The device of claim 1, wherein the second width of the distal region of the active surface decreases in the distal direction along the long axis.

11. The device of claim 1, wherein the radius of curvature of the active surface includes a first concavity and a second concavity distal to and greater than the first concavity.

12. The device of claim 1, wherein the active surface is sized and shaped to cover an entirety of a surface area of the oropharyngeal tissue.

13. The device of claim 1, wherein the applicator is made from a rigid material.

* * * * *